US011826389B2

(12) United States Patent
Aroian et al.

(10) Patent No.: US 11,826,389 B2
(45) Date of Patent: Nov. 28, 2023

(54) PURIFIED ANTHELMINTIC COMPOSITIONS AND RELATED METHODS

(71) Applicant: UNIVERSITY OF MASSACHUSETTS, Boston, MA (US)

(72) Inventors: Raffi Van Aroian, Worcester, MA (US); Gary R. Ostroff, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 17/729,785

(22) Filed: Apr. 26, 2022

(65) Prior Publication Data

US 2022/0354905 A1     Nov. 10, 2022

Related U.S. Application Data

(62) Division of application No. 16/607,677, filed as application No. PCT/US2018/033962 on May 22, 2018.

(60) Provisional application No. 62/510,081, filed on May 23, 2017.

(51) Int. Cl.
| | |
|---|---|
| *C12P 21/06* | (2006.01) |
| *A61K 35/741* | (2015.01) |
| *A61P 33/10* | (2006.01) |
| *A61K 9/48* | (2006.01) |
| *A61K 38/16* | (2006.01) |
| *A61K 45/06* | (2006.01) |

(52) U.S. Cl.
CPC .............. *A61K 35/741* (2013.01); *A61K 9/48* (2013.01); *A61K 38/164* (2013.01); *A61P 33/10* (2018.01); *A61K 45/06* (2013.01)

(58) Field of Classification Search
CPC .................................................. A61K 35/741
See application file for complete search history.

(56) References Cited

U.S. PATENT DOCUMENTS

| | | | |
|---|---|---|---|
| 4,865,981 | A | 9/1989 | Herrnstadt et al. |
| 5,591,433 | A | 1/1997 | Michael et al. |
| 5,596,071 | A | 1/1997 | Payne et al. |
| 7,351,881 | B2 | 4/2008 | Carozzi et al. |
| 7,923,602 | B2 | 4/2011 | Carozzi et al. |
| 8,809,268 | B2 | 8/2014 | Aroian et al. |
| 10,940,170 | B2 | 3/2021 | Aroian et al. |
| 11,484,568 | B2 | 11/2022 | Aroian et al. |
| 2001/0010932 | A1 | 8/2001 | Schnepf et al. |
| 2006/0014942 | A1 | 1/2006 | Lereclus et al. |
| 2009/0260107 | A1 | 10/2009 | English et al. |
| 2010/0024075 | A1 | 1/2010 | Aroian et al. |
| 2010/0203521 | A1 | 8/2010 | Klapperich et al. |
| 2011/0263489 | A1 | 10/2011 | Aroian et al. |
| 2015/0079203 | A1 | 3/2015 | Thomas et al. |
| 2017/0348362 | A1 | 12/2017 | Aroian et al. |
| 2019/0015474 | A1 | 1/2019 | Aroian et al. |
| 2020/0188452 | A1 | 6/2020 | Aroian et al. |
| 2021/0268045 | A1 | 9/2021 | Aroian et al. |
| 2023/0128953 | A1 | 4/2023 | Aroian et al. |

FOREIGN PATENT DOCUMENTS

| | | |
|---|---|---|
| CN | 1488615 A | 9/2003 |
| EP | 3630150 A1 | 4/2020 |
| WO | WO 1989/007605 A1 | 8/1989 |
| WO | WO 2007/062064 A2 | 5/2007 |
| WO | WO 2010/053517 A2 | 5/2010 |
| WO | WO 2016/100128 A1 | 6/2016 |
| WO | WO 2017/123946 A1 | 7/2017 |
| WO | WO 2018/217807 A1 | 11/2018 |

OTHER PUBLICATIONS

Capello et al., "A Purified Bacillus Thuringiensis Crystal Protein with Therapeutic Activity Against the Hookworm Parasite Ancylostoma Ceylanicum", Proceedings of the National Academy of Science, Oct. 10, 2006, vol. 103, No. 41, pp. 15154-15159.

Crickmore et al., "Revision of the Nomenclature for the Bacillus thuringiensis Pesticidal Crystal Proteins", Microbiology and Molecular Biology Reviews 62(3): 807-813, Sep. 1998.

De Maagd et al., "How Baccillus thuringiensis has evolved specific toxins to colonize the insect world", Trends in Genetics 17(4): 193-199, Apr. 2001.

Durmaz et al., "Intracellular and Extracellular Expression of Bacillus thuringiensis Crystal Protein CRY5B in Lactococcus Lactis for Use as an Anthelminthic", American Society for Microbiology Applied and Environmental Microbiology, Feb. 2016, vol. 82, No. 4, pp. 1286-1294 doi: 10.1128/AEM.02365-15.

Extended European Search Report for European Patent Application No. 18805734.3, dated Mar. 31, 2021.

Ge et al., "Hyperexpression of a Baccillus thuringiensis delta-endotoxin-encoding gene in *Escherichia coli*: properties of the product", Gene 93: 49-54, 1990.

(Continued)

*Primary Examiner* — Albert M Navarro
(74) *Attorney, Agent, or Firm* — LATHROP GPM LLP; James H. Velema; Judith L. Stone-Hulslander

(57) ABSTRACT

Compositions and methods for treating or reducing the severity of occurrence of a parasitic worm or helminth infection in a subject are described. The methods include administering to the subject a therapeutically effective amount of a composition comprising isolated native, bioactive nematicidal crystals formed from a single type of nematicidal crystal protein. The isolated native, bioactive nematicidal crystals are substantially free of any bacterial spores or host bacterial proteins, other than nematicidal crystal protein in the form of a crystal. Methods for making isolated native, bioactive nematicidal crystals are also described. The crystal proteins may be full length, truncated, variant, or sub-variant Cry proteins. Examples of crystal proteins include Cry5B, Cry21, Cry14A, Cry6A, and Cry13A.

20 Claims, 23 Drawing

(56) References Cited

OTHER PUBLICATIONS

Hu et al., "Discovery of a highly synergistic anthelmintic combination that shows mutual hypersusceptibility" PNAS, vol. 107, No. 13, pp. 5955-5960, Mar. 30, 2010.

International Search Report and Written Opinion in related PCT Application No. PCT/US2018/033962, dated Oct. 3, 2018 (26 pages).

Kunle et al., "Antimicrobial activity of various extracts and carvacrol from Lippia multiflora leaf extract", Phytomedicine, vol. 10, pp. 59-61, 2003.

Kurek et al., "How composition and process parameters affect volatile active compounds in biopolymer films," Carbohydrate Polymers, vol. 88, pp. 646-656, 2012.

Lereclus et al., "Overproduction of Encapsulated Insecticidal Crystal Proteins in a Bacillus Thuringiensis Spo0A Mutant", Nature Biotechnology, Jan. 1, 1995, vol. 13, pp. 67-70.

Lereclus et al., "Transformation and Expression of a Cloned δ-Endotoxin Gene In Bacillus Thuringiensis", FEMS Microbiology Letters, Jul. 1989, vol. 60, Issue 2, pp. 211-217.

Malvar and Baum, "Tn5401 Disruption of the spoOF Gene Identified by Direct Chromosomal Sequencing, Results in CryIIIA Overproduction in Bacillus thuringiensis", J Bacteriol. 176, 4750-4753, 1994.

Mounsef et al., "A simple method for the separation of Bacillus thuringiensis spores and crystals", Journal of Microbiological Methods, vol. 107, pp. 147-149, 2014.

Partial European Search Report received for European Patent Application No. 18805734.3, dated Dec. 1, 2020.

Peltzer et al., "Migration of carvacrol as a natural antioxidant in high-density polyethylene for active packaging," Food Additives and Contaminants, vol. 26, No. 6, pp. 938-946, 2009.

Peng et al., "A δ-endotoxin encoded in Pseudomonas fluorescens displays a high degree of insecticidal activity", App. Microbiol Biotech, 63: 300-306, 2003.

Rowley et al., "Solvent extraction of penicillin," Journal of the Society of Chemical Industry, vol. 65, No. 8, pp. 237-240, 1946.

Sandman et al., "Genetic Analysis of Bacillus subtilis spo Mutations Generated by Tn917-Mediated Insertional Mutagenesis", Genetics, vol. 117, pp. 603-617, Dec. 1987.

Schnepf et al., "Bacillus thuringiensis and Its Pesticidal Crystal Proteins", Microbiology and Molecular Biology Reviews, vol. 62, No. 3, pp. 775-806, Sep. 1998.

Silvaggi et al., "Unmasking Novel Sporulation Genes in Bacillus subtillus", J Bacteriol. vol. 186, No. 23, pp. 8089-8095, Dec. 2004.

Sivropoulou et al., "Antimicrobial and Cytotoxic Activities of Origanum Essential Oils," Journal of Agricultural and Food Chemistry, vol. 44, No. 5, pp. 1202-1205, 1996.

Steidler et al., "Biological containment of genetically modified Lactococcus lactis for intestinal delivery of human interleukin 10", Nat Biotechnol 21: 785-789, 2003.

Valadares de Amorim, et al., "Identification of Bacillus thuringiensis subsp. kurstaki Strain HD1-Like Bacteria from Environmental and Human Samples after Aerial Spraying of Victoria, British Columbia, Canada, with Foray 48B", Applied And Environmental Microbiology, Mar. 2001, 67(3): 1035-1043.
Zhang et al., "Evaluation of alginate—whey protein microcapsules for intestinal delivery of lipophilic compounds in pigs," J Sci Food Agric, vol. 96, pp. 2674-2681, 2016.
Agaisse et al., 1994. Expression in Bacillus subtilis of the Bacillus thuringiensis crylllA toxin gene is not dependent on a sporulation-specific sigma factor and is increased in a spo0A mutant. J. Bacteriol., 176(15):4734-4741.
Agaisse et al., 1994. Structural and functional analysis of the promoter region involved in full expression of the crylllA toxin gene of Bacillus thuringiensis. Mol. Microbiol., 13(1):97-107.
Ashikaga et al. (2000) "Natural genetic competence in Bacillus subtilis natto OK2," J Bacteriol. 182(9):2411-5.
Battcock, Fao Agricultural Services Bulletin No. 134, 1998.
Baum et al. (1995) "Regulation of insecticidal crystal protein production in *Bacillus thuringiensis*," Mol. Microbiol. 18:1-12.
Beasley et al. (2004) "Nisin-producing *Lactococcus lactis* strains isolated from human milk," Appl Environ Microbiol. 70(8):5051-3.
Bermúdez-Humaráet al., "Lactococci and lactobacillin as mucosal delivery vectors for therapeutic proteins and DNA vaccines", Microbial Cell Factories, 2011, pp. 1-10.
Berrelli et al. (Nov. 16, 2012) "Interactions between parasites and microbial communities in the human gut," Front Cell Infect Microbiol. 2:141. pp. 1-6.
Bethony et al. (2006) "Soil-transmitted helminth infections: ascariasis, trichuriasis, and hookworm," Lancet 367:1521-1532.
Betz et al. (2000) "Safety and advantages of *Bacillus thuringiensis*-protected plants to control insect pests," Regul. Toxicol. Pharmacol. 32(2): 156-73.
Beveridge, "Cellular Responses of *Bacillus* subtilis and *Escherichia coli* to the Gram Stain", Journal of Bacteriology 1983, 156: 846-858.
Bischof et al. (2006) "Assays for toxicity studies in C. elegans with Bt crystal proteins," Methods Mol. Biol. 351:139-154.
Boontawan et al., 2005, Mass transfer of terpenes through a silicone rubber membrane in a liquid-liquid contacting system. Biotechnol. Prog., 21:1680-1687.
Braat et al. (2006) "A phase I trial with transgenic bacteria expressing interleukin-10 in Crohn's disease," Clin. Gastroenterol. Hepatol. 4:754-759.
Brans et al. (2004) "New integrative method to generate *Bacillus* subtilis recombinant strains free of selection markers," Appl. Environ. Microbiol. 70:7241-7250.
Brooker et al. (2008) "Hookworm-related anaemia among pregnant women: a systematic review," PLoS Negl. Trop. Dis. 2:e291. pp. 1-9.
Buasri et al. (Jan. 20, 2012) "Large crystal toxin formation in chromosomally engineered *Bacillus thuringiensis* subsp. aizawai due to σE accumulation," Appl. Environ. Microbiol. 78:1682-1691.
Cannon (1996) "*Bacillus thuringiensis* use in agriculture: a 30 molecular perspective," Biol. Rep. 71:561-636.
Casula et al. (2002) "*Bacillus* probiotics: spore germination in the gastrointestinal tract," Appl. Environ. Microbiol. 68:23442352.
Chan et al., Thompson IP, 2013, Resolving the mechanism of bacterial inhibition by plant secondary metabolites employing a combination of whole-cell biosensor. J. Microbiol. Methods, 9 Pages.
Coêlho et al., "Probiotic Therapy: A Promising Strategy for the Control of Canine Hookworm", Journal of Parasitology Research, 2013, 6 pages.
Conlan et al. (Apr. 2012) "Soil-transmitted helminthiasis in Laos: a community—wide cross-sectional study of humans and dogs in a mass drug administration environment," Am. J. Trop. Med. Hyg. 86:624-634.
Cutting (2011) "*Bacillus* probiotics," Food Microbiol. 28:214220.
D'Arienzo et al. (2006) "Bacillus subtilis spores reduce susceptibility to Citrobacter rodentium-mediated enteropathy in a mouse model," Res. Microbiol. 157:891-897.
Dubnau et al. (1971) "Fate of transforming DNA following uptake by competent Bacillus subtilis. I. Formation and properties of the donor-recipient complex," J. Mol. Biol. 56:209-221.
Duc et al. (2003) "Bacterial spores as vaccine vehicles," Infect. Immun. 71:2810-2818.
Duc et al. (2004) "Characterization of Bacillus probiotics available for human use," Appl. Environ. Microbiol. 70(4):2161-2171.
El-Bendary (2006) *Bacillus thuringiensis* and Bacillus sphaericus biopesticides production, J. Basic Microbiol. 46:158-170.
Entomological Society of America (ESA), Is BT Safe for Human to Eat?, May 1, 2018, pp. 1-3.
Ferrer-Miralles, "Bacterial cell factories for recombinant protein production; expanding the catalogue", Microbial Cell Factories, 2013, 12:113.
Fujiwara et al., 2006. Comparative immunology of human and animal models of hookworm infection. Parasite Immunol., 28:285-293.
Geary et al. (2010) Unresolved issues in anthelmintic pharmacology for helminthiases of 30 humans, Int. J. Parasitol. 40:1-13.

(56) References Cited

OTHER PUBLICATIONS

Geertsma et al. (2007) "High-throughput cloning and expression in recalcitrant bacteria," Nat Methods. 4:705-707.
Genbank Database [Online] (Sep. 23, 2008) "truncated Cry5B [synthetic construct]," Accession No. ACI01644. National Center for Biotechnology Information. Accessible on the Internet at URL: https://www.ncbi.nlm.nih.gov/protein/ACI01644. [Last Accessed May 4, 2017].
Goh et al. (2009) "Development and application of a upp-based counterselective gene replacement system for the study of the S-layer protein SlpX of *Lactobacillus acidophilus* NCFM," Appl. Environ. Microbiol. 75(10):3093-105.
Griffitts et al. (2001) "Bt toxin resistance from loss of a putative carbohydrate-modifying enzyme," Science. 293(5531):860-4.
Griffitts et al. (2005) "Glycolipids as receptors for Bacillus thuringiensis crystal toxin," Science. 307:922-925.
Griffitts et al. (2005) "Many roads to resistance: how invertebrates adapt to Bt toxins," Bioessays. 27:614-624.
Hall et al. (2008) "A review and metaanalysis of the impact of intestinal worms on child growth and nutrition," Matern. Child Nutr. 4(Suppl 1): 118-236.
Hoa et al. (2000) "Characterization of *Bacillus* species used for oral bacteriotherapy and bacterioprophylaxis of gastrointestinal disorders," Appl. Environ. Microbiol. 66:5241-5247.
Hoa et al. (2001) "Fate and dissemination of *Bacillus subtilis* spores in a murine model," Appl. Environ. Microbiol. 67:3819-3823.
Hoang et al. (2008) "Recombinant Bacillus subtilis expressing the Clostridium perfringens alpha toxoid is a candidate orally delivered vaccine against necrotic enteritis," Infect. Immun. 76:5257-5265.
Holck et al. (1992) "Cloning, sequencing and expression of the gene encoding the cell-envelope-associated proteinase from *Lactobacillus paracasei* subsp. *paracasei* NCDO 151," J. Gen. Microbiol. 138(7): 1353-64.
Holden-Dye et al. (2007) "Anthelmintic drugs," WormBook. 2:1-13.
Hong et al. (2008) "The safety of Bacillus subtilis and Bacillus indicus as food probiotics," J. Appl. Microbiol. 105:510-520.
Hotez PJ. 2008. Forgotten people, forgotten diseases: the neglected tropical diseases and their impact on global health and development. ASM Press, Washington, DC.
Hu et al. (2009) "The new anthelmintic tribendimidine is an L-type (levamisole and pyrantel) nicotinic acetylcholine receptor agonist," PLoS Negl. Trop. Dis. 3:e499. pp. 1-9.
Hu et al. (2010) "*Bacillus thuringiensis* Cry5B protein is highly efficacious as a single-dose therapy against an intestinal roundworm infection in mice," PLoS Negl. Trop. Dis. 4:e614. pp. 1-7.
Hu et al. (2012) "Promise of *Bacillus thuringiensis* crystal proteins as anthelmintics," In; Parasitic Helminths: Targets, Screens, Drugs and Vaccines. Ed.: Caffery. Wiley—VCH Verlag Gmh & Co. Weinheim, Germany. pp. 267-281.
Hu et al. (Jul. 8, 2013) "*Bacillus subtilis* strain engineered for treatment of soil—transmitted helminth diseases," Appl. Environ. Microbiol. 79(18):5527-5532.
Hu et al. (Nov. 8, 2012) "Mechanistic and single-dose in vivo therapeutic studies of Cry5B anthelmintic action against hookworms," PLoS Negl. Trop. Dis. 6:e1900. pp. 1-8.
Hu et al., 2013, An extensive comparison of the effect of anthelmintic classes on diverse nematodes. PLoS One, 8(7):e70702, 12 pages.
Humphries et al. (2011) "Epidemiology of hookworm infection in Kintampo North Municipality, Ghana: patterns of malaria coinfection, anemia, and albendazole treatment failure," Am. J. Trop. Med. Hyg. 84:792800.
International Search Report and Written Opinion for PCT International Application No. PCT/US2017/013436, dated May 24, 2017.
International Search Report with Written Opinion for PCT International Patent Application No. PCT/US2015/038881, dated Oct. 14, 2015.
Keiser et al. (2008) "Efficacy of current drugs against soil-transmitted helminth infections: systematic review and meta-analysis," JAMA 299:1937-48.
Keiser et al. (2010) "The drugs we have and the drugs we need against major helminth infections," Adv. Parasitol. 73:197-230.
Kho et al. (2011) "The pore-forming protein Cry5B elicits the pathogenicity of *Bacillus* sp. against Caenorhabditis elegans," PL0S One 6:e29122. pp. 1-9.
Knopp et al. (Apr. 20, 2012) "Nematode infections: soil-transmitted helminths and trichinella," Infect. Dis. Clin. North Am. 26:341-358.
Krings U, Berger RG. 1998. Biotechnological production of Øavours and fragrances. Appl. Microbiol. Biotechnol., 49:1-8.
La Ragione et al. (2001) "*Bacillus subtilis* spores competitively exclude *Escherichia coli* O78:K80 in poultry," Vet. Microbiol. 79:133-142.
La Ragione et al. (2003) "Competitive exclusion by *Bacillus* subtilis spores of *Salmonella enterica* serotype Enteritidis and Clostridium perfringens in young chickens," Vet. Microbiol. 94:245-256.
Latsenko, "Molecular Mechanisms of Caenorhabditis elegans—*Bacillus* Interactions", Dissertation, der Eberhard Karls Universitht Tubingen, Jun. 23, 2014.
Law et al. (1995) "A system to generate chromosomal mutations in *Lactococcus lactis* which allows fast analysis of targeted genes," J. Bacteriol. 177:7011-7018.
Lee et al., 2011, Utility of capsule endoscopy for evaluating anthelmintic efficacy in fully conscious dogs. Int. J. Parasitol., 41:1377-1383.
Lee et al., 2015, Determination of anthelmintic efficacy against Toxocara canis in dogs by use of capsule endoscopy. Vet. Parasitol., 212:227-231.
Li et al. (2008) "Expression of Cry5B protein from *Bacillus thuringiensis* in plant roots confers resistance to root-knot nematode," Biol. Control. 47(1): 97-102.
Los et al. (2011) "RAB-5- and RAB-11-dependent vesicle-trafficking pathways are required for plasma membrane repair after attack by bacterial poreforming toxin," Cell Host Microbe 9:147-157.
Maagd et al. (2001) "How *Bacillus thuringiensis* has evolved specific toxins to colonize the insect world." Trends in Genetics. 17(4):193-99.
Marroquin et al. (2000) "*Bacillus thuringiensis* (Bt) toxin susceptibility and isolation of resistance mutants in the nematode Caenorhabditis elegans," Genetics. 155:1693-1699.
McClemens et al. (Jun. 2013) "Lactobacillus rhamnosus Ingestion Promotes Innate Host Defense in an Enteric Parasitic Infection," Clinical and Vaccine Immunology. 20(6):818-826.
Mohamadzadeh et al. (2009) "Dendritic cell targeting of *Bacillus* anthracis protective antigen expressed by Lactobacillus acidophilus protects mice from lethal challenge," Pproc. Natl. Acad. Sci. USA. 106: 4331-4336.
Moran et al. (2009) G-finder Report: Neglected Disease Research and Development: New Times, New Trends. Global Fund of Innovation for Neglected Diseases, 106 Pages.
National Research Council. 1996. Guide for the care and use of laboratory animals. National Academies Press, Washington, DC.
Nih, "RecName: Full=Pesticidal crystal protein Cry5Ba; AltName: Full=140 kDa crystal protein; AltName: Full=Crystaline entomocidal protoxin; AltName: Full=Insecticidal delta-endotoxin CryVB(a)", UniProtKB/Swiss-Prot: Q45712.1, created Dec. 1, 2000.
Norton et al. (1996) "Factors affecting the immunogenicity of tetanus toxin fragment C expressed in Lactococcus lactis," FEMS Immunol. Med. Microbiol. 14:167-177.
Oddone et al. (2009) "Incorporation of nisl-mediated nisin immunity improves vector-based nisin-controlled gene expression in lactic acid bacteria," Plasmid. 61:151-158.
Permpoonpattana et al. (2011) "Immunization with *Bacillus* spores expressing toxin A peptide repeats protects against infection with Clostridium difficile strains producing toxins A and B," Infect. Immun. 79:22952302.
Phan et al. (2006) "Novel plasmid-based expression vectors for intra- and extracellular production of recombinant proteins in *Bacillus subtilis*," Protein Expr. Purif. 46(2):189-95.
Pusch et al. (2005) "Bioengineering Lactic Acid Bacteria to Secrete the HIV-1 Virucide Cyanovirin," J. Acquir. Immune. Defic. Syndr. 40(5):512-20.

(56) References Cited

OTHER PUBLICATIONS

Pusch et al. (2006) "An anti-HIV microbicide engineered in commensal bacteria: secretion of HIV-1 fusion inhibitors by lactobacilli," AIDS. 20:1917-1922.

Roh et al. (2007) "*Bacillus thuringiensis* as a specific, safe, and effective tool for insect pest control," J. Microbiol. Biotechnol. 17(4):547-59.

Romero et al. (2006) "Transformation of undomesticated strains of *Bacillus subtilis* by protoplast electroporation," J. Microbiol. Meth. 66(3):556-9.

Rudd A. de Maagd et al. (2001) "How *Bacillus thuringiensis* has evolved specific toxins to colonize the insect world," Trends in Genetics, 17(4):193-199.

Russell et al. (2001) "Identification and cloning of gusA, encoding a new beta—glucuronidase from Lactobacillus gasseri ADH," Appl. Environ. Microbiol. 67(3):1253-61.

Schallmey et al. (2004) "Developments in the use of *Bacillus* species for industrial production," Can. J. Microbiol. 50:1-17.

Schroeder et al. (2006) "Preventive effects of the probiotic *Escherichia coli* strain Nissle 1917 on acute secretory diarrhea in a pig model of intestinal infection," Dig. Dis. Sci. 51:724-731.

Shao et al. (2009) "Surface display of heterologous proteins in *Bacillus* thuringiensis using a peptidoglycan hydrolase anchor," Microb. Cell Fact. 8:48. pp. 1-17.

Shevchenko et al. (1996) "Mass spectrometric sequencing of proteins silver—stained polyacrylamide gels," Anal. Chem. 68:850-858.

Shkoporov et al. (2008) "Production of human basic fibroblast growth factor (FGF-2) in Bifidobacterium breve using a series of novel expression/secretion vectors," Biotechnol. Lett. 30:1983-1988.

Sierro et al. (2008) "DBTBS: a database of transcriptional regulation in *Bacillus subtilis* containing upstream intergenic conservation information," Nucleic Acids Res. 36:D93-D96.

Song et al. (Mar. 22, 2012) "Killed *Bacillus subtilis* spores as a mucosal adjuvant for an H5N1 vaccine," Vaccine 30:3266-3277.

Soukhathammavong et al. (Jan. 3, 2012) Low efficacy of single-dose albendazole and mebendazole against hookworm and effect on concomitant helminth infection in Lao PDR, PLos Negl. Trop. Dis. 6(1): e1417. pp. 1-8.

Steidler et al. (2000) "Treatment of murine colitis by *Lactococcus lactis* secreting interleukin-10," Science. 289:1352-1355.

Stepek et al. 2007. Anthelmintic action of plant cysteine proteinases against the rodent stomach nematode, Protospirura muricola, in vitro and in vivo. Parasitology, 134:103-112.

Stothard et al. (2009) "A spot-check of the efficacies of albendazole or levamisole against soil-transmitted helminthiases in young Ungujan children, reveals low frequencies of cure," Ann. Trop. Med. Parasitol. 103:357-360.

Tchuenté (2011) "Control of soil-transmitted 5 helminths in sub-Saharan Africa: diagnosis, drug efficacy concerns and challenges," Acta Trop. 120(Suppl 1):S4-S11.

Tritten et al. (2011) "In vitro and in vivo efficacy of monepantel (AAD 1566) against laboratory models of human intestinal nematode infections," PLoS Negl. Trop. Dis. 5:e1457. pp. 1-7.

Tritten et al. (Dec. 24, 2011) "In vitro and in vivo efficacy of tribendimidine and its metabolites alone and in combination against the hookworms Heligmosomoides bakeri and Ancylostoma ceylanicum," Acta Trop. 122:101-107.

Urban et al. (Jun. 20, 2013) "*Bacillus thuringiensis*-derived Cry5B has potent anthelmintic activity against Ascaris suum," PLoS Negl Trop Dis. 7(6):e2263. pp. 1-7.

Waeytens et al. (2008) "Paracellular entry of interleukin-10 producing *Lactococcus lactis* in inflamed intestinal mucosa in mice," Inflamm. Bowel Dis. 14(4):471-9.

Walker et al. (1996) "Electrotransformation of *lactobacillus acidophilus* group A1," FEMS Microbiol. Lett. 138(2-3):233-7.

Wang et al. (Aug. 3, 2012) "Improvement of crystal solubility and increasing toxicity against Caenorhabditis elegans by asparagine substitution in block 3 of *Bacillus thuringiensis* crystal protein Cry5Ba," Appl. Environ. Microbiol. 78:7197-7204.

Wei et al. (2003) "*Bacillus thuringiensis* crystal proteins that target nematodes," Proc Natl. Acad. Sci. USA. 100(5):2760-5.

Wells et al. (2008) "Mucosal delivery of therapeutic and prophylactic molecules using lactic acid bacteria," Nat Rev Microbiol. 6(5):349-62.

Yang et al. (1996) "Cloning and expression of full-length delta-endotoxin crylA(c) gene in three kinds of prokaryotic systems using shuttle vector pHT3101," Wei Sheng Wu Xue Bao. 36:173-180.—English Abstract Only.

Youngman et al. (1984) "Construction of a cloning site near one end of Tn917 into which foreign DNA may be inserted without affecting transposition in *Bacillus subtilis* or expression of the transposonborne erm gene," Plasmid 12:1-9.

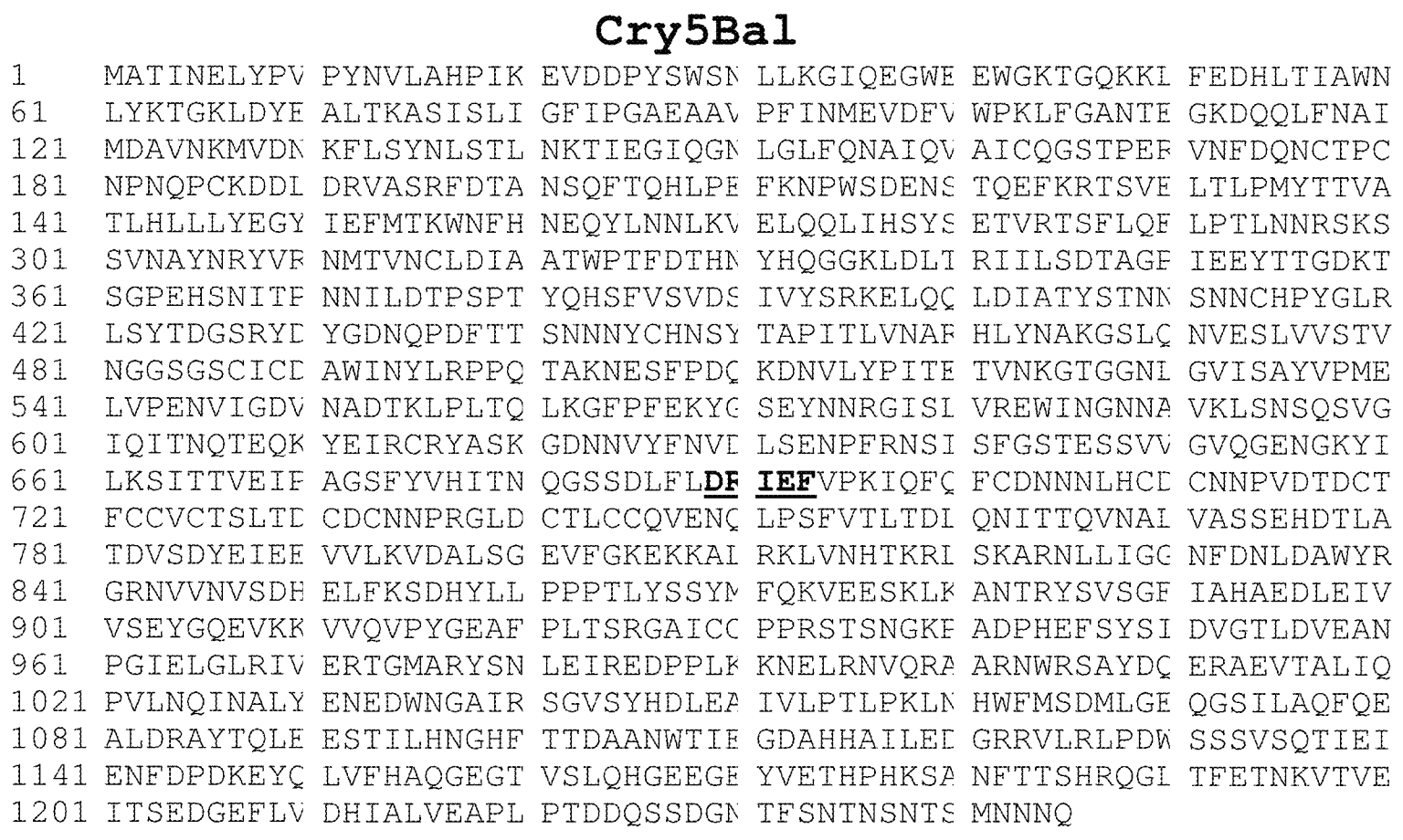

Cry5Ba1

```
   1  MATINELYPV PYNVLAHPIK EVDDPYSWSN LLKGIQEGWE EWGKTGQKKI FEDHLTIAWN
  61  LYKTGKLDYE ALTKASISLI GFIPGAEAAV PFINMEVDFV WPKLFGANTE GKDQQLFNAI
 121  MDAVNKMVDN KFLSYNLSTL NKTIEGIQGN LGLFQNAIQV AICQGSTPEF VNFDQNCTPC
 181  NPNQPCKDDI DRVASR

Cry13Aa1

```
1    MTCQLQAQPL IPYNVLAGYP TSNTGSPIGN AGNQFDQFEQ TVKELKEAWE AFQKNGSFSL
61   AALEKGFDAA IGGGSFDYLG LVQAGLGLVG TLGAAIPGVS VAVPLISMLV GVFWPKGTNN
121  QENLITVIDK EVQRILDEKL SDQLIKKINA DLNAFTDLVT RLEEVIIDAT FENHKPVLQV
181  SKSNYMKVDS AYFSTGGILT LGMSDFLTDT YSKLTFPLYV LGATMKLSAY HSYIQFGNTW
241  LNKVYDLSSD EGKTMSQALA RAKQHMRQDI AFYTSQALNM FTGNLPSLSS NKYAINDYNV
301  YTRAMVLNGL DIVATWPTLY PDDYSSQIKL EKTRVIFSDM VGQSESRDGS VTIKNIFDNT
361  DSHQHGSIGL NSISYFPDEL QKAQLRMYDY NHKPYCTDCF CWPYGVILNY NKNTFRYGDN
421  DPGLSGDVQL PAPMSVVNAQ TQTAQYTDGE NINTDTGRSW LCTLRGYCTT NCFPGRGCYN
481  NSTGYGESCN QSLPGQKIHA LYPFTQTNVL GQSGKLGLLA SHIPYDLSPN NTIGDKDTDS
541  TNIVAKGIPV EKGYASSGQK VEIIREWING ANVVQLSPGQ SWGMDFTNST GGQYMVRCRY
601  ASTNDTPIFF NLVYDGGSNP IYNQMTFPAT KETPAHDSVD NEILGIKGIN GNYSLMNVKD
661  SVELPSGKFH VFFTNNGSSA IYLDRLEFVP LDQPAAPTQS TQPINYPITS RLPHRSGEPP
721  AIIWEKSGNV RGNQLTISAQ GVPENSQIYL SVGGDRQILD RSNGFKLVNY SPTYSFTNIQ
781  ASSSNLVDIT SGTITGQVQV SNL
```

*Fig. 3*

Cry14Aa1

```
1     MDCNLQSQQN IPYNVLAIPV SNVNALVDTA GDLKKAWEEF QKTGSFSLTA LQQGFSASQG
61    GAFNYLTLLQ SGISLAGSFV PGGTFVAPIV NMVIGWLWPH ENKTADTENL IKLIDEEIQK
121   QLNKALLDQD RNNWTSFLES IFDTSATVSN ADIDAQWSGT VDTTNRQQKT PTTSDYLNVV
181   GKFDSADSSI ITNENQIMNG NFDVAAAPYF VDGATLRLSL YQSYIKFCNS WIDAVGFSTN
141   DANTQKANLA RTKLTMRSTI NEYTQRVMKV FKDSKNMPTI GTNKFSVDAY NVYVKGMTLN
301   VLDMVAIWSS LYPNDYTSQT AIEQTRVTFS NMVGQEEGTD GTLKIYNTFD SLSYQHSLIP
361   NNNVNLISYY TDELQNLELA VYTPKGGSGY AYPYGFILNY ANSNYKYGDN DPTGKPLNKQ
421   DGPIQQINAA TQNSKYLDGE TINGIGASLP GYCTTGSSAT EQPFSCTGTA NSYKASCNPS
481   DTNQKINALY AFTQTNVKGS TGKLGVLASL VPYDLNPKNV FGELDSDTNN VILKGIPAEK
541   GYFPNNARPT VVKEWINGAS AVPFYSGNTL FMTATNLTAT QYKIRIRYAN PNSDTQISVL
601   ITQNGSQISN SNLTLYSTTD SSMSSNLPQN VYVTGENGNY TLLDLYSTTN VLSTGDITLK
661   LTGGNQKIFI DRIEFIPTMP VPAPTNNTNN NNGDNGNNNP PHHGCAIAGT QQLCSGPPKF
721   EQVSDLEKIT TQVYMLFKSS SYEELAIKVS SYQINQVALK VMALSDEKFC EEKRLLRKLV
781   NKANQLLEAR NLLVGGNFET TQNWVLGTNA YDNYDSFLFN GNYLSLQPAS GFFTSYAYQK
841   IDESTLKPYT RYKVSGFIGQ SNQVELIISR YGKEIDKILN VPYAGPLPIT ADASITCCAP
901   EIDQCDGGQS DSHFFNYSID VGALHPELNP GDEIGLKIVQ SNGYISISNL EIIEERPLTE
961   MEIQAVNRKD QKWKRELLLE CASVSELLQP IDNQIDSLFK DANWYNDILP HVTYQTLKNI
1021  IVPDLPKLKH WFIDHLPGEY HEIEQKMKEA LKHAFTQLDE KNLIHNGHFA TNLIDWQVEG
1081  DAFMKVLENN ALALQLSNWD SSVSQSIDIL EFDEDKAYKL RVYAQGSGTI QFGNCEDEAI
1141  QFNTNSFVYK EKIIYFDSPS INLHIQSEGS EFVVSSIDLV ELSDDE
```

Fig. 4

Cry14Aa1

MTNPTILYPSYHNVLAHPIRLDSFFDPFVETFKDLKGAWEEFGKTGYMDPLKQHLQIAWD
TSQNGTVDYLALTKASISLIGLIPGADAVVPFINMFVDFIFPKLFGRGSQQNAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPNLSTNDNTPDFNSDTVLLTLPMYTTGATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVTGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLTSYQVLQMEVTNQTTQKYRIR
IRYATGGDTAASIWFHIIGPSGNDLTNEGHNFSSVSSRNKMFVQGNNGKYVLNILTDSIE
LPSGQQTILIQNTNSQDLFLDRIEFISLPSTSTPTSTNFVEPESLEKIINQVNQLFSSSS
QTELAHTVSDYKIDQVVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVVSRYGKEVHDMLDIPYEEALPISSDESPNCCKPAACQCSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPASDYQHLSAVVVPTLPKQRHWFMEGREGE
HVVLTQQFQQALDRAFQQIEEQNLTHNGNLANGLTDWTVTGDAQLTIFDEDPVLELAHWD
ASISQTIEIMDFEGRHRIQTACTWKRQRNSYRSTWRKRLETMTFNTTSFTTQEQTFYFEG
DTVDVHVQSENNTFLIDSVELIEIIEE

*Fig. 5A*

Cry21Aa2
(98% identical to Cry21Aa1)

MTNPTILYPSYHNVLAHPIRLDSFFDPFVETFKDLKSAWEEFGKTGYMDPLKQHLQIAWD
TSQNGTVDYLALTKASISLIGLIPGADAVVPFINMFVDFIFPKLFGRGSQQNAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPNLSTNDNTPDFNSDTVLLTLPMYTTAATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVAGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLTSYQVLKMEVTNQTTQKYRIR
IRYATGGDTAASIWFHIIGPSGNDLTNEGHNFSSVSSRNKMFVQGNNGKYVLNILTDSIE
LPSGQQTILIQNTNSQDLFLDRIEFISLPSTSTPTSTNFVEPESLEKIINQVNQLFSSSS
QTELAHTVSDYKIDQVVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVVSRYGKEVHDMLDIPYEEALPISSDESPNCCKPAACQCSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPHVTYQHLSAVVVPTLPKQRHWFMEDREGE
HVVLTQQFQQALDRAFQQIEEQNLIHNGNFANGLTDWTVTGDAQLSIFDEDPVLELAHWD
ASISQTIEIMDFEEDTEYKLRVRGKGKGTVTVQHGEEELETMTFNSTSFTTQEQTFYFEG
DTVDVHVQSENNTFLIDSVELIEIIEE

*Fig. 5B*

MIIDSKTTLPRHSLIHTIKLNSNKKYGPGDMTNGNQFIISKQEWATIGAYIQTGLGLPVNEQQLRTHVNL
SQDISIPSDFSQLYDVYCSDKTSAEWWNKNLYPLIIKSANDIASYGFKVAGDPSIKKDGYFKKLQDELDN
IVDNNSDDDAIAKAIKDFKARCGILIKEAKQYEEAAKNIVTSLDQFLHGDQKKLEGVINIQKRLKEVQTA
LNQAHGESSPAHKELLEKVKNLKTTLERTIKAEQDLEKKVEYSFLLGPLLGFVVYEILENTAVQHIKNQI
DEIKEQLDSAQHDLDRDVKIIGMLNSINTDIDNLYSQGQEAIKVFQKLQGIWATIGAQIENLRTTSLQEV
QDSDDADEIQIELEDASDAWLVVAQEARDFTLNAYSTNSRQNLPINVISDSCNCSTTNMTSNQYSNPTTN
MTSNQYMISHEYTSLPNNFMLSRNSNLEYKCPENNFMIYWYNNSDWYNNSDWYNN

*Fig. 5C*

Legend
1. IBaCC homogenized (5 ul, 200 OD)
2. IBaCC homogenized sup (15 ul)
3. Water layer (15 ul)
4. NaCl wash (15 ul)
5. PBS wash (15 ul)
6. PCC oil wash final (5 ul, OD 312) large scale

US 11,826,389 B2

PURIFIED ANTHELMINTIC COMPOSITIONS AND RELATED METHODS

RELATED APPLICATIONS

This application is a division of U.S. patent application Ser. No. 16/607,677, filed Oct. 23, 2019, which is a 35 U.S.C. § 371 filing of International Patent Application No. PCT/US2018/033962, filed May 22, 2018, which claims priority to U.S. Provisional Patent Application Ser. No. 62/510,081, filed May 23, 2017, the entire contents of which are incorporated herein by reference.

STATEMENT OF FEDERALLY SPONSORED RESEARCH

This invention was made with government support under Grant Nos. AI056189 awarded by the United States Department of Health and Human Services (HHS) National Institutes of Health (NIH), and NIFA 2016-67015-24861 awarded by the United States Department of Agriculture (USDA) National Institutes of Food and Agriculture (NIFA). The government has certain rights in this invention.

SEQUENCE LISTING

The instant application contains a Sequence Listing which has been submitted electronically in ASCII format and is hereby incorporated by reference in its entirety. Said ASCII copy, created on Apr. 26, 2022, is named 729036_UM9-222USDIV_ST25.txt and is 55.3 kilobytes in size.

BACKGROUND

Soil-transmitted helminthes (STHs) that parasitize the GI tract of humans infect 2.3 billion of the poorest peoples and >400,000,000 of the poorest children worldwide. Crystal (Cry) proteins made by the soil bacterium *Bacillus thuringiensis* (Bt) are candidate agents that provide safe and effective treatment of STHs. However, despite the established anthelmintic biological activity of Cry proteins, significant challenges remain with respect to effective delivery of intact, biologically active Cry proteins into the gastrointestinal (GI) tract of humans and animals for treating STHs. The cost and scalability of Cry protein expression and purification limits its application as a practical STH therapy in the developing world where treatments must be available at a very low cost (less than $1/dose) and in very large quantities to treat a large and poor patient population.

A cheap, simple, and scalable way to deliver Cry proteins is to express it in *B. thuringiensis*, which is ideally suited to express very high levels of Cry protein and which is already fermented cheaply on a massive scale for environmental release. However, production of high levels of Cry protein in Bt requires sporulation. Thus, the Cry protein compositions currently deployed into the environment are in the form of a "spore-crystal lysate" (SCL) that includes both the crystal protein and spores from the bacterium. Use of these SCL compositions in humans is problematic due to the presence of bacterial spores which can contain many of the enterotoxin genes that causes food poisoning in humans. Furthermore, the inclusion of Bt spores makes formulation for administration to humans and animals both more difficult, as spores are difficult to work with, and less efficient, since gram-for-gram any formulation would necessarily include a significant amount of inactive ingredient (spore) along with active ingredient (crystal). Separation of spores from crystal proteins is difficult as the two are very similar in size.

Accordingly, there remains an urgent need in the art for new approaches to delivering protein therapeutics such as anthelmintic proteins to the GI tract.

SUMMARY

The instant disclosure is based on the discovery that a sporulation defective or sporulation incompetent bacterium can be employed for production of highly purified preparations of nematicidal crystals suitable for pharmaceutical use. The purified nematicidal crystal preparations of the invention offer superior anti-helminthic properties to crystal proteins purified from spore crystal lysate (SCL). Moreover, such preparations are substantially free of contaminating spores and host bacterial proteins which are unsuitable for administration to humans. In certain exemplary embodiments, the preparations are substantially free of soluble cell components, lipids, and cell wall debris.

In one aspect, the instant disclosure provides a pharmaceutical composition comprising an isolated native, bioactive nematicidal crystal formed from a single type of nematicidal crystal protein. The nematicidal crystal protein is produced by a non-sporulating form of host bacterium, and the pharmaceutical composition is substantially free of any bacterial spores or host bacterial proteins other than nematicidal crystal protein in the form of a crystal.

In certain embodiments, the pharmaceutical composition includes excipients suitable for oral administration to a human subject. In certain embodiments, the host bacterium is a *Bacillus* species. In some embodiments, the host bacterium is a *Bacillus thuringiensis* (Bt). In some embodiments, the host bacterium is an *Escherichia coli* or *Pseudomonas fluorescens* species.

In some embodiments, the non-sporulating host bacterium is genetically engineered to have a genetic mutation that results in a defect in sporulation such that the native, bioactive nematicidal crystal is trapped in the cytosol of the bacterium. In certain embodiments, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In one embodiment, the genetic mutation resulting in a defect of sporulation is the deletion or inactivation of the spo0A gene.

In some embodiments, the host bacterium is genetically engineered to express the single type of nematicidal crystal protein under the control of a non-sporulation specific promoter. In certain embodiments, the non-sporulation specific promoter is a Cry3A, GerA, GNAT, or TadA promoter. In certain embodiments, the single type of nematicidal crystal protein is selected from the group consisting of Cry5B, Cry5C, Cry5D, Cry6A, Cry13A, Cry14A, Cry21A, Cry21B, Cry 55B, and variants and truncations thereof. In certain embodiments, the nematicidal crystal protein is Cry5B, or variants or fragments thereof. In some embodiments, the nematicidal crystal protein is Cry5B variant Ser407Cys.

In certain embodiments of the pharmaceutical compositions disclosed herein, the pharmaceutical compositions further comprise a second crystal protein in the form of an isolated native, bioactive nematicidal crystal formed from only the second crystal protein.

In some embodiments, the pharmaceutical composition comprises at least 95% isolated native, bioactive nematicidal crystal content.

In some embodiments the isolated native, bioactive nematicidal crystals are in an orally-available dosage form. In some embodiments, the pharmaceutical composition is in a dry powdered form and is encapsulated by a pharmaceutical capsule.

In another aspect, the disclosure provides a method for producing a pharmaceutical composition of the invention, the method comprising: (a) growing a non-sporulating form of a host bacterium that is genetically engineered to express a single type of nematicidal crystal protein, wherein the non-sporulating host bacterium produces native, bioactive nematicidal crystals formed from the single type of nematicidal crystal protein, wherein the host bacterium is grow in a growth medium, and optionally wherein the non-sporulating host bacterium releases the native, bioactive nematicidal crystals into the growth medium; and (b) isolating and concentrating the native, bioactive nematicidal crystals to form isolated, native, bioactive nematicidal crystals.

In some embodiments of this method, the host bacterium is a *Bacillus* species. In some embodiments, the host bacterium is a *Bacillus thuringiensis* (Bt). In some embodiments, the host bacterium is an *E. coli* or *P. fluorescens* species.

In some embodiments of the methods, the non-sporulating host bacterium is genetically engineered to have a genetic mutation that results in a defect in sporulation such that the native, bioactive nematicidal crystal is trapped in the cytosol of the bacterium. In some embodiments, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In some embodiments, the genetic mutation resulting in a defect of sporulation is the deletion or inactivation of the spo0A gene.

In certain embodiments of the method above, the host bacterium is genetically engineered to express the single type of nematicidal crystal protein under the control of a non-sporulation specific promoter. In certain embodiments, the non-sporulation specific promoter is a Cry3A, GerA, GNAT, or TadA promoter. In certain embodiments, the single type of nematicidal crystal protein is selected from the group consisting of Cry5B, Cry5C, Cry5D, Cry6A, Cry13A, Cry14A, Cry21A, Cry 21B, Cry 55B, and variants and truncations thereof. In certain embodiments, the nematicidal crystal protein is Cry5B, or variants or fragments thereof. In some embodiments, the nematicidal crystal protein is Cry5B variant Ser407Cys.

In certain embodiments, the method further comprises a step of exposing the non-sporulating host bacterium to an antimicrobial compound to inactivate the host bacterium. In certain embodiments, the antimicrobial compound is iodine. In certain embodiments, the antimicrobial compound is a pharmaceutical antibiotic. In certain embodiments, the antimicrobial compound is a beta-lactam antibiotic. In certain embodiments, the antimicrobial compound is an organic solvent selected form the group consisting of a terpene, hexane, and formaldehyde. In certain embodiments, the antimicrobial compound is a terpene. In certain embodiments, the terpene is selected from the group consisting of thymol, eugenol, geraniol, carvacrol, and citral, or a combination thereof. In certain embodiments, the terpene is carvacrol. In certain embodiments, the antimicrobial compound is hexane.

In certain embodiments, the method includes a step of adding a food-grade oil to the inactivated host bacterium to extract the inactivating agent from the nematicidal crystal protein. In certain embodiments, the food-grade oil is selected from the group consisting of corn oil, soybean oil, coconut oil, cottonseed oil, olive oil, palm oil, peanut oil, rapeseed oil, safflower oil, and sunflower oil. In some embodiments, the food-grade oil is corn oil. In some embodiments, the food-grade oil is corn oil. In certain embodiments, the method includes a step of a step of adding an organic solvent to the inactivated host bacterium to extract cell components from the nematicidal crystal protein. In certain embodiments, the organic solvent is hexane. In certain embodiments, the hexane is added to the inactivated host bacterium to 50% v/v. In certain embodiments, the method includes a step of centrifuging the mixture of organic solvent and inactivated host bacterium to pellet the nematicidal crystal protein.

In certain embodiments, the method further includes a step of homogenizing the inactivated host bacterium to form a bacterial lysate that includes the native, bioactive nematicidal crystals. In some embodiments, the method further includes a step of concentrating the bacterial lysate. In certain embodiments, the step of concentrating the bacterial lysate is selected from the group consisting of centrifugation, ultrafiltration, and diafiltration.

In some embodiments, the method further comprises a step of formulating the isolated native, bioactive nematicidal crystals in an orally-available dosage form. In some embodiments, the step of formulating comprises lyophilizing or spray-drying the isolated native, bioactive nematicidal crystals. In some embodiments, the step of formulating comprises encapsulating the isolated native, bioactive nematicidal crystals in a pharmaceutical-grade capsule.

In still another aspect, the disclosure provides a method for producing a pharmaceutical composition, including: (a) growing a non-sporulating form of a host bacterium that is engineered to express a single type of nematicidal crystal protein, wherein the non-sporulating host bacterium produces native bioactive nematicidal crystals formed from the single type of nematicidal crystal protein; (b) inactivating the grown non-sporulating host bacterium by exposing the grown non-sporulating host bacterium to an antimicrobial compound; (c) homogenizing the inactivated non-sporulating host bacterium to form a bacterial lysate; and (d) concentrating the native bioactive nematicidal crystals in the bacterial lysate to form isolated native, bioactive nematicidal crystals.

In some embodiments, this method further comprises a step of concentrating the grown nonsporulating host bacterium before inactivating the grown non-sporulating host bacterium. In some embodiments, the host bacterium is a *Bacillus* species. In some embodiments, the host bacterium is a *Bacillus thuringiensis* (Bt). In certain embodiments, the host bacterium is an *E. coli* or *P. fluorescens* species.

In some embodiments of this method, the non-sporulating host bacterium is genetically engineered to have a genetic mutation that results in a defect in sporulation such that the native, bioactive nematicidal crystal is trapped in the cytosol of the bacterium. In some embodiments, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In certain embodiments, the genetic mutation resulting in a defect of sporulation is the deletion or inactivation of the spo0A gene.

In some embodiments of the method, the host bacterium is genetically engineered to express the single type of nematicidal crystal protein under the control of a non-sporulation specific promoter. In certain embodiments, the non-sporulation specific promoter is a Cry3A, GerA, GNAT, or TadA promoter. In certain embodiments, the single type of nematicidal crystal protein is selected from the group consisting of Cry5B, Cry5C, Cry5D, Cry6A, Cry13A, Cry14A, Cry21A, Cry 21B, Cry 55B, and variants and truncations thereof. In certain embodiments, the nematicidal crystal protein is Cry5B, or variants or fragments thereof. In some embodiments, the nematicidal crystal protein is Cry5B variant Ser407Cys.

In some embodiments of the methods, the antimicrobial compound is iodine. In other embodiments of the methods, the antimicrobial compound is a pharmaceutical antibiotic. In some embodiments of the methods, the antimicrobial compound is a beta-lactam antibiotic. In some embodiments, the antimicrobial compound is an organic solvent selected from the group consisting of a terpene, hexane, or formaldehyde. In certain embodiments, the antimicrobial compound is a terpene. In some embodiments, the terpene is selected from the group consisting of thymol, eugenol, geraniol, carvacrol, and citral, or a combination thereof. In certain embodiments, the terpene is carvacrol. In certain embodiments, the antimicrobial compound is hexane.

In some embodiments, the method further comprises a step of extracting the antimicrobial compound from the inactivated host bacterium. In certain embodiments, the method includes a step of adding a food-grade oil to the inactivated host bacterium to extract the inactivating agent from the nematicidal crystal protein. In certain embodiments, the food-grade oil is selected from the group consisting of corn oil, soybean oil, coconut oil, cottonseed oil, olive oil, palm oil, peanut oil, rapeseed oil, safflower oil, and sunflower oil. In some embodiments, the food-grade oil is corn oil. In certain embodiments, a step of adding an organic solvent to the inactivated host bacterium to extract cell components from the nematicidal crystal protein. In certain embodiments, the organic solvent is hexane. In certain embodiments, the hexane is added to the inactivated host bacterium to 50% v/v. In certain embodiments, the method includes a step of centrifuging the mixture of organic solvent and inactivated host bacterium to pellet the nematicidal crystal protein.

In some embodiments, the method includes a step of formulating the isolated native, bioactive nematicidal crystals in an orally-available dosage form. In some embodiments, the method includes the step of formulating comprises lyophilizing or spray drying the isolated native, bioactive nematicidal crystals. In some embodiments, the step of formulating comprises encapsulating the isolated purified native, bioactive nematicidal crystals in a pharmaceutical-grade capsule.

In yet another aspect, the disclosure provides a method of treating a parasitic worm infection in a subject comprising: administering to the subject a therapeutically effective amount of a pharmaceutical composition comprising isolated native, bioactive nematicidal crystals formed from a single type of nematicidal crystal protein, wherein the pharmaceutical composition does not contain bacterial spores.

In some embodiments of the method of treating, the nematicidal crystal protein is selected from the group consisting of Cry5B, Cry5C, Cry5D, Cry6A, Cry13A, Cry14A, Cry21A, Cry 21B, Cry 55B, and variants and truncations thereof. In some embodiments, the nematicidal crystal protein is Cry5B. In some embodiments, the nematicidal crystal protein is Cry5B variant Ser407Cys.

In some embodiments of the method of treating, the composition further comprises a second crystal protein in the form of an isolated native, bioactive nematicidal crystal formed from only the second crystal protein. In some embodiments, the pharmaceutical composition comprises at least about 95% isolated native, bioactive nematicidal crystal. In some embodiments, the composition is in a dry powdered form and is encapsulated by a pharmaceutical capsule.

BRIEF DESCRIPTION OF THE DRAWINGS

FIG. 1A is depicts the positions of conserved blocks among certain Cry proteins. de Maagd, R. A., et al. "How *Bacillus thuringiensis* has evolved specific toxins to colonize the insect world." Trends in Genetics 17(4): 193-99, 195 (FIG. 2a) (April 2001). FIG. 1B illustrates the positions of conserved blocks among certain Cry proteins. Schnepf, E., et al. "*Bacillus thuringiensis* and Its Pesticidal Crystal Proteins." Microbiology and Molecular Biology Reviews 62(3): 775-806, 781 (FIG. 3) (September 1998).

FIG. 2 illustrates the amino acid sequence of Cry5Ba1 [SEQ ID NO:1].

FIG. 3 illustrates the amino acid sequence of Cry13Aa1 [SEQ ID NO:2].

FIG. 4 illustrates the amino acid sequence of Cry14Aa1 [SEQ ID NO:3].

FIGS. 5A-5C show amino acid sequences of other crystal proteins. FIG. 5A illustrates the amino acid sequence of Cry21Aa1 [SEQ ID NO:4]. FIG. 5B illustrates the amino acid sequence of Cry21Aa2 (98% identical to Cry21Aa1) [SEQ ID NO:5]. FIG. 5C illustrates the amino acid sequence of Cry6A [SEQ ID NO:6].

DETAILED DESCRIPTION

Figure 1A:
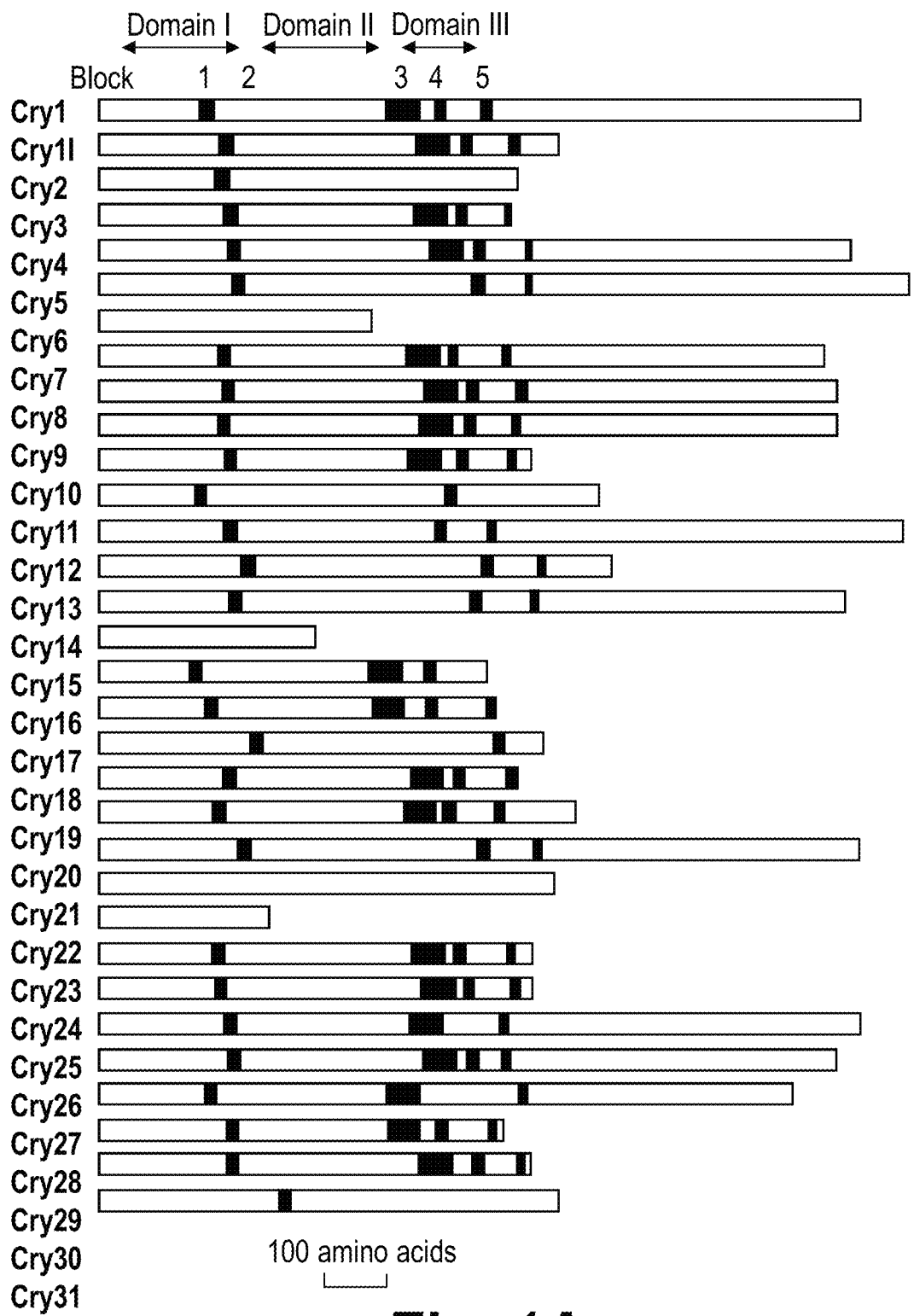
FIGS. 1A-1B are diagrams showing conserved blocks of amino acids in wild-type crystal proteins.

Disclosed are compositions of purified nematicidal crystal proteins, methods for making such purified nematicidal crystal proteins, and methods for treating or preventing STH infection by administering to a subject a preparation of purified nematicidal crystal proteins.

Microbes

In certain embodiments, the bacteria of the disclosure are non-sporulating bacteria. As used herein, the term "non-sporulating bacterium" includes wild-type bacteria that are incapable of producing spores (e.g., certain Gram-negative bacteria) as well as genetic variants of spore-forming bacteria that have been engineered to be defective in sporulation (e.g., certain Gram-positive bacteria). As used herein, unless the context makes clear otherwise, "a mutation resulting in a defect in sporulation" or "a genetic mutation that results in a defect in sporulation" refers to any genetic mutation that results in a defect in a member of the sporulation pathway and/or any genetic mutation that prevents the formation of viable spores. For example, non-sporulating bacteria and their creation are described in International Patent Application No. PCT/US2017/013436, incorporated herein by reference.

In some embodiments, sporulation-deficient bacteria are advantageous. An example of a sporulation-deficient bacterium is a spo0A—*Bacillus thuringiensis*. Any mutation or combination of mutations that confers sporulation deficiency but that does not substantially affect viability or heterologous gene expression can be used. These mutations include but are not limited to mutations in the following genes: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. (Silvaggi, J., et al. *Unmasking novel sporulation genes in Bacillus subtilus*. J Bacteriol. 186, 8089-8095, 2004; Sandman, K., et al. *Genetic Analysis of Bacillus subtilis spo Mutations Generated by Tn917-Mediated Insertional Mutagenesis*. Genetics. 117, 603-617, 1987; Malvar and Baum, Tn5401 *Disruption of the spoOF Gene, Identified by Direct Chromosomal Sequencing, Results in CryIIIA Overproduction in Bacillus thuringiensis*. J Bacteriol. 176, 4750-4753, 1994).

In some embodiments, an engineered sporulation deficiency may also render the host bacterium deficient in production in other crystal proteins and other virulence-associated products of sporulation. For example, spo0A—Bt does not produce Cry5B or other endotoxins such as Cry1, Cry4, or Cry8. In some embodiments, the genes of other Cry proteins and/or accessory proteins may be deleted or inactivated to ensure that no additional Cry proteins are used to form the protein crystal.

In such embodiments of sporulation-deficient bacteria, the sporulation-deficient bacteria may be engineered to express a single crystal protein gene such as Cry5B that is under control of a promoter that is actively and/or highly expressed prior to the sporulation phase of a bacterium, e.g., during the vegetative growth or stationary phase. Such engineered bacteria allow for only a single crystal protein to be expressed, and the resulting nematicidal crystals are homogenously comprised of only a single type of crystal protein. In certain embodiments, the promoter is heterologous (i.e., a non-sporulation specific promoter). In one embodiment, the promoter is a Cry3A, GerA, GNAT, or TadA promoter.

In some embodiments, strains of non-sporulating bacteria that autolyse at the end of their growth cycle may be used. Such autolysing bacteria may be used, such that a homogenization step during the purification process may be avoided or reduced.

Bacteria are particularly applicable to the control of STHs because 1) recombinant bacteria can cheaply express large amounts of Cry proteins prior to administration into the GI tract of a mammalian subject, and Cry proteins so expressed, independent of any Cry proteins that may be secreted by bacteria in the GI tract, have been shown to have a significant impact on STHs, 2) studies using purified Cry protein to treat hookworms, whipworms, and *H. bakeri*, all in infected rodents, demonstrate that STHs in the mammalian GI tract can ingest and be killed/intoxicated by Cry proteins, 3) recombinant bacteria expressing a therapeutic protein, in which the protein is not purified, are cheaper to produce since no protein purification steps are needed, and 4) recombinant bacteria delivering STH curing proteins (e.g., Cry5B) are more effective that purified proteins (e.g., Cry5B) at the same bio-active protein dose (e.g., total Cry5B) in curing infections.

Microbes of the disclosed compositions and methods include killed and inactivated forms of *Bacillus* sp., including *Bacillus subtilis* (e.g., *B. subtilis* natto, and *B. subtilis* PY79), *B. cereus*, (e.g., *B. cereus* var. *Toyoi* (*Toyocerin*), *B. cereus* var. *toyoii*), *B. toyonensis*, *B. clausii*, *B. pumilus* and *B. thuringiensis*. *B. subtilis* has been extensively characterized as a safely ingested food additive in humans. In certain exemplary embodiments, killed and inactive forms of *B. thuringiensis* are used.

Other useful bacteria include but are not limited to non-sporulating variants of *Lactococcus* sp., *Bifidobacterium* sp., *Streptococcus* sp., *Clostridium* sp., *Sporolactobacillus* sp, *Sporosarcina* sp., *Brevibacillus* sp, *Leuconostoc* sp., *Pediococcus* sp., *Enterococcus* sp. and *Escherichia* sp. *Lactobacillus* sp. includes but is not limited to *L. lactis*, *L. casei*, *L. paracasei*, *L. acidophilus*, *L. bulgaricus*, *L. delbrueckii* subsp. *bulgaricus*, *L. helveticus*, *L. plantarum*, *L. salivarius*, *L. reuteri*, *L. gasseri*, and *L. animalis*. *Bifidobacterium* sp. includes but is not limited to *B. animalis*, *B. bifidum*, *B. breve*, *B. infantis*, and *B. longum*. *Streptococcus* sp. includes but is not limited to *S. thermophilus*. *Clostridium* sp. includes but is not limited to *Clostridium butyricum*. *Sporolactobacillus* sp. includes but is not limited to *Sporolactobacillus vineae*. *Sporosarcina* sp. includes but is not limited to *Sporosarcina pasteurii*. *Brevibacillus* sp. includes but is not limited to *Brevibacillus laterosporus*.

Still other useful bacteria useful in connection with present disclosure include forms of Gram-negative bacteria. In certain exemplary embodiments, the Gram-negative bacteria include *E. coli* species (e.g., NISSLE 1917) and *Pseudomonas* species (e.g., *Pseudomonas fluorescens*). Exemplary Cry-expressing Gram-negative bacteria which can be killed or inactivated by the methods of the present disclosure include the Cry-expressing *E. coli* strain of Ge et al. ("Hyperexpression of a *Bacillus thuringiensis* delta-endotoxin-encoding gene in *Escherichia coli*: properties of the product", *Gene*, 93: 49-54 (1990)) and the *P. fluorescens* strain of Peng et al. ("A Delta-endotoxin encoded in *Pseudomonas fluorescens* displays a high degree of insecticidal activity", *App. Microbiol Biotech.*, (2003), 63:300-306).

Nematicidal Proteins

As used herein, unless the context makes clear otherwise, "nematicidal protein" refers to any protein that has toxic activity against nematodes or helminthes. Exemplary nematicidal proteins include crystal proteins such as the anthelmintic Cry proteins (e.g., Crickmore et al., 1998 *Microbiology and Molecular Biology Reviews* 62(3): 807-813; Schnepf et al., 1998 *Microbiology and Molecular Biology Reviews* 62(3): 775-806; including but not limited to the *B. thuringiensis* Cry proteins Cry5B (e.g., SEQ ID NO:1) and its subvariants, Cry13A (e.g., SEQ ID NO:2) and its subvariants, Cry14A (e.g., SEQ ID NO:3) and its subvariants, Cry21A (e.g., SEQ ID NOS:4-5) and its subvariants, and Cry6A and its subvariants (e.g., SEQ ID NO:6)) in the bacterium for delivery into a helminth (e.g., roundworm)-infected vertebrate animal gastrointestinal tract via oral dosing (gavage, drinking, eating, pill, capsule, powder, etc.). The Cry proteins are expressed in the cytosol of the bacterium and form crystals, allowing access to the anthelmintic protein after the bacterium lyses or opens up. Nematicidal crystals formed from nematicidal crystal proteins (such as Cry proteins) induce toxicity in worms and helminths by solubilizing or decrystalizing to release the individual nematicidal crystal proteins, thereby allowing the crystal protein to act directly on worms and helminths.

The nematicidal crystals described herein are more stable than the individual crystal proteins of which they are formed, and are resistant to proteolysis. Crystal proteins expressed by bacterium as described herein form crystals of between about 100 kDa and about 170 kDa, between about 110 kDa and about 160 kDa, between about 120 kDa and about 150 kDa, between about 125 kDa and about 145 kDa, or between about 130 kDa and about 140 kDa. These crystal proteins come together to form much larger nematicidal crystals.

Each nematicidal crystal may have a size of about 100 nm, about 200 nm, about 300 nm, about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, or about 2000 nm along its longest axis.

In some embodiments, the nematicidal crystals described herein may be between about 100 nm and about 2000 nm, between about 200 and about 2000 nm, between about 300 nm and about 2000 nm, between about 400 nm and about 2000 nm, between about 500 nm and about 2000 nm, between about 600 nm and about 2000 nm, between about 700 nm and about 2000 nm, between about 800 nm and about 2000 nm, between about 900 nm and about 2000 nm, between about 1000 nm and about 2000 nm along its longest axis.

In some embodiments, the nematicidal crystals described herein may be between about 100 nm and about 1000 nm, between about 200 and about 1000 nm, between about 300 nm and about 1000 nm, between about 400 nm and about 1000 nm, between about 500 nm and about 1000 nm, between about 600 nm and about 1000 nm, between about 700 nm and about 1000 nm, between about 800 nm and about 1000 nm, between about 900 nm and about 1000 nm, between about 1000 nm and about 1000 nm along its longest axis.

In certain embodiments, purified nematicidal crystals formed from a first type of nematicidal crystal protein (e.g. Cry5B) may be combined with nematicidal crystals formed from a second type of nematicidal crystal protein (e.g. Cry5C, Cry5D, Cry6A, Cry13A, Cry14A, Cry21A, Cry 21B, or Cry 55B) in a single pharmaceutical formulation. In such embodiments, a single formulation allows the GI tract to be seeded with multiple forms of purified nematicidal crystals simultaneously. For example, due to the lack of cross-resistance between Cry5B-resistant roundworms and Cry21A-resistant roundworms, simultaneous administration of Cry5B and Cry21A in the gastrointestinal tract may inhibit the development of parasite resistance to the combination therapy.

In the long run, removing antibiotic selection capability (e.g., genetic selection markers) from the plasmids that are used to introduce heterologous Cry protein-encoding sequences, as well as using bacterial strains that are unable to replicate outside the vertebrate host, may be desirable in order to environmentally contain the genetically modified bacteria. For example, LAB (Lactic Acid Bacteria) have been engineered to be autotrophic in thymidine or thymine synthesis such that they can only grow in the vertebrate intestine where thymidine or thymine is present and not in the environment where thymidine or thymine is not present. See, e.g., Steidler L, et al. "Biological containment of genetically modified *Lactococcus lactis* for intestinal delivery of human interleukin 10." Nat Biotechnol 21: 785-789 (2003).

Cry-transformed bacteria such as Bacilli or LAB may be cultured and expression of intracellular, membrane-anchored, or secreted Cry protein by such bacteria may be confirmed using antibodies raised against each Cry protein and standard Western blotting or ELISA techniques.

To assess the bioactivity of all constructs, recombinant bacteria expressing Cry protein (full length, truncated, or variants) may be fed to the free-living nematode, *C. elegans*. Cry protein toxicity on *C. elegans* using LC50, brood-size, developmental inhibition assays on solid media and in liquid wells may then be quantitated. *C. elegans* can access the Cry proteins either via protein secreted onto the solid media/into the liquid well or by their ability to grind, open and digest bacteria. Confirmation that the recombinant bacteria are making bioactive Cry proteins may be obtained. Furthermore, the bioactivity (e.g., $LC_{50}$ in µg/mL) may be quantified and the constructs giving the highest activity determined.

Truncations, Variants, and Sub-variants

The crystal proteins may be truncated to enhance their effectiveness. The usefulness of Bt toxins (e.g., crystal proteins) for controlling STHs may be limited by the protein size that STHs can ingest. Some parasitic roundworms poorly ingest proteins larger than about 40 kDa. Thus, the effectiveness of any particular Bt toxin may be limited by size exclusion of proteins that STHs take in and so should be small enough to be readily absorbed by the STH gut while retaining toxic activity. A truncated toxin may be easier to express in bacteria. Producing a truncated toxin also alleviates the requirement that the target STH has the proper proteases present to correctly process full length protoxin (which is inactive) to a truncated, active toxin form. Thus, a truncated toxin is immediately available for intoxication independent of whether the proper protease processing enzymes are present in the STH target. Truncated toxin may also express at a higher level in microbes because truncated toxins are soluble and less likely to form insoluble inclusions in the cell expressing them, which could be toxic to the cell or which could make the toxin fold incorrectly. Accordingly, it is desirable to produce truncated Bt toxin fragments (e.g., crystal protein fragments). Moreover, fragments of certain Bt toxins have been tested and shown to retain toxic activity and have improved biological properties. By "truncated," when referring to a Bt toxin protein (crystal protein) is meant a Bt toxin protein that is not full-length but retains at least 5%, 10%, 20%, 30%, 40%, 50%, 60%, 70%, 80%, or 90% or more of the toxic activity of a corresponding full-length Bt toxin protein.

"Variants" or "subvariants" of Cry proteins include polypeptides with one or more substitutions, e.g., no more than 20 substitutions, alternatively no more than 10 substitutions, or substitutions at 10% or fewer of the residues, relative to a corresponding wild-type polypeptide or truncated version thereof. The variant, subvariant, or truncated polypeptide has at least 5%, 10%, 20%, 30%, 40%, 50%, 60%, 70%, 80%, or 90% of the activity, e.g., toxic activity, of the corresponding wild-type polypeptide or truncated version. Conservative substitutions include substitutions within the following groups: glycine, alanine, threonine, valine, isoleucine, leucine; aspartic acid, glutamic acid, asparagine, glutamine; serine, cysteine; lysine, arginine; aspartic acid, glutamic acid; serine, threonine; asparagine, glutamine; phenylalanine, tyrosine. One exemplary variant Cry protein is Cry5B with cysteine substituted for serine at position 407 (Ser407Cys) (SEQ ID NO: 7).

Figure 1B:
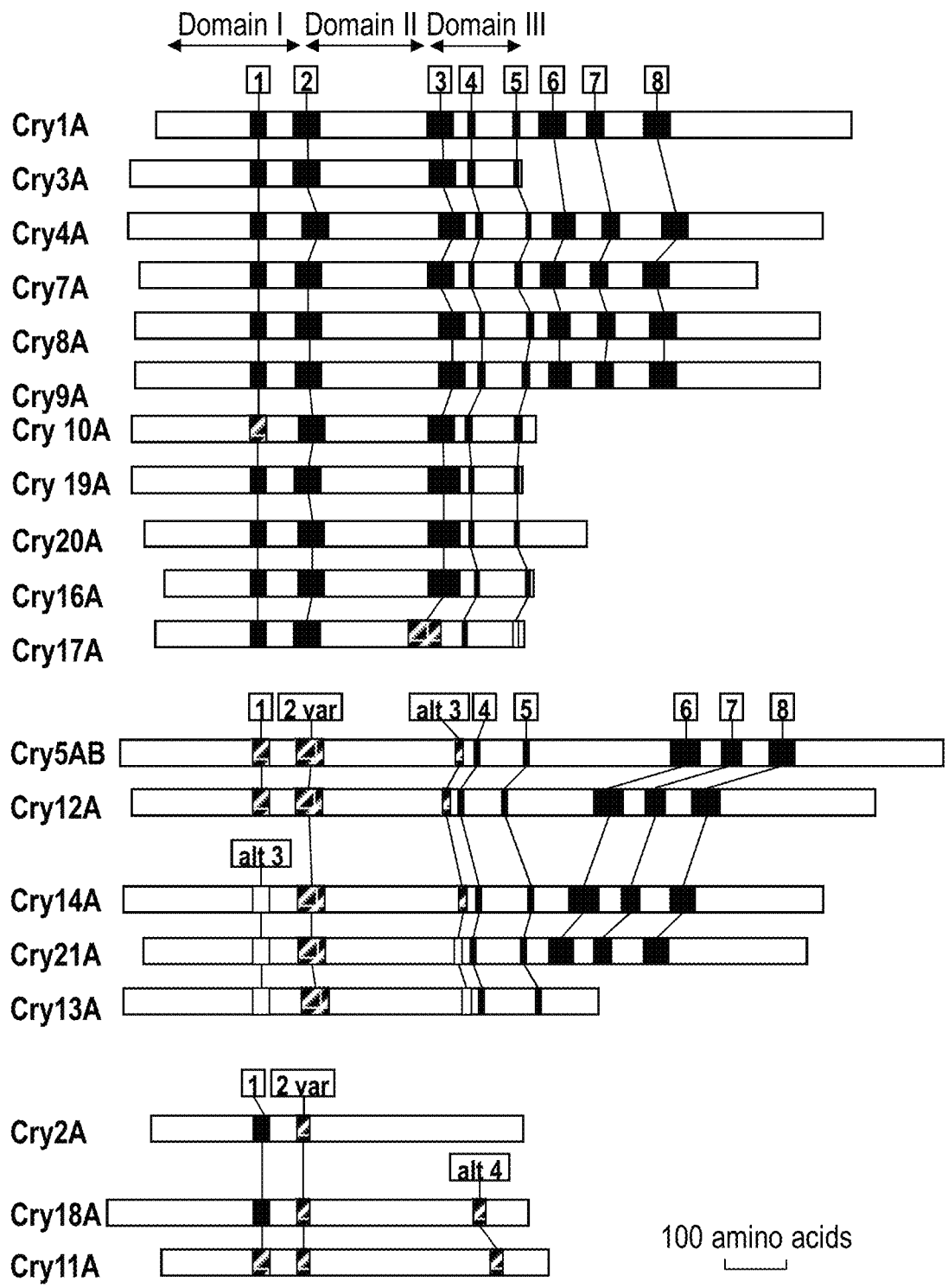

The crystal proteins may be full length, truncated, variants, or subvariants. The truncated crystal protein may include any truncation of the N- and C-termini that still retains toxin activity. The truncated form is not full-length but retains at least 5%, 10%, 20%, 30%, 40%, 50%, 60%, 70%, 80%, or 90% or more of the toxic activity of a corresponding full-length Bt toxin protein. For example, the truncated portion may be truncated between the end of conserved block 5 and the C-terminus of the full-length protein. FIGS. 1A and 1B schematically compare the numbered conserved amino acid blocks (1-5) for a variety of Cry proteins.

In one embodiment, the truncated crystal protein may contain the toxin domain of the crystal protein and optionally include up to 5, 10, or 20 additional amino acids. The truncated crystal protein may be truncated after a conserved amino acid sequence of block 5 and optionally include up to 5, 10, or 20 additional amino acids. The conserved amino acid sequence of block 5 may contain the motif DRIEF (SEQ ID NO: 23), DRLEF (SEQ ID NO: 24), or some other related sequence as well as surrounding amino acid residues, e.g., three amino acids upstream and two amino acids downstream of this motif. Table 1 shows the block 5 sequences for various Cry proteins. See e.g., Schnepf, E., et al., *Bacillus thuringiensis* and Its Pesticidal Crystal Proteins, *Microbiology and Molecular Biology Reviews* 62(3): 775-806, (e.g., at p. 781, FIG. 3) (September 1998); and Crickmore et al., Revision of the Nomenclature for the *Bacillus thuringiensis* Pesticidal Crystal Proteins, *Microbiology and Molecular Biology Reviews* 62(3): 807-813 (September 1998). The truncated crystal protein may also be truncated at the N-terminus. For example, the truncated crystal protein may not contain the first about 1, 2, 3, 4, 5, 6, 7, 8, 9, 10, 15, 20, 25, 30, 35, 40, 45, or 50 amino acids at the N-terminus.

Cry protein variants can exhibit at least 50, 55, 60, 65, 70, 75, 80, 85, 86, 87, 88, 89, 90, 91, 92, 93, 94, 95, 96, 97, 98, or 99 percent amino acid sequence identity to a known Cry protein sequence such as any that are disclosed in Crickmore et al., 1998 *Microbiology and Molecular Biology Reviews* 62(3): 807-813, or in Schnepf et al., 1998 *Microbiology and Molecular Biology Reviews* 62(3): 775-806, including full length Cry proteins and truncated Cry proteins, Cry protein variants or subvariants thereof. Also contemplated according to certain embodiments are polynucleotides encoding such Cry proteins and truncations and variants thereof.

TABLE 1

| Protein | Block 5 Conserved Group |
|---|---|
| Cry1A | VYIDRIEFVP (SEQ ID NO: 7) |
| Cry3A | VYIDKIEFIP (SEQ ID NO: 8) |
| Cry4A | VLIDKIEFLP (SEQ ID NO: 9) |
| Cry5A | VFLDRIEFIP (SEQ ID NO: 10) |
| Cry5B | LFLDRIEFVP (SEQ ID NO: 11) |
| Cry7A | FYVDSIEFIP (SEQ ID NO: 12) |
| Cry8A | VYIDRIEFIP (SEQ ID NO: 13) |
| Cry9A | VYVDRIEFIP (SEQ ID NO: 14) |
| Cry10A | IYIDKIEFIP (SEQ ID NO: 15) |
| Cry12A | MVLDRIEFVP (SEQ ID NO: 16) |
| Cry13A | IYLDRLEFVP (SEQ ID NO: 17) |
| Cry14A | IFIDRIEFIP (SEQ ID NO: 18) |
| Cry19A | LILDKIEFLP (SEQ ID NO: 19) |
| Cry20A | FVLDKIELIP (SEQ ID NO: 20) |
| Cry21A | LFLDRIEFIS (SEQ ID NO: 21) |
| Consensus | i-iDkIEFiP (SEQ ID NO: 22) |

In Table 1, the consensus sequence denotes the positions at which at least 75% of the aligned proteins in the group have an identical or conserved amino acid sequence. An uppercase letter in the sequence indicates that at least 75% of the residues at that position are identical. A lowercase letter indicates that at least 75% of the residues at that position are conserved. Conserved amino acids fall into the following groups: a (A, G, S, T, or P); d (D, E, N, or Q); f (F, W, or Y), I (I, L, M, or V), and k (K or R).

The truncated crystal protein may be a truncated form of Cry5B such as *B. thuringiensis* Cry5B (FIG. 2). Truncated Cry5B may extend from about amino acid 1, 2, 3, 4, 5, 6, 7, 8, 9, 10, 15, 20, 25, 30, 35, 40, 45, or 50 to at least about amino acid 693. The truncated form of Cry5B may optionally include up to an additional 5, 10, 20, 30, 40, or 50 amino acids from the C-terminus after conserved block 5, e.g., through about 698, 703, 713, 723, 733, or 743.

The truncated crystal protein may be a truncated form of Cry13A such as *B. thuringiensis* Cry13A (FIG. 3). Truncated Cry13A may extend from about amino acid 1, 2, 3, 4, 5, 6, 7, 8, 9, 10, 15, 20, 25, 30, 35, 40, 45, or 50 to at least about amino acid 688. The truncated form of Cry13A may optionally include up to an additional 5, 10, 20, 30, 40, or 50 amino acids from the C-terminus after conserved block 5, e.g., through about 693, 698, 708, 718, 728, or 738.

The truncated crystal protein may be a truncated form of *B. thuringiensis* Cry14A (FIG. 4). Truncated Cry14A may extend from about amino acid 1, 2, 3, 4, 5, 6, 7, 8, 9, 10, 15, 20, 25, 30, 35, 40, 45, or 50 to at least about amino acid 675. The truncated form of Cry14A may optionally include up to an additional 5, 10, 20, 30, 40, or 50 amino acids from the C-terminus after conserved block 5, e.g., through about 680, 685, 695, 705, 715, or 725.

The truncated crystal protein may be a truncated form of Cry21A such as *B. thuringiensis* Cry21Aa1 (FIG. 5A) or Cry21Aa2 (FIG. 5B). Truncated Cry21A may extend from about amino acid 1, 2, 3, 4, 5, 6, 7, 8, 9, 10, 15, 20, 25, 30, 35, 40, 45, or 50 to at least about amino acid 685. The truncated form of Cry21A may optionally include up to an additional 5, 10, 20, 30, 40, or 50 amino acids from the C-terminus after conserved block 5, e.g., through about 690, 695, 705, 715, 725, or 735.

Nucleic acid molecules encoding amino acid sequence variants, truncated versions, or both, of a Cry protein are prepared by a variety of methods known in the art. These methods include, but are not limited to, isolation from a natural source (in the case of naturally occurring amino acid sequence variants) or preparation by, for example, oligonucleotide-mediated (or site-directed) mutagenesis, PCR mutagenesis, and cassette mutagenesis of an earlier prepared variant or a non-variant version of protein. Moreover, the present technology includes synthetic nucleic acid molecules where nucleotides are modified to include codons preferred in a particular organism, remove codons rarely used in a particular organism, or remove sequences that may inhibit transcription or RNA processing and the like.

Cry protein truncations may at least include conserved blocks 1-5. As seen in FIGS. 1A and 1B, alignment of known Cry toxins reveals five conserved sequence blocks (blocks 1-5) that are common to a majority of the proteins and are thought to be located in the active toxin domain. See de Maagd, R. A., et al. "How *Bacillus thuringiensis* has evolved specific toxins to colonize the insect world." Trends in Genetics 17(4): 193-99 (April 2001). Comparison of the carboxy-terminal halves of the sequences have suggested the presence of three additional blocks that lie outside of the active toxic core. See Schnepf, E., et al. "*Bacillus thuringiensis* and Its Pesticidal Crystal Proteins." *Microbiology and Molecular Biology Reviews* 62(3): 775-806 (September 1998). Thus, Cry protein truncations may be truncated after the conserved amino acid sequence of block 5 (e.g., DRIEF (SEQ ID NO: 23) or DRLEF (SEQ ID NO: 24)). Alternatively, Cry protein truncations may be truncated after the conserved amino acid sequence of block 5 (e.g., DRIEF (SEQ ID NO: 23) or DRLEF (SEQ ID NO: 24)) plus an additional about 2, 3, 4, 5, 10, 15, 20, 25, 30, 35, 40, 45, or 50 amino acids of the c-terminal domain.

The complete amino acid sequence of Cry5Ba1 is listed in FIG. 2. The conserved amino acid sequence DRIEF (SEQ ID NO: 23) in Cry5B ends at amino acid number 693. Thus, a truncated form of Cry5B may include at least amino acids 50 through about 693. A truncated form of Cry5B may extend from about amino acid 1, 2, 3, 4, 5, 6, 7, 8, 9, 10, 15, 20, 25, 30, 35, 40, 45, or 50 to at least about amino acid 693. Alternatively, or in addition to, a truncated form of Cry5B may include about 5, 10, 15, 20, 25, 30, 35, or 40 additional amino acids of the c-terminal domain.

The complete amino acid sequence of Cry13Aa1 is listed in FIG. 3. The conserved amino acid sequence DRLEF (SEQ ID NO: 24) in Cry13A ends at amino acid number 688. Thus, a truncated form of Cry13A may include at least amino acids 50 through about 688. A truncated form of Cry5B may extend from about amino acid 1, 2, 3, 4, 5, 6, 7, 8, 9, 10, 15, 20, 25, 30, 35, 40, 45, or 50 to at least about amino acid 688. Alternatively, or in addition to, a truncated form of Cry13A may include about 5, 10, 15, 20, 25, 30, 35, or 40 additional amino acids of the c-terminal domain.

The complete amino acid sequence of Cry14Aa1 is listed in FIG. 4. The conserved amino acid sequence DRIEF (SEQ ID NO: 23) in Cry14A ends at amino acid number 675. Thus, a truncated form of Cry14A may include at least amino acids 50 through about 675. A truncated form of Cry5B may extend from about amino acid 1, 2, 3, 4, 5, 6, 7, 8, 9, 10, 15, 20, 25, 30, 35, 40, 45, or 50 to at least about amino acid 675. Alternatively, or in addition to, a truncated form of Cry14A may include about 5, 10, 15, 20, 25, 30, 35, or 40 additional amino acids of the c-terminal domain.

The complete amino acid sequence of Cry21Aa1 and Cry21Aa2 are listed in FIG. 5A and FIG. 5B, respectively. The amino acid sequence of Cry21Aa2 is about 98% identical to the sequence of Cry21Aa1. The conserved amino acid sequence DRIEF (SEQ ID NO: 23) in Cry21A ends at amino acid number 685. Thus, a truncated form of Cry21A may include at least amino acids 50 through about 685. A truncated form of Cry5B may extend from about amino acid 1, 2, 3, 4, 5, 6, 7, 8, 9, 10, 15, 20, 25, 30, 35, 40, 45, or 50 to at least about amino acid 685. Alternatively, or in addition to, a truncated form of Cry21A may include about 5, 10, 15, 20, 25, 30, 35, or 40 additional amino acids of the c-terminal domain.

Anthelmintic Experiments

Once heterologous Cry protein expression and bioactivity are confirmed in a desired bacterium, the modified bacteria may be used for curative-type and preventative-type anthelmintic experiments.

Antibody production: Antibodies against recombinant Cry proteins (e.g., Cry5B, Cry21A, Cry14A, Cry13A, and Cry6A, full length and truncated proteins) may be produced and purified according to standard methodologies (e.g., *Current Protocols in Immunology*, John Wiley & Sons, New York, N.Y. (2009).

Bioactivity tests: To assess the bioactivity of all constructs, recombinant bacilli or other bacteria expressing heterologous Cry proteins are fed to the free-living nematode, *C. elegans*. *C. elegans* can access the Cry proteins either via protein secreted onto the solid media/into the liquid well, by protein naturally released as bacteria break open, or by their ability to grind and digest bacteria to open the bacterial cells.

Rodent and parasite tests: Three intestinal parasitic nematodes—*H. bakeri* (small intestine nematode parasite) in mice, and *Trichuris muris* (whipworm) in mice, and *A. ceylanicum* (hookworm) in hamsters are tested. The tests address: 1) where in the GI tract do heterologous Cry-expressing bacteria reside and for how long; and 2) how do these bacteria affect the acquisition and progression of intestinal nematode parasites.

Parasite tests: Naïve (uninfected) mice are gavaged with the best heterologous Cry-protein expressing recombinant bacterial strain(s) based on expression and bioactivity. Protect against progression test: Mice are infected with *H. bakeri*. Two weeks later, infected mice are treated with heterologous Cry-protein expressing or control bacteria, respectively. Intestinal worm burdens and fecal egg counts are used to determine if the recombinant bacteria provide anthelmintic therapy in mice with pre-existing nematode infections.

Exemplary Parasites

The disclosed methods relate to the control of parasitic worms, e.g., nematodes and platyhelminths, using crystal proteins from *Bacillus* and their derivatives. Parasitic worms within the scope of the invention include but are not limited to those in Class Adenophorea, e.g., Order Mononchida, Family Plectidae, and Order Stichosomida, Family Mermithidae and Tetradonematidae; Class Secernentea, e.g., Order Rhabditida, Family Carabonematidae, Cephalobidae, Chambersiellidae, Heterorhabditidae, Oxyuridae, Panagrolaimidae, Rhabditidae, Steinernematidae, Syrphonematidae, Syrphonematidae, or Thelastomatidae; Order Spirurida, Family Filariidae, Onchocercidae, Physalopteridae, Syngamidae, Spiruridae, Subuluridae, or Thelaziidae; Order Diplogasterida, Family Diplogasteridae; and Order Tylenchida, Family Allantonematidae, Aphelenchidae, Aphelenchoididae, Entaphelenchidae, Fergusobiidae, Phaenopsitylenchidae, Sphaerulariidae, Anguinidae, Dolichodoridae, Belonolaimidae, Pratylenchidae, Hoplolamidae, Heteroderidae, Criconematidae, Tylenchulidae or Tylenehidae. In one embodiment, the parasite is from Class Secernentea, Order Ascaridida, Family Ascarididae; Class Adenophorea, Order Trichurida, Family Trichuridae; Class Secernentea, Order Strongylida, Family Ancylostomatidae (ancylostomidae) or Trichostrongylidae; or Class Secernentea, Order Spirurida, Family Dracunculidae, Filariidae, or Onchocercidae.

The parasite may be a helminth. Helminths within the scope of the invention include but are not limited to those from Phylum Annelida, Class Polychaetae, Class Myzostomida, Class Clitellata, Subclass Hirudinea, Order Gnathobdellidae, Order Rhynchobdellidae; Phylum Platyhelminthes (Flatworms), Class Turbellaria, Class Monogenea, Order Monopisthocotylea, Order Polyopisthocotylea, Class Trematoda, Subclass Aspidogasrea, Subclass Digenea; Super Order Anepitheliocystida, Order Strigeatida, Family Schistosomatidae, Subfamily Schistosomatinae, Genus *Schistosoma*, Order Echinostomatida, Family Fasciolidae, Family Paramphistomatidae, Family Echinostomatidae; Super Order Epitheliocystida, Order Plagiorchiida, Family Dicrocoeliidae, Family Troglotrematidae, Order Opisthorchiida, Family Heterophyidae, Family Opisthorchiidae, Class Cestoda, Subclass Cestodaria, Subclass Eucestoda, Order Pseudophyllidea, Family Diphyllobothriidae, Order Cyclophyllidea, Family Taeniidae, Family Hymenolepididae, Family Dilepididae, Family Mesocestoididae, Order Tetraphyllidea, Order Proteocephalata, or Order Spatheobothridea. For example, Cry proteins with the scope of the invention may be employed to prevent, inhibit or treat Roundworm, Whipworm, Hookworm, Schistosome, or Trematodes.

The parasite may also be gastrointestinal tract parasitic roundworms/nematodes. The gastrointestinal tract parasitic roundworms/nematodes may include but are not limited to the following species: *Haemonochus, Cooperia, Ostertagia, Trichostrongylus, Teladorsagia, Nematodirus, Ancylostoma, Cyathostominea/Cyathostomin/Cyathostome, Strongylus, Parascaris, Ascaris, Trichuris, Oesophagostomum/Oesophagustomum, Trichiuris, Bunostomum, Oxyuris, Chabertia, Habronema, Draschia, Triodontophorus, Toxocara, Toxascaris*, and *Uncinaria*. *Haemonochus* species includes but is not limited to *Haemonchus contortus* and *Haemonchus placei, Cooperia* species includes but is not limited to *Cooperia oncophora, Cooperia pectinata*, and *Cooperia curticei*. *Ostertagia* species includes but is not limited to *Ostertagia ostertagi, Ostertagia (Teladorsagia) circumcincta*, and *Ostertagia trifurcate*. *Trichostrongylus* species includes but is not limited to *Trichostrongylus axei, Trichostrongylus colubriformis*, and *T. circumcincta*. *Teladorsagia* species includes but is not limited to *Teladorsagia (Ostertagia) circumcincta*. *Nematodirus* species includes but is not limited to *Nematodirus spathiger*. *Ancylostoma* species includes but is not limited to *Ancylostoma caninum, Ancylostoma braziliense*, and *Ancylostoma tubaeforme*.

Cyathostominea/Cyathostomin/Cyathostome nematodes are also included. *Strongylus* species (small and large) includes but is not limited to *Strongylus vulgaris, Strongylus equinus*, and *Strongylus edentatus*. *Parascaris* species includes but is not limited to *Parascaris equorum*. *Strongyloides* species includes but is not limited to *Strongyloides westeri*. *Ascaris* species includes but is not limited to *Ascaris suum*. *Trichuris* species includes but is not limited to *Trichuris globulosa, Trichuris suis, Trichuris campanula*, and *Trichuris vulpis*. *Oesophagostomum/Oesophagustomum* species includes but is not limited to *Oesophagustomum dentatum, Oesophagustomum quadrispinulatum, Oesophagostomum columbianum*, and *Oesophagustomum venulosum*. *Trichiuris* species includes but is not limited to *Trichiuris ovis*. *Bunostomum* species includes but is not limited to *Bunostomum trigonocephalum*. *Oxyuris* species includes but is not limited to *Oxyuris equi* (pin worms). *Chabertia* species includes but is not limited to *Chabertia ovina*. *Habronema* species includes but is not limited to *Habronema microstoma* and *Habronema muscae*. *Draschia* species includes but is not limited to *Draschia megastoma*. *Triodontophorus* species includes but is not limited to *Triodontophorus minor* and *Triodontophorus serrates*. *Toxocara* species includes but is not limited to *Toxocara canis* and *Toxocara cati*. *Toxascaris* species includes but is not limited to *Toxascaris leonine*. *Uncinaria* species includes but is not limited to *Uncinaria stenocephala*. Human parasitic roundworms of the gastrointestinal tract include but are not limited to the hookworms *Ancylostoma duodenale* and *Necator americanus*, the whipworm *Trichuris trichiura*, the roundworm *Ascaris lumbricoides*, the threadworm *Strongyloides stercoralis*, and the pinworm *Enterobius vermiculari*.

Additional Therapeutic Agents

In certain embodiments, the pharmaceutical compositions of the invention are administered in combination with at least one additional therapeutic agent. This additional agent can be, for example, a small molecule or a polypeptide (including antibodies and fragments thereof). In a further embodiment, the additional therapeutic is a nicotinic acetylcholine receptor agonist. In certain embodiments, the additional therapeutic agent is administered simultaneously with the pharmaceutical compositions of the invention. In certain embodiments, the additional therapeutic agent is administered sequentially (and in either order) with the pharmaceutical composition. In certain embodiments, the nicotinic acetylcholine receptor agonist is from the levamisole family of nicotinic acetylcholine receptor agonists. In certain embodiments, the nicotinic acetylcholine receptor agonist is levamisole. In certain embodiments, the levamisole is administered in an amount of about 0.1 mg/kg to about 5.0 mg/kg. In certain embodiments, the nicotinic acetylcholine receptor agonist is pyrantel or tribendimidine. In certain embodiments, the pyrantel is administered in an amount of about 1.0 mg/kg to about 15.0 mg/kg. In certain embodiments, the tribendimidine is administered in an amount of about 0.25 mg/kg to about 10 mg/kg.

Administration, Dosage Forms, Pharmaceutical Compositions

The present invention contemplates administration of purified crystal proteins to the gastrointestinal tract of a subject. The pharmaceutical compositions may thus be formulated for oral administration. Oral administration is preferably in an aqueous suspension, emulsion, powder or solid. The composition may be formulated into a food or added to food by the user prior to consumption. Administration to the gastrointestinal tract may also be in the form of an anal suppository (e.g., in a gel or semi-solid formulation). All such formulations are made using standard methodologies.

The methods of treatment disclosed herein are typically practiced on any animal where inhibiting pathogen or parasites is desired. In certain embodiments, the animal is a human. However, the animal can be any livestock or zoological specimen where such inhibition of parasites/pathogens provides economic and health benefits. Any animal can benefit by the claimed methods, including birds, reptiles, mammals such as horses, cows, sheep, goats, pigs, and the like domesticated animals, or any of a variety of animals of zoological interest. Other purposes are readily apparent to one skilled in the arts of nutrient absorption, feed utilization and bioavailability.

The present invention further contemplates a therapeutic system for treating, reducing and/or controlling parasitic infections. Typically, the system is in the form of a package containing a therapeutic composition of the present invention, or in combination with packaging material. The packaging material includes a label or instructions for use of the components of the package. The instructions indicate the contemplated use of the packaged component as described herein for the methods or compositions of the invention. By way of example, and not of limitation, a system can comprise one or more unit dosages of a therapeutic composition according to the present invention. Alternatively, the system can alternately contain bulk quantities of a therapeutic composition. The label contains instructions for using the therapeutic composition in either unit dose or in bulk forms as appropriate, and may also include information regarding storage of the composition, disease indications, dosages, routes and modes of administration and the like information.

Furthermore, depending upon the particular contemplated use, the system may optionally contain either combined or in separate packages one or more of the following components: bifidogenic oligosaccharides, flavorings, carriers, and the like components. One embodiment comprises unit dose packages of purified nematicidal crystal protein for use in combination with a conventional liquid product, together with instructions for combining the purified nematicidal crystal protein with the formula for use in a therapeutic method.

Different dosage regimens may be used in the disclosed methods. In some embodiments, a daily dosage is administered once, twice, three times, or four times a day for one, two, three, four, five, six, seven, eight, nine, or ten days. In some embodiments, a once- or twice-daily dosage is administered every other day.

Administration of the compositions containing the active ingredients effective in inhibiting parasite growth in the intestine and in feces generally consist of one to ten unit dosages of 10 mg to 10 g per dosage of the composition for one day up to one month for a human of approximately 100 kg body weight. Unit dosages are generally given once every twelve hours and up to once every four hours. Preferably two to four dosages of the composition per day, each comprising about 0.1 g to 50 g per dosage, for one to seven days are sufficient to achieve the desired result.

In various specific embodiments, an effective dose of a composition of the present disclosure can be in a range of from about 0.01 mg/kg to about 100 mg/kg for an adult patient, more preferably between about 0.1 mg/kg and about 10 mg/kg of the disclosed composition. Effective doses can be administered to a subject at any suitable frequency, e.g., at least once a week, preferably once a day. Pediatric dosages may be in the range of 15% to 90% of adult dosages.

In other embodiments, a constant dosage of the composition can be administered over time, for example about 2 gm to about 4 gm per day, up to about 6 g to about 10 g per day, depending on the severity of the physiological condition. Once the infection has been effectively ameliorated, the subject can in many instances decrease the dosage to about 2 gm to about 4 gm per day for maintenance purposes. The desired dose may be presented in multiple (e.g., two, three, four, five, six, or more) sub-doses administered at appropriate intervals throughout the day.

The pharmaceutical compositions of the invention can be administered via any of the accepted modes of administration or agents known in the art. However, oral administration is preferred because this route of delivery delivers the purified nematicidal crystal protein to the GI tract. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, and can be in unit dosage forms suitable for simple administration of precise dosages. One exemplary embodiment of the dose form is a capsule containing the composition of the disclosure including the purified nematicidal crystal protein in a dried form, blended with pharmaceutical carrier. The capsule for such a dose form can be of any suitable type, e.g., a gelatin capsule of a conventional variety.

The physiologically compatible carrier medium with which the purified nematicidal crystal proteins are employed, can be of any simple type, e.g., a pharmaceutically acceptable carrier such as fructo-oligo-saccharide (FOS) medium, or other soluble fiber, sugar, nutrient or base material for the composition, with which the bacterial species can be formulated, e.g., in an orally administrable form. Other carrier media include mannitol, inulin (a polysaccharide), polydextrose, arabinogalactan, polyols lactulose, lactitol, etc. A wide variety of materials can be used as carrier material in the practice of the present disclosure, as will be apparent to those of ordinary skill in the art, based on the description herein.

The carrier medium, when present, can be blended with the bacterial species in any suitable amounts, such as an amount of from 5% to 95% by weight of carrier medium, based on the total weight of the bacterial species and the carrier medium, in various embodiments. In other embodiments, the amount of carrier medium may be in a range having a lower limit of any of 5%, 10%, 12%, 15%, 20%, 25%, 28%, 30%, 40%, 50%, 60%, 70% or 75%, and an upper limit, higher than the lower limit, of any of 20%, 22%, 25%, 28%, 30%, 40%, 50%, 60%, 70%, 75%, 80%, 85%, 90%, and 95%. The amount of carrier medium in a specific embodiment may be determined based on considerations of the specific dose form, relative amounts of the purified nematicidal crystal protein, the total weight of the composition including the carrier medium and the bacterial species, and the physical and chemical properties of the carrier medium, and other factors, as known to those of ordinary skill in the probiotic and pharmaceutical formulation art.

In certain embodiments, the purified nematicidal crystal proteins are formulated in a composition that protects the Cry proteins from the acid environment of the stomach. Accordingly, the invention includes a composition containing a purified nematicidal crystal protein and a pharmaceutically-acceptable acid-resistant ("enteric") carrier. By acid-resistant is meant that the carrier or coating does not dissolve in an acidic environment. An acidic environment is characterized by a pH of less than 7. The acid-resistant carrier is resistant to acids at pH less than about 4.0. Preferably, the carrier does not dissolve in pH 2-3. Most preferably, it does not dissolve in pH of less than 2. To purified nematicidal crystal proteins from stomach acids, the purified nematicidal crystal protein are coated or encapsulated with the acid-resistant carrier.

In certain embodiments, the coating is pH-sensitive. For example, the coating may dissolve after the pH is greater than 4.0. For example, the coating dissolves in a neutral environment as is encountered in the small intestine, and does not dissolve in an acidic environment as is encountered in the stomach. Alternatively, the enteric coating dissolves when exposed to specific metabolic event such as an encounter with a digestive enzyme that is found in the small intestine. For example, the coating is digested by a pancreatic enzyme such as trypsin, chymotrypsin, or a pancreatic lipase. The formulation is hydrated in the small intestine. Digestion or dissolution of the coating allows liberation of purified nematicidal crystal proteins, e.g., purified Cry5B, into the intestine.

In other embodiments, purified nematicidal crystal proteins are stabilized in a gel or paste such as an anhydrous carbohydrate paste. In alternate formulations, the purified nematicidal crystal proteins are lyophilized and/or suspended in a gel or paste. Enteric coating materials are known in the art, e.g., malic acid-propane 1,2-diol. Cellulose derivatives, e.g., cellulose acetate phthalate or hydroxypropyl methylcellulose phthalate (HPMCP), are also useful in enteric acid-resistant coatings. Other suitable enteric coatings include cellulose acetate phthalate, polyvinyl acetate phthalate, hydroxypropylmethylcellulose phthalate and anionic polymers of methacrylic acid and methyl methacrylate. Another suitable enteric coating is a water emulsion of ethylacrylate methylacrylic acid copolymer, or hydroxypropyl methyl cellulose acetate succinate (HPMAS). (See, e.g., U.S. Pat. No. 5,591,433). An enteric coating is designed to resist solution in the stomach and to dissolve in the neutral or alkaline intestinal fluid.

In certain embodiments, the purified nematicidal crystal proteins are preferably formed into dry powders. Suitable drying methods include a natural drying, a forced-air drying, a spray drying, a freeze drying, and the like. Of those, a spray drying, drum drying or a forced-air drying are preferably used. A protective agent such as skim milk, sodium glutamate, and saccharides may be used in a time of drying. Saccharides, glucose, and trehalose may be used. In an example of freeze-drying, purified crystal protein may be frozen at −80° C. and then put into a FreeZone 1 Liter Benchtop Freeze Dry System (Labconco catalog number 7740020). The condenser is set to −60° C. and the vacuum is set at 22 mTor. The samples are freeze-dried overnight. In an example of spray-drying, a PCC sample at 10% solids w/v is spray dried using a Yamato Pulvis GB22 (or any other spray drying system) through a 100 micron atomizer nozzle at 5 mLs/min with atomizing air set at 1 Kgf/m$^2$, drying air set at 0.21 m$^3$/min, inlet/outlet temperatures set at 98° C./59° C., respectively.

Auxiliary and adjuvant agents may include, for example, preserving, wetting, suspending, sweetening, flavoring, perfuming, emulsifying, and dispensing agents. Prevention of the action of contaminating microorganisms, if desired, can be accomplished using various antibacterial and antifungal agents, such as, parabens, chlorobutanol, phenol, sorbic acid, and the like. Isotonic agents, such as sugars, sodium chloride, and the like, may also be included.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the active agent (such as the purified nematicidal crystal protein), and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Actual methods of preparing such dosage forms are known, or will be apparent, to those skilled in this art. Reference is made, for example, to Remington's Pharmaceutical Sciences, 18th ed. (Mack Publishing Company, Easton, Pa., 1990).

Methods

The methods are directed to treating a parasitic worm or helminth infection in a subject comprising administering to the subject a therapeutically effective amount of a composition comprising isolated native, bioactive nematicidal crystals formed from a single type of nematicidal crystal protein. The pharmaceutical composition is substantially free of any bacterial spores or host bacterial proteins other than nematicidal crystal protein in the form of a crystal.

The methods are also directed to reducing the severity of a parasitic worm or helminth infection comprising administering to the subject a therapeutically effective amount of a pharmaceutical composition comprising isolated native, bioactive nematicidal crystals formed from a single type of nematicidal crystal protein, wherein the pharmaceutical composition is substantially free of any bacterial spores or host bacterial proteins other than nematicidal crystal protein in the form of a crystal.

Selected Definitions

As used herein, unless the context makes clear otherwise, "treatment," and similar words such as "treated," "treating" etc., indicates an approach for obtaining beneficial or desired results, including and preferably clinically desirable results. Treatment can involve optionally either the amelioration of symptoms of the disease or condition, or the delaying of the progression of the disease or condition.

As used herein, unless the context makes clear otherwise, "subject" means a vertebrate, such as a mammal. The mammal can be a feline, a rodent, a canine, a bovine, an equine, a swine, a caprine, an ovine, or a primate. In some embodiments, the subject is a human.

As used herein, unless the context makes clear otherwise, "reducing the likelihood of occurrence," "prevention," and similar words such as "prevented," "preventing" etc., include approaches for preventing, inhibiting, or decreasing the likelihood of the onset or recurrence of a disease or condition, in a manner that exhibits statistical significance, for example, when compared to the results obtained when the indicated method steps are omitted. Similarly, also included are preventing, inhibiting, or decreasing the likelihood of the occurrence or recurrence of the symptoms of a disease or condition, or optionally delaying the onset or recurrence of a disease or condition, or delaying the occurrence or recurrence of the symptoms of a disease or condition. As used herein, "prevention" and similar words also include reducing the intensity, effect, symptoms and/or burden of a disease or condition prior to onset or recurrence of the disease or condition. Methods according to these and related embodiments may be practiced using an effective amount or a therapeutically effective amount of an agent that substantially eradicates, reduces the severity of, or reduces the likelihood of occurrence of a soil-transmitted helminth (STH) infection. As used herein, an "effective amount" or a "therapeutically effective amount" of a composition, agent or substance is that amount sufficient to obtain a desired biological effect, such as beneficial results, including clinical results.

As used herein, unless the context makes clear otherwise, "food grade oil" includes oils suitable for ingestion by humans or animals. Exemplary food grade oils include, but are not limited to, oils extracted from vegetables, such as corn oil, soybean oil, coconut oil, cottonseed oil, olive oil, palm oil, peanut oil, rapeseed or canola oil, safflower oil, sunflower oil. Food grade oil includes, but is not limited to, nut oils, e.g. almond oil, beech nut oil, brazil nut oil, cashew oil, hazelnut oil, macadamia nut oil, mongongo nut oil, pecan oil, pine nut oil, pistachio oil, walnut oil, and pumpkin seed oil. Food grade oils include oils from citrus, fruit, melons and gourd seeds, or any edible plant.

In certain preferred embodiments, the compositions described herein for treating or reducing the severity or likelihood of occurrence of an STH infection are formulated as pharmaceutical compositions, which will preferably be formulated for oral delivery. Pharmaceutical compositions are formulated so as to allow the agent(s) contained therein to be bioavailable upon administration of the composition to a human.

It will be appreciated that the practice of the several embodiments of the present invention will use, unless indicated specifically to the contrary, conventional methods in virology, immunology, microbiology, molecular biology and recombinant DNA techniques that are within the skill of the art, and many of which are described below for the purpose of illustration. Such techniques are explained fully in the literature. See, e.g., *Current Protocols in Molecular Biology or Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

As used herein, the terms "pure" and "purity" in combination with a number (e.g. 95% pure) refer to compounds and substances of the instant disclosure being present in weight/weight amount relative to other compounds and substances. For example, a composition that is 95% pure nematicidal crystal means that 95% of the composition (weight/weight) is nematicidal crystal protein and 5% of the composition (w/w) comprises one or more other substances.

As used herein, the phrase "crystal content" in combination with a percentage (e.g. 95% crystal content) refers to nematicidal crystals of the instant disclosure being present in a composition in the percentage of the total weight of the compositions. In certain embodiments, the compositions of the invention have at least 80%, at least 90%, or at least 95% (e.g., 95%, 96%, 97%, 98%, 99% or 100% crystal content.

As used herein, the term "substantially free of" in reference to a composition or compound (e.g. a compound substantially free of spores) means that the composition or compound contains less than or equal to 5% w/w of another substance (e.g. the compound has less than or equal to 5%, 2%, 1%, 0.5%, 0.1%, 0.01%, 0.001% or 0.0001% w/w of spores).

As used in this specification and the appended claims, the singular forms "a," "an" and "the" include plural references unless the content clearly dictates otherwise. Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Each embodiment in this specification is to be applied mutatis mutandis to every other embodiment unless expressly stated otherwise.

As used herein, the term "about" in quantitative terms refers to plus or minus 5% of the value it modifies (rounded up to the nearest whole number if the value is not subdividable, such as a number of molecules, nucleotides, or amino acids). For example, "about 20%" would encompass 15-20% and "about 80%" would encompass 75-85%, inclusive. Moreover, where "about" is used herein in conjunction with a quantitative term it is understood that in addition to the value plus or minus 5%, the exact value of the quantitative term is also contemplated and described. For example, the term "about 23%" expressly contemplates, describes, and includes exactly 23%.

EXAMPLES

The following Examples are presented by way of illustration and not limitation.

Example 1: Creation of IBaCC

For production of Cry5B in sporulation-defective cells, *B. thuringiensis* (Bt) strain 4D8 which lacks any crystal protein expressing (Identification of *Bacillus thuringiensis* subsp. kurstaki strain HD1-Like bacteria from environmental and human samples after aerial spraying of Victoria, British Columbia, Canada, with Foray 48B. Appl Environ Microbiol. 2001 March; 67(3):1035-43) and in which the master spo0A regulator of sporulation (spo0A–) was deleted by homologous recombination. This composition is further referred to as Cry5B-BaCC (*Bacillus* with Cytosolic Crystal).

To inactivate Cry5B-BaCC, the transformed *B. thuringiensis* 4D8 strain was propagated aerobically in 200 mL volume in 2 liter baffled flasks with shaking at 30° C. in three-fold concentrated Luria-Bertani broth (LB) supplemented with 10 µg/mL erythromycin and 200 g/mL kanamycin for 48 hours. The transformed *B. thuringiensis* cells were spun down at 4500 rpm for one hour at 4° C. and resuspended to 14 of the original cell culture volume with prechilled sterile double-distilled water, and then were treated with 1 mg/mL carvacrol (a food-grade antimicrobial) for 15 min with shaking at 4° C. The carvacrol-treated cells were spun down and washed three times with prechilled sterile double-distilled water. Final pellets were concentrated 40 times and were stored at –80° C. until use. The dead BaCC containing biologically active Cry5B crystals are termed IBaCC (Inactivated *Bacillus* with Cytosolic Crystal). The 4D8 strain is also capable of autolysis, naturally lysing at the end of the growth cycle and releasing the crystal. Killing with carvacrol and homogenization can still be used to kill any residual cells and break open any residual intact IBaCC.

Example 2: Purification of Cry5B from IBaCC Using Homogenization

Figure 6:
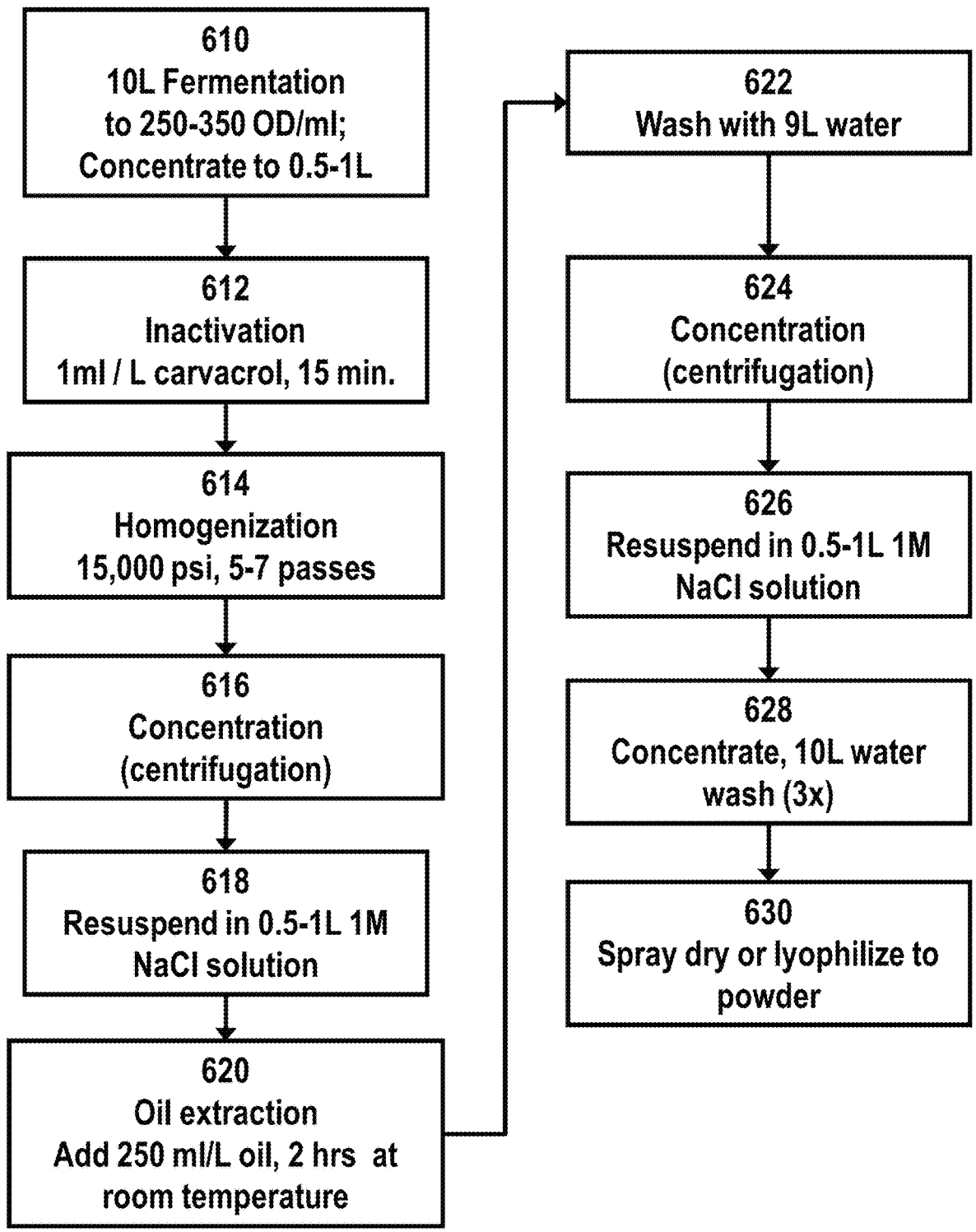
FIG. 6 is a flow chart showing the steps for purifying nematicidal crystal protein from inactivated BaCC (IBaCC).

FIG. 6 shows a flow chart of the process used to purify Cry5B crystal protein from IBaCC. To purify large amounts of Cry5B protein from IBaCC, a 10 L fermentation harvest was undertaken (FIG. 6, step 610). Ten liters of BaCC were grown to between 250-350 OD/ml. The BaCC was then concentrated to between 0.5 L and 1 L using centrifugation (8000×g, 30 minutes), and then inactivated by adding 1 ml/L carvacrol and stirring for 15 minutes at room temperature (step 612) to produce IBaCC. Other methods of concentrating the BaCC prior to the inactivation step may be used, such as ultrafiltration or diafiltration.

The IBaCC was homogenized at 15,000 psi for 5 to 7 passes (step 614), and the resulting lysate was centrifuged to concentrate the bacterial lysate (step 616). Other methods of concentrating the IBaCC may be used, such as ultrafiltration or diafiltration. The resulting pellet was resuspended in 0.5 L to 1 L of 1M NaCl solution (step 618). The concentrated lysate was then mixed with 250 ml/L oil for two hours at room temperature to extract the carvacol (step 620). Following the oil extraction, 9 L of water was then added (step 622), and the mixture was again concentrated (step 624) by centrifugation. The concentrated pellet was then resuspended in 0.5 L to 1 L of NaCl solution (step 626). The mixture was then washed three times with 10 L water and concentrated (step 628) by centrifugation (8000×g, 30 minutes). The resulting composition is a purified Cry5B crystal (PCC). In some embodiments, the composition may be spray-dried or lyophilized (step 630).

Figure 7:
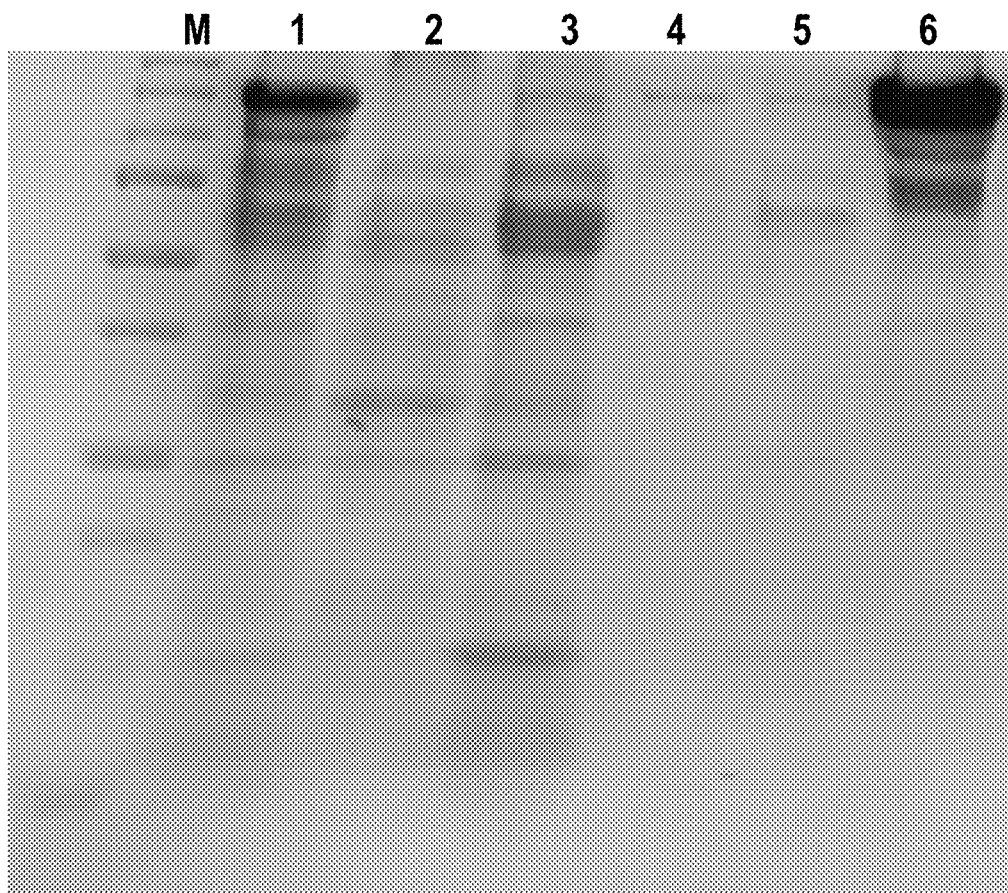
FIG. 7 is a picture of a protein gel with samples from several steps of the purifying process for Cry5B PCC.

FIG. 7 shows a protein gel with samples from various stages of the purification process. Lane 1 of the gel is 5 µL of homogenized IBaCC after being grown to 200 nm OD. Lane 2 is a 15 µL sample of supernatant from concentrated homogenized IBaCC. Lane 3 is a 15 µL sample of a water layer following washing of the oil-extracted IBaCC lysate. Lane 4 is a 15 µL sample of the 1M NaCl wash (step 626). Lane 5 is a 15 µL sample of a phosphate buffered saline wash of pelleted IBaCC. Lane 6 is a 15 µL sample of PCC following step 628 (from another batch of BaCC grown to an OD of 312 Absorbance 600 units).

Figure 8:
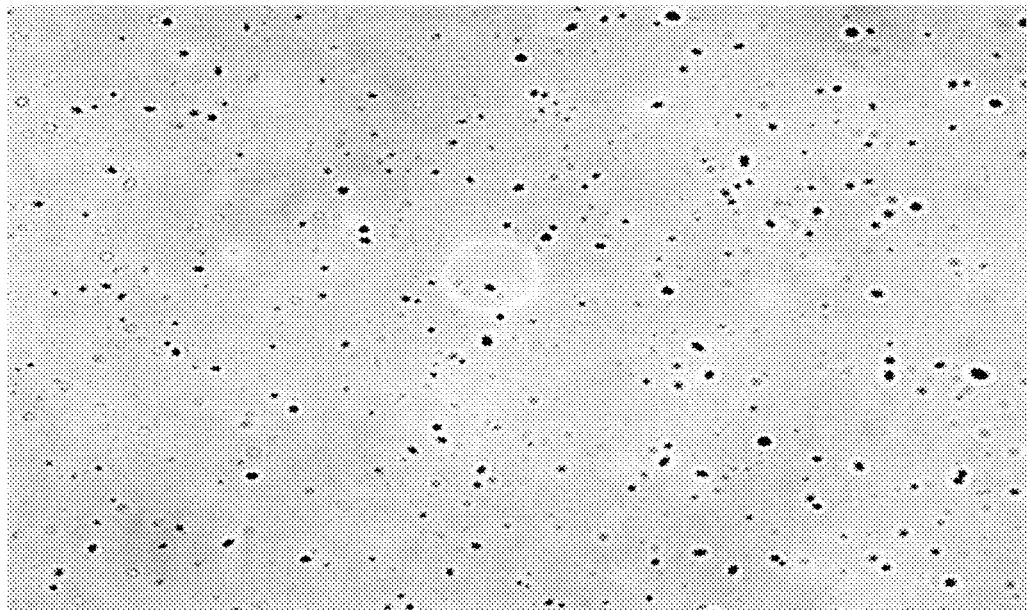
FIG. 8 is a phase-contrast photomicrograph of Cry5B PCC at 1000× magnification.

FIG. 8 is a phase-contrast photomicrograph of PCC particles at 1000× magnification.

Example 3: Purification of Cry5B from Autolyzed IBaCC

Some strains of BaCC, such as strain 4D8, autolyse at the end of their growth cycle. This autolysis can obviate or reduce the need for a homogenization step following inactivation with an antimicrobial compound. Thus, referring to purification flow chart of FIG. 6, the homogenization step 614 may be eliminated or the number of passes reduced if an autolysing strain of bacteria is used. In such embodiments, a 10 L fermentation harvest of an autolysing BaCC may be undertaken (FIG. 6, step 610). Ten liters of BaCC may be grown to between 250-350 OD/ml. The BaCC may then be concentrated to between 0.5 L and 1 L using centrifugation, and then inactivated by adding 1 ml/L carvacrol and stirring for 15 minutes at room temperature (step 612) to produce IBaCC. Since the IBaCC have autolysed before and/or after inactivation, homogenization was not necessary. Other methods of concentrating the BaCC prior to the inactivation step may be used, such as ultrafiltration or diafiltration.

The lysate from the autolysed IBaCC may then be concentrated by centrifugation, ultrafiltration, or diafiltration (step 616). The resulting pellet may then be resuspended in 0.5 L to 1 L of 1M NaCl solution (step 618). The concentrated lysate may then be mixed with 250 ml/L oil for two hours at room temperature to extract the carvacol (step 620). Following the oil extraction, 9 L of water may then be added (step 622), and the mixture may be concentrated again (step 624) by centrifugation, ultrafiltration, or diafiltration. The concentrated mixture may then be resuspended in 0.5 L to 1 L of NaCl solution (step 626). The mixture may then be washed three times with 10 L water and concentrated (step 628) by centrifugation, ultrafiltration, or diafiltration. The resulting composition will be a purified Cry5B crystal (PCC). In some embodiments, the composition may then be spray-dried or lyophilized (step 630).

Example 4: PCC Intoxicates Whipworms In Vitro

Figure 9A:
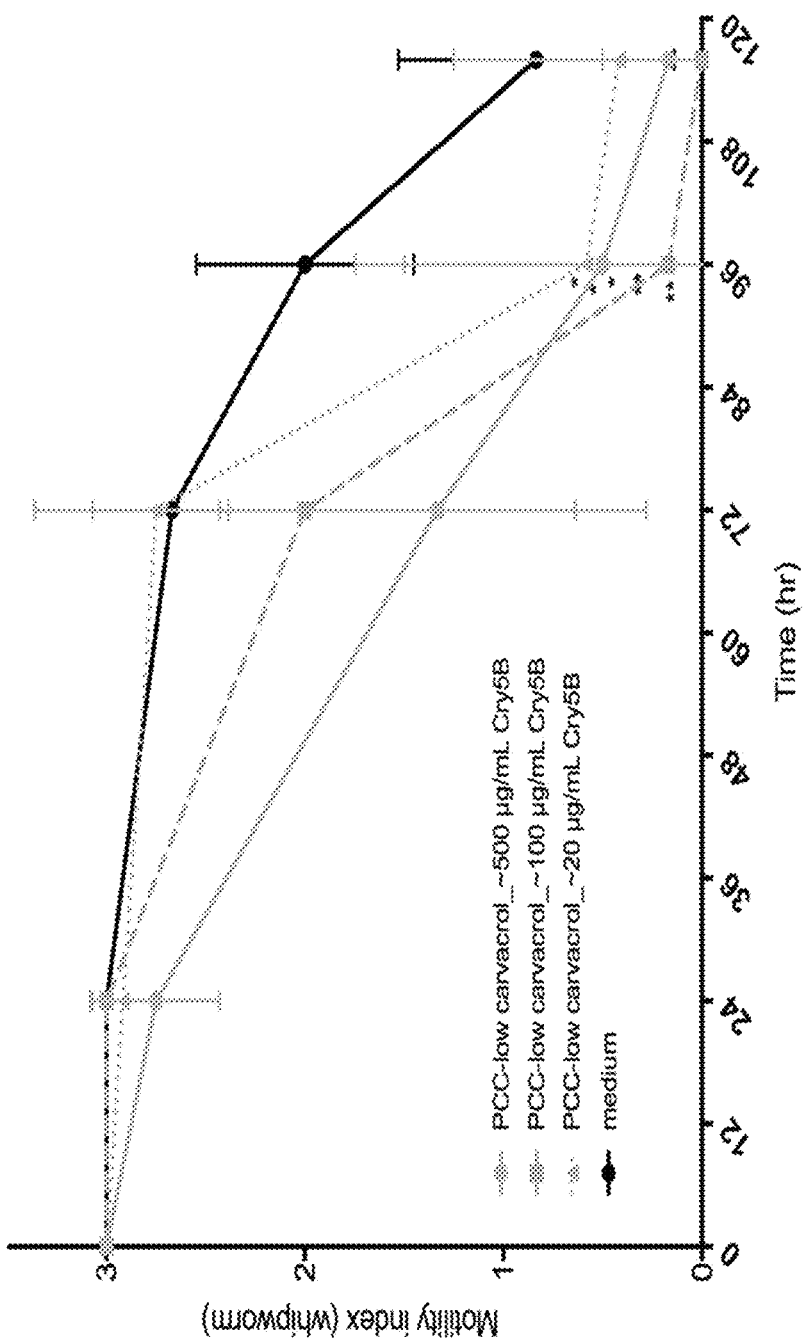
FIG. 9A shows a graph of changes in whipworm motility over time following in vitro exposure to doses of Cry5B PCC.
Figure 9B:
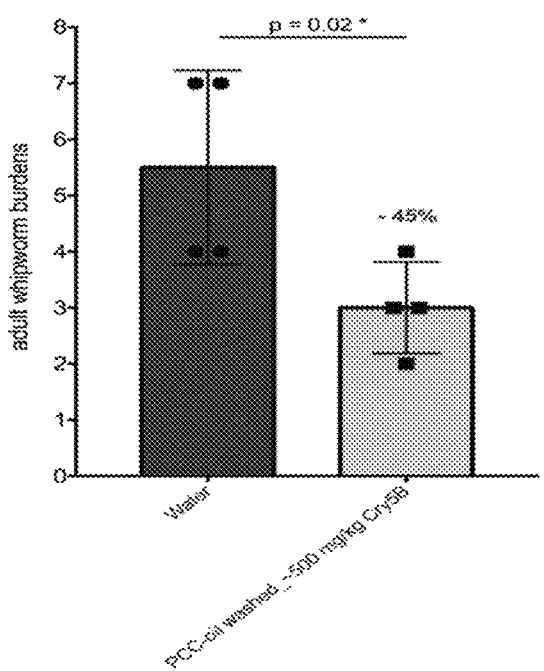
FIG. 9B shows a bar histogram of in vivo whipworm burdens in hamsters treated with Cry5B PCC and water control.
Figure 10A:
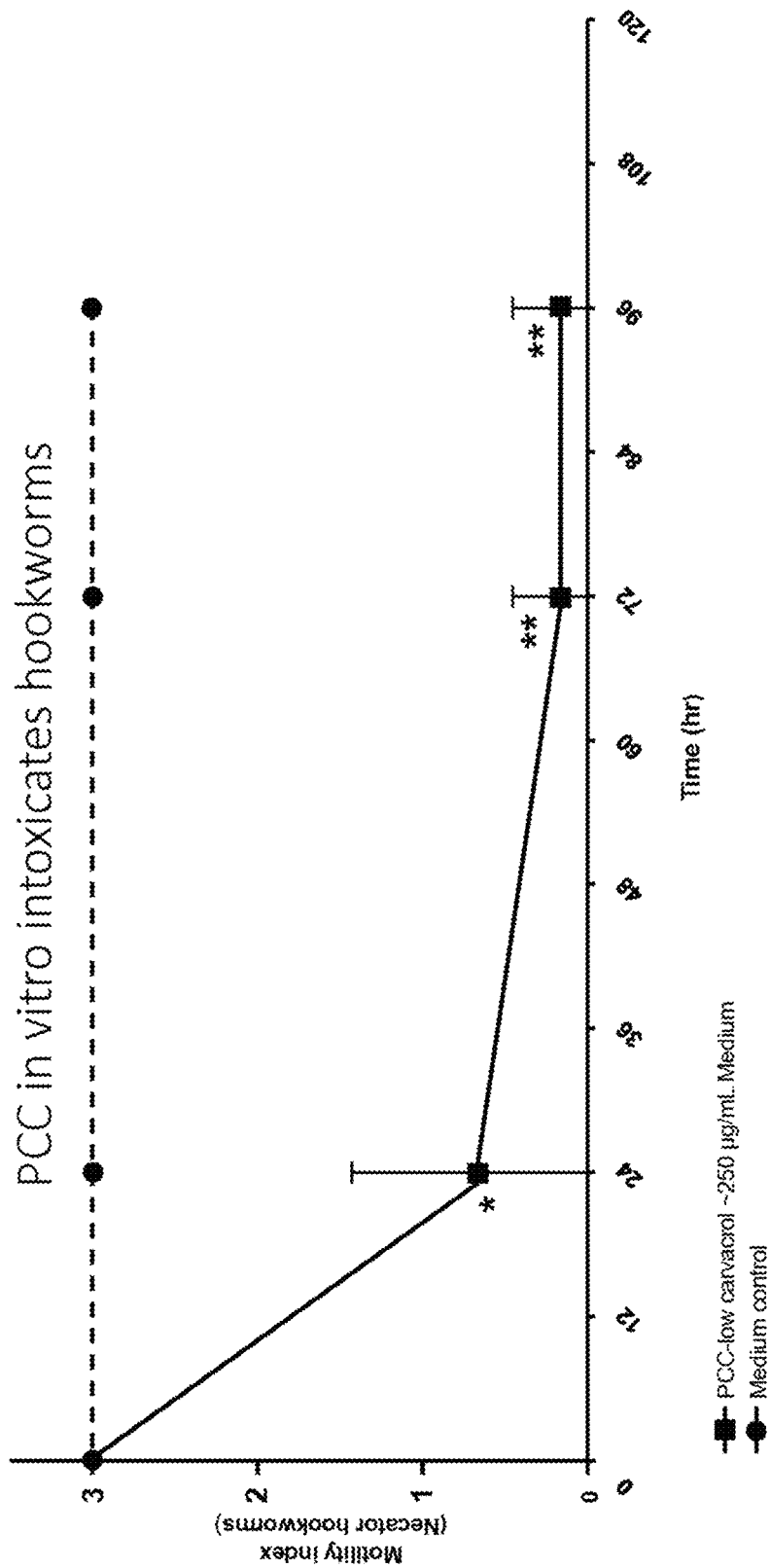
FIG. 10A shows a graph of changes in hookworm motility over time following in vitro exposure to doses of Cry5B PCC.
Figure 10B:
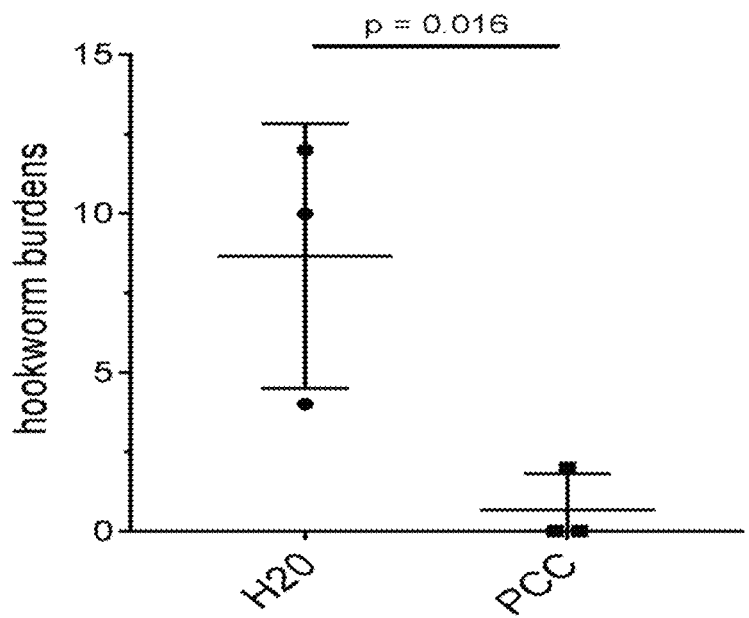
FIG. 10B shows a histogram of hookworm burdens in hamsters treated with Cry5B PCC and water control.
Figure 10C:
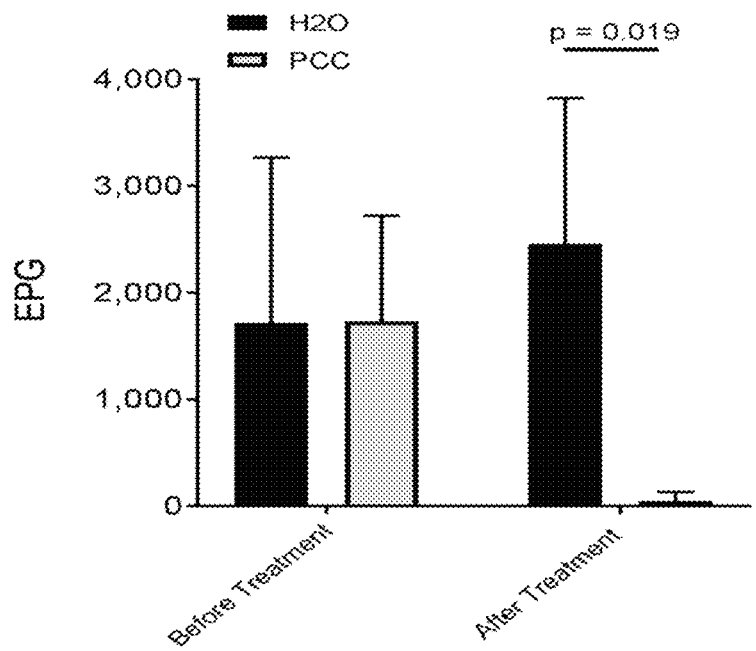
FIG. 10C shows a bar histogram of hookworm burdens in hamsters before and after treatment with Cry5B PCC and water control.
Figure 11A:
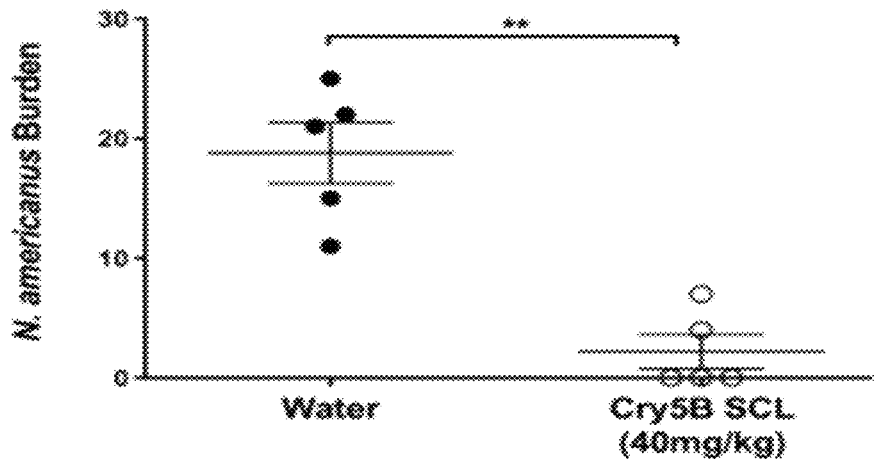
FIG. 11A shows a plot of hookworm burden in hamsters following treatment with either Cry5B spore-crystal lysate (SCL) or water control.
Figure 11B:
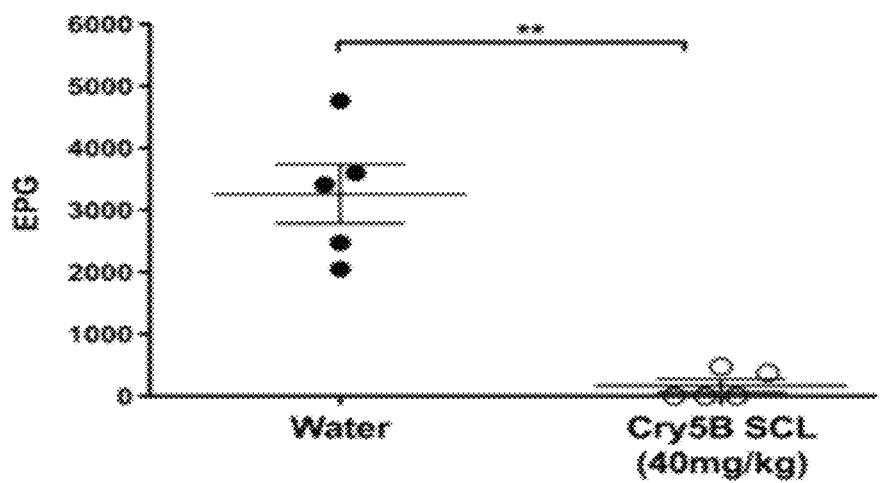
FIG. 11B shows a plot of eggs per gram in hamsters following treatment with either SCL or water control.
Figure 12:
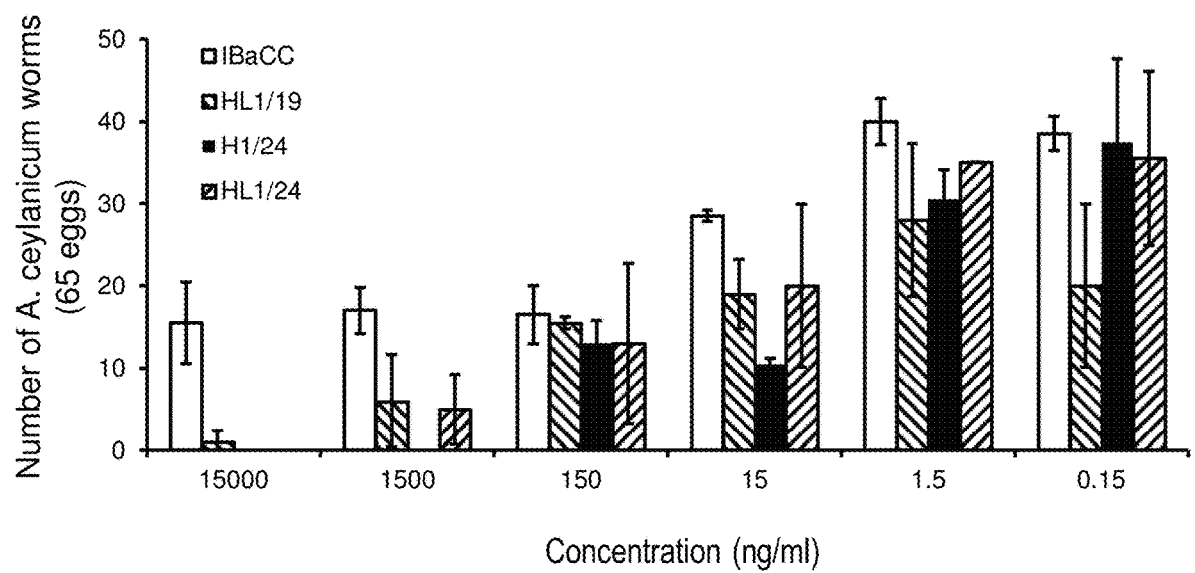
FIG. 12 shows a bar histogram of various concentrations of Cry5B PCC toxicity on *Ancyclostoma ceylanicum* hookworm eggs; some of the Cry5B PCC was treated by the addition of lysozyme.
Figure 13A:
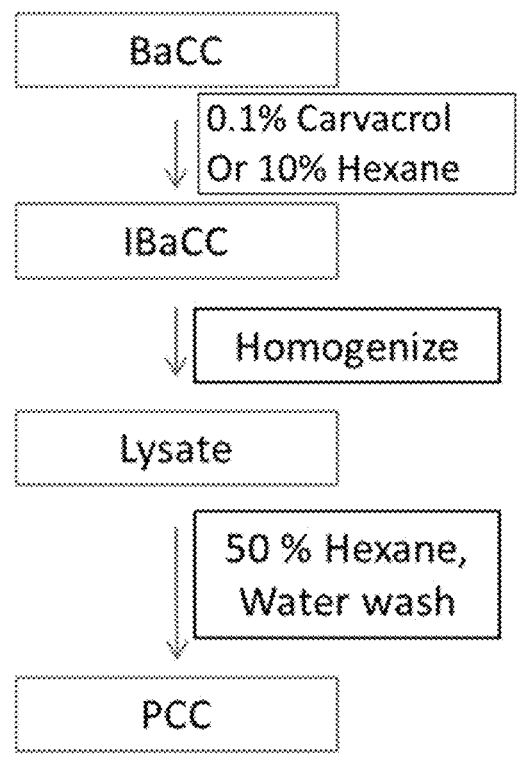
FIG. 13A shows a schematic diagram of the protocol for the purification of PCC from BaCC.
Figure 13B:
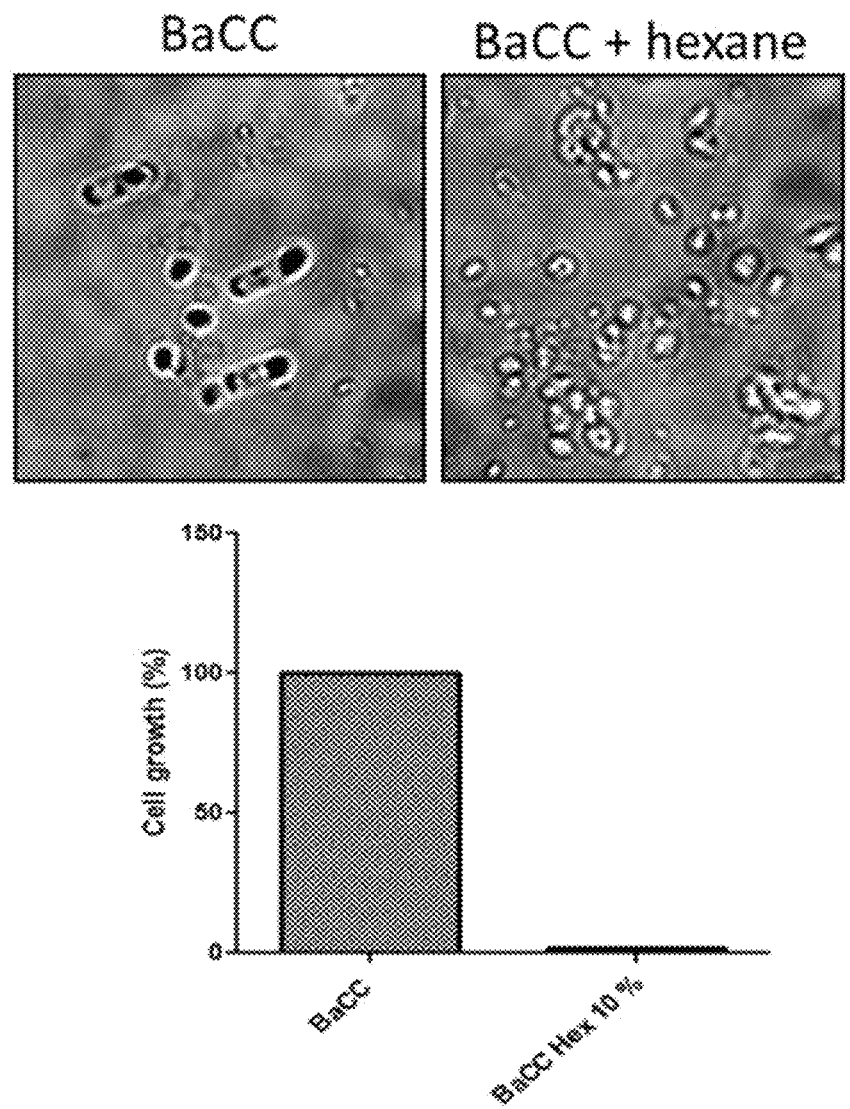
FIG. 13B shows microscopic images of BaCC before and after 10% hexane treatment (top panel), and a bar diagram depicting the percentage of cell growth (measured using OD600) of BaCC before and after 10% hexane treatment (bottom panel).
Figure 13C:
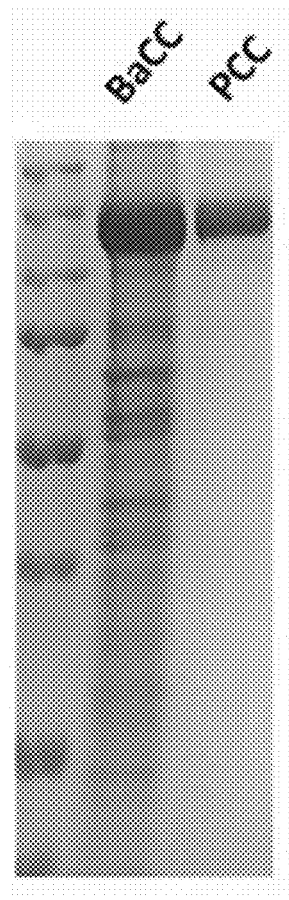
FIG. 13C shows an image of an SDS-PAGE gel depicting the starting BaCC material and the final purified PCC product.

Whipworm mobility in vitro was examined following treatment with PCC made as described in Example 2. Three whipworms were added per well in RPMI medium with antibiotics, 4 wells per dose, and doses of 20, 100, and 500 µg/ml of PCC (Cry5B). FIG. 9A shows a graph of the dose-dependent effect of PCC (Cry5B) on whipworm motility measured at the times indicated. The data is expressed as the average motility index per well, where 3=highly motile, 2=slowly motile, 1=immotile unless touched, 0=immotile even when touched.

Example 5: PCC Reduces Whipworm Burdens In Vivo

The ability of PCC to reduce whipworm burdens in hamsters was examined. Mice were infected with whipworms, *Trichuris muris*. Mice were split into two groups (4 mice per group), water and PCC-oil washed at ~500 mg/kg of Cry5B made as described in Example 2. Both groups were administered water and PCC-oil washed via gavage in 0.5 ml volumes, single dose. Pre-treatment fecal egg counts were measured at day 34 post-infection to place the mice into two groups of equivalent fecal egg counts. Mice were treated by gavage day 35 post-infection. Post-treatment evaluation was conducted on day 41 post-infection (6 days after treatment) in which all mice were opened up and total whipworm counts taken (cecum). There was a 45% reduction in whipworm burdens (average of 5.5 whipworms in water; average of 3 whipworms in PCC), p=0.02.

FIG. 9B shows a histogram of this experiment, comparing whipworm burdens of hamsters treated with water (control) and hamsters treated with 500 mg/kg PCC made as described in Example 2.

Example 6: PCC Intoxicates Hookworms In Vitro

Hookworm (*Necator americanus*) mobility in vitro was examined following treatment with PCC made as described in Example 2. Three hookworms were added per well, 4 wells per dose, at a dose of 250 μg/ml. FIG. 10A shows a graph of changes in hookworm motility over time following in vitro exposure to doses of Cry5B PCC. PCC had a dose-dependent effect on hookworm intoxication. The data is expressed as the average motility index per well, where 3=highly motile, 2=slowly motile, 1=immotile unless touched, 0=immotile even when touched.

Example 7: PCC Reduces Hookworm Burdens In Vivo

PCC was used at a dose of 10 mg/kg to treat hamsters infected with hookworm *Necator americanus*. Six hamsters were infected with *N. americanus* and kept on a regimen of immunosuppression (dexamethasone in the drinking water and twice weekly injections) for the entire duration of the experiment in order to prevent expulsion of the parasites. Following inoculation (approximately 60 days later) three hamsters were treated per os with a single dose of 10 mg/kg of PCC and three hamsters were treated with water as a control. Fecal egg counts were collected before treatment to determine worm loadings and hamsters were grouped into two groups of equivalent fecal egg counts prior to treatment. At 5 days post-treatment, animals were sacrificed and intestinal worm burdens determined.

FIG. 10B shows a histogram of hookworm burdens in hamsters treated with Cry5B PCC and water control. FIG. 10C shows a bar histogram of hookworm fecal egg counts in hamsters before and after treatment with Cry5B PCC and water control. A single PCC dose of 10 mg/kg resulted in a 92% drop in hookworm burden (P=0.016), and a 98% drop in fecal egg count (FEC; P=0.0-19).

In contrast, Cry5B spore-containing lysate (SCL) requires four times the dose to achieve equivalent hookworm burden reduction in hamsters. Hamsters infected with hookworm *Necator americanus* and treated with a single 40 mg/kg dose of Cry5B. FIG. 11A shows a plot of hookworm burden in hamsters following treatment with either Cry5B SCL per os or water control. FIG. 11B shows a plot of eggs per gram in hamsters following treatment with either Cry5B SCL or water control. The single dose of 40 mg/kg Cry5B SCL resulted in an 88% drop in hookworm burden and a 95% drop in fecal egg count.

Example 8: PCC is an Effective Toxin Against Hookworm Eggs

FIG. 12 shows a bar histogram of various concentrations of Cry5B PCC (three preparations) toxicity on *Ancyclostoma ceylanicum* hookworm egg-to-larval development compared to Cry5B IBaCC. Some of the Cry5B PCC was treated by the addition of lysozyme, which did not appear to affect the toxicity of the Cry5B PCC. *A. ceylanicum* eggs (~65/well with multiple wells/dose) were placed in buffer with an *E. coli* food source and allowed to develop 7 days at 25 C. The number of eggs that hatch and develop to the third larval infectious stage is noted at day 7. PCC is able to inhibit development of this hookworm even at low concentrations (with an $IC_{50}$ of ~15 ng/mL) and with higher activity than IBaCC.

Example 9: Improved Method for Purification of Purified PCC from BaCC

*B. thuringiensis* expressing Cry5B was fermented as described in Example 1, i.e., (BaCC) at the 10 L scale (Step 631) (FIG. 13A). After 10-fold cell concentration by centrifugation (4,500 rpm, 60 min at 4° C.) (Step 632), the washed BaCC was suspended in 500 ml water (final volume) and hexane was added to 10% v/v final concentration and mixed in a sealed vessel for 1 hour at room temperature to prepare IBaCC (Step 633). FIG. 13B shows microscopic images illustrating the production of IBaCC from BaCC. The microscopic image on the left shows the BaCC, and the microscopic image on the right shows the effect of hexane on BaCC, with the rod-structure destroyed. The bar graph of FIG. 13B shows the quantification of the percentage cell growth of BaCC (100% cell growth) and BaCC treated with 10% hexane (0% cell growth, complete inactivation). FIG. 13C shows an image of an SDS-PAGE gel, depicting the starting BaCC material and the final purified PCC product, following the process depicted in the diagram of FIG. 13A. Other methods of cell inactivation, e.g., surfactants, microbicides, biocides, etc., can substitute for hexane.

Purified Cry5B Crystals (PCC) were produced from IBaCC as described in Example 2. Briefly, IBaCC was homogenized at 15,000 psi for 5 to 7 passes to lyse the cells, releasing the PCC from the IBaCC cell wall ghosts (Step 634).

To purify the PCC by phase-portioning from the soluble cell components, lipids, and cell wall debris, hexane was added to 50% v/v and mixed vigorously in a sealed vessel for 1 hour at room temperature. The emulsion was transferred to sealed bottles and centrifuged at 4,500 rpm for 1 hour at 4° C. (Step 635) The upper hexane layer was collected and transferred to solvent waste. The interface layer containing cell wall debris was removed and discarded.

The aqueous layer containing water-soluble cellular constituents was removed and discarded, and the PCC in the pellet was retained. Following water washing the PCC pellets were stored frozen. The resulting PCC had 98% protein w/w. Other methods of PCC recovery, such as continuous centrifugation to collect the PCC in the aqueous phase and the hexane and interface in the supernatant phase are possible. The final PCC can be stored frozen or lyophilized or spray dried and stored at room-temperature, 4° C., or frozen.

Figure 14:
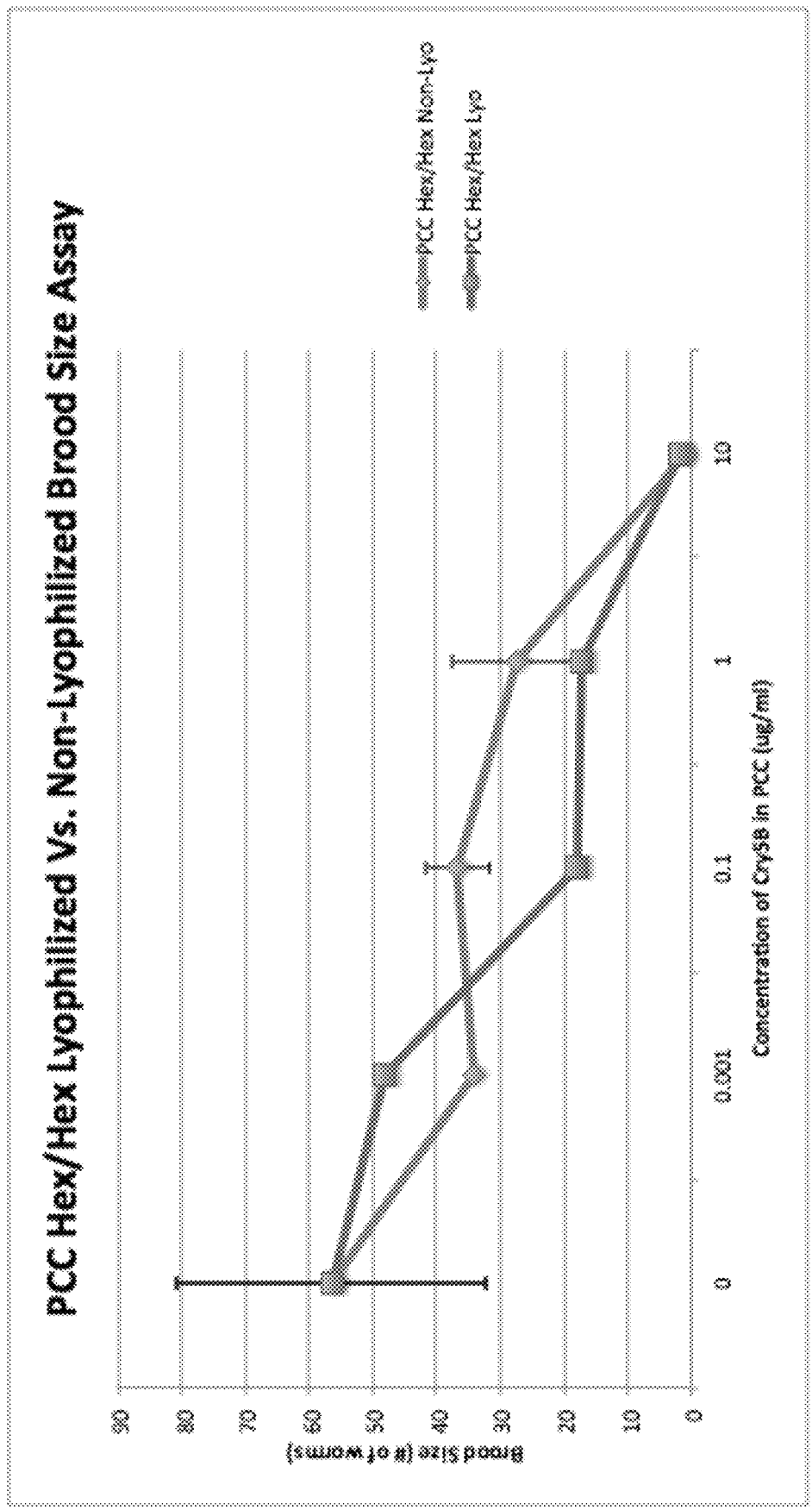
FIG. 14 shows a line graph depicting the bioactivity of PCC processed from BaCC with 10% hexane to kill the bacterium and 50% hexane to remove other bacterial contaminants (PCC-Hex/Hex).

Example 10: PCC Purified by the Improved Method is an Effective Toxin Against Nematodes In another example, the method of Example 9 was combined with the hexane phase partitioning method of Example 9. FIG. 14 shows a graph of the bioactivity of PCC processed from BaCC with 10% hexane to kill the bacterium and 50% hexane to remove other bacterial contaminants (PCC-Hex/Hex). The non-lyophilized PCC is shown on the graph as diamonds and the lyophilized PCC is shown as squares. The readout is the average three-day brood size of a single C. elegans starting at the larval stage L4 (n=3 per condition). The PCC efficacy is excellent since at 10 μg/mL there is complete inhibition of brood size production. In comparison, published data indicates an average 70% inhibition at this dose (Hu, Y, et al., Proc Natl Acad Sci USA 107: 5955-60 (2010)). These data demonstrate that the PCC Hex/Hex process is fully compatible with lyophilization.

Figure 15:
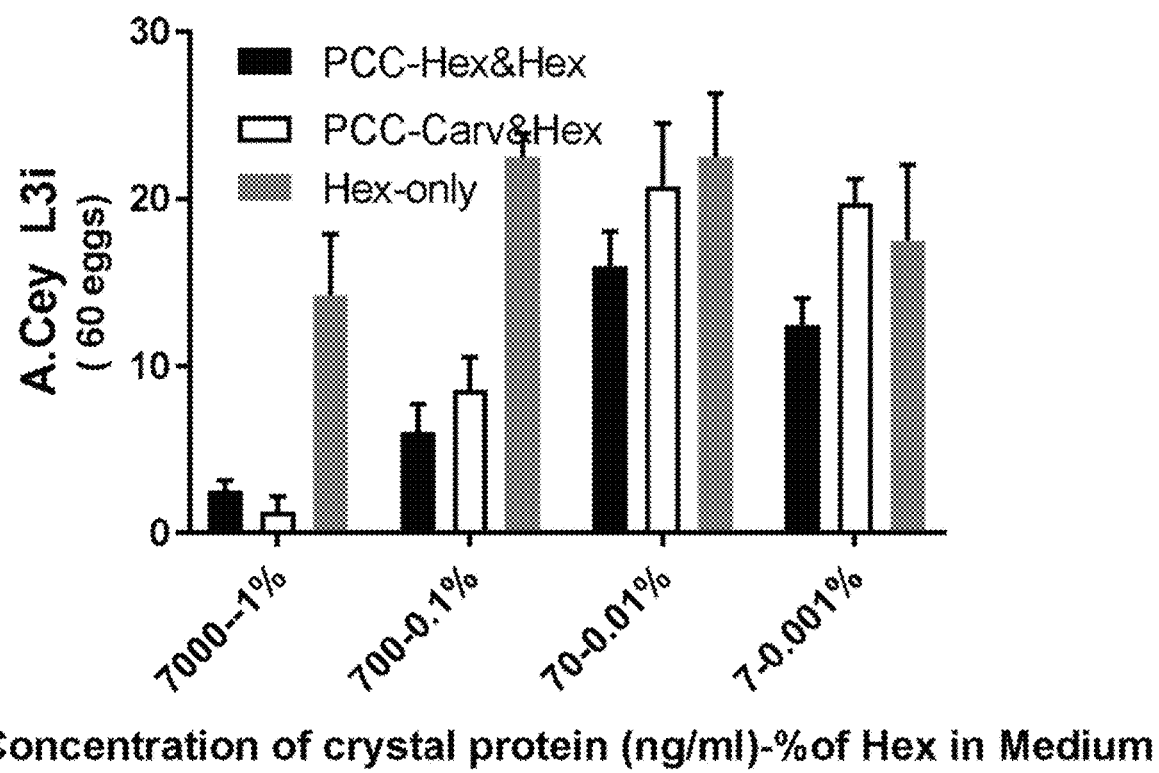
FIG. 15 shows a bar graph depicting the bioactivity of PCC processed from BaCC with carvacrol to kill the bacterium (IBaCC), with 50% hexane to remove other bacterial contaminants (PCC-Carv&Hex), and with 10% hexane to kill the bacterium and 50% hexane to remove other bacterial contaminants (PCC-Hex&Hex).

Example 11: PCC Purified by the Improved Method is an Effective Toxin Against Hookworms FIG. 15 shows the bioactivity of PCC processed from BaCC with carvacrol to kill the bacterium (IBaCC), and 50% hexane phase partitioning to remove other bacterial contaminants (PCC-Carv&Hex). The readout is the percent of hookworm A. ceylanicum eggs that reach mature infectious larval stage at 7 days. A lower bar indicates more inhibition of hookworm growth and development, and is indicative of intoxication. Control is hexane only in the medium at the same final concentration as in the sample with PCC. The data show that hexane alone has no effect on the parasites.

Figure 16:
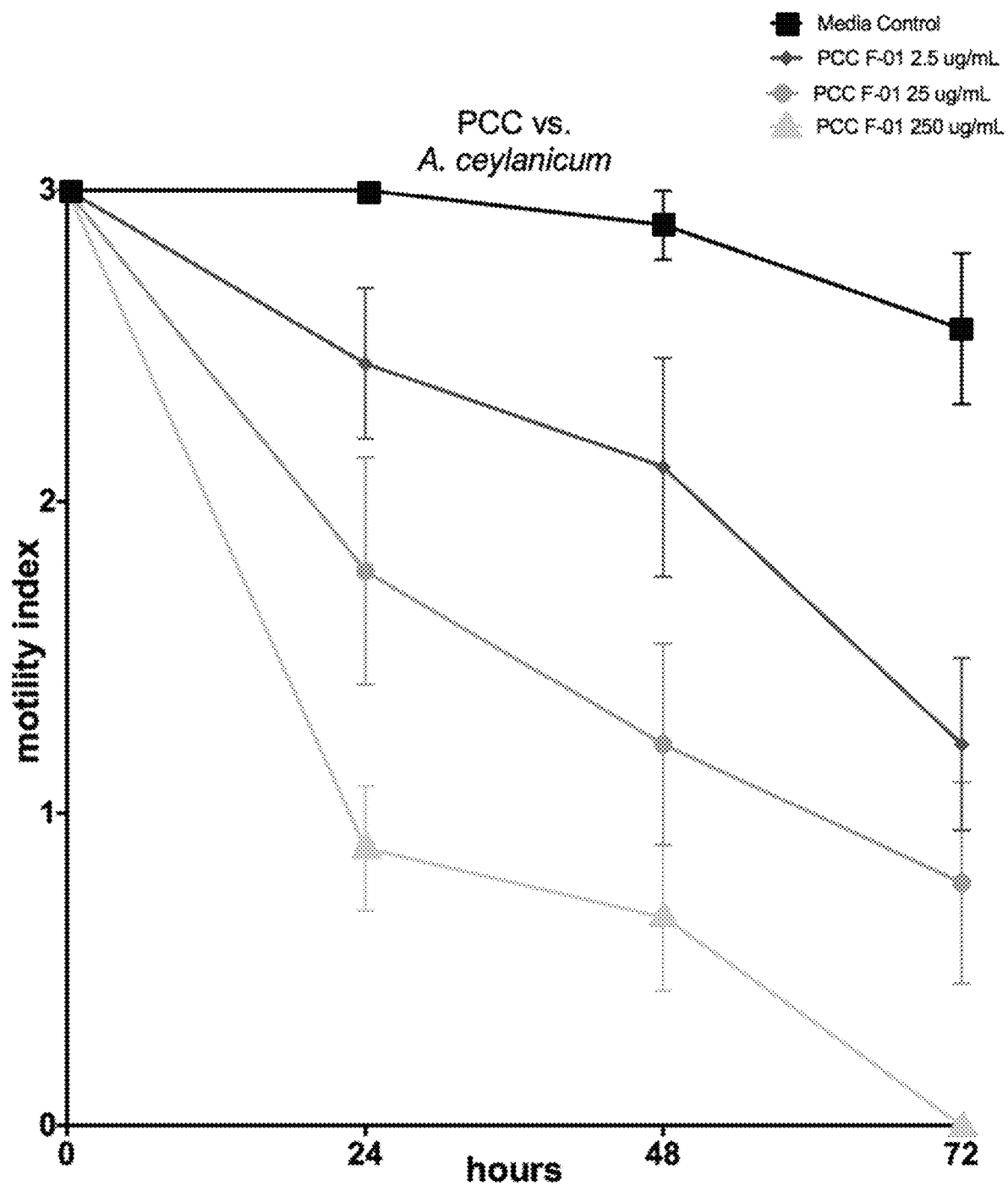
FIG. 16 shows a line graph depicting the bioactivity of PCC processed from BaCC with carvacrol to kill the bacterium and 50% hexane to remove other bacterial contaminants.

FIG. 16 shows the bioactivity of PCC processed from BaCC with carvacrol to kill the bacterium and 50% hexane to remove other bacterial contaminants. The readout is motility of hookworm A. ceylanicum adults in vitro scored every 24 hours, where 3=active and highly motile; 2=slowly motile; 1=immotile unless touched (highly intoxicated); 0=immotile even when touched (presumably dead). The data show a clear dose-response with increasing doses of PCC resulting in decreasing motility, demonstrating that the PCC processed via hexane is highly bioactive.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While particular steps, elements, embodiments and applications of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

```
<160> NUMBER OF SEQ ID NOS: 24

<210> SEQ ID NO 1
<211> LENGTH: 1245
<212> TYPE: PRT
<213> ORGANISM: Bacillus thuringiensis

<400> SEQUENCE: 1

Met Ala Thr Ile Asn Glu Leu Tyr Pro Val Pro Tyr Asn Val Leu Ala
1               5                   10                  15

His Pro Ile Lys Glu Val Asp Asp Pro Tyr Ser Trp Ser Asn Leu Leu
            20                  25                  30

Lys Gly Ile Gln Glu Gly Trp Glu Glu Trp Gly Lys Thr Gly Gln Lys
        35                  40                  45

Lys Leu Phe Glu Asp His Leu Thr Ile Ala Trp Asn Leu Tyr Lys Thr
    50                  55                  60
```

```
Gly Lys Leu Asp Tyr Glu Ala Leu Thr Lys Ala Ser Ile Ser Leu Ile
 65                  70                  75                  80

Gly Phe Ile Pro Gly Ala Glu Ala Ala Val Pro Phe Ile Asn Met Glu
             85                  90                  95

Val Asp Phe Val Trp Pro Lys Leu Phe Gly Ala Asn Thr Glu Gly Lys
            100                 105                 110

Asp Gln Gln Leu Phe Asn Ala Ile Met Asp Ala Val Asn Lys Met Val
        115                 120                 125

Asp Asn Lys Phe Leu Ser Tyr Asn Leu Ser Thr Leu Asn Lys Thr Ile
        130                 135                 140

Glu Gly Ile Gln Gly Asn Leu Gly Leu Phe Gln Asn Ala Ile Gln Val
145                 150                 155                 160

Ala Ile Cys Gln Gly Ser Thr Pro Glu Arg Val Asn Phe Asp Gln Asn
            165                 170                 175

Cys Thr Pro Cys Asn Pro Asn Gln Pro Cys Lys Asp Asp Leu Asp Arg
            180                 185                 190

Val Ala Ser Arg Phe Asp Thr Ala Asn Ser Gln Phe Thr Gln His Leu
        195                 200                 205

Pro Glu Phe Lys Asn Pro Trp Ser Asp Glu Asn Ser Thr Gln Glu Phe
        210                 215                 220

Lys Arg Thr Ser Val Glu Leu Thr Leu Pro Met Tyr Thr Thr Val Ala
225                 230                 235                 240

Thr Leu His Leu Leu Leu Tyr Glu Gly Tyr Ile Glu Phe Met Thr Lys
            245                 250                 255

Trp Asn Phe His Asn Glu Gln Tyr Leu Asn Asn Leu Lys Val Glu Leu
            260                 265                 270

Gln Gln Leu Ile His Ser Tyr Ser Glu Thr Val Arg Thr Ser Phe Leu
        275                 280                 285

Gln Phe Leu Pro Thr Leu Asn Asn Arg Ser Lys Ser Ser Val Asn Ala
        290                 295                 300

Tyr Asn Arg Tyr Val Arg Asn Met Thr Val Asn Cys Leu Asp Ile Ala
305                 310                 315                 320

Ala Thr Trp Pro Thr Phe Asp Thr His Asn Tyr His Gln Gly Gly Lys
            325                 330                 335

Leu Asp Leu Thr Arg Ile Ile Leu Ser Asp Thr Ala Gly Pro Ile Glu
            340                 345                 350

Glu Tyr Thr Thr Gly Asp Lys Thr Ser Gly Pro Glu His Ser Asn Ile
        355                 360                 365

Thr Pro Asn Asn Ile Leu Asp Thr Pro Ser Pro Thr Tyr Gln His Ser
        370                 375                 380

Phe Val Ser Val Asp Ser Ile Val Tyr Ser Arg Lys Glu Leu Gln Gln
385                 390                 395                 400

Leu Asp Ile Ala Thr Tyr Ser Thr Asn Asn Ser Asn Asn Cys His Pro
            405                 410                 415

Tyr Gly Leu Arg Leu Ser Tyr Thr Asp Gly Ser Arg Tyr Asp Tyr Gly
            420                 425                 430

Asp Asn Gln Pro Asp Phe Thr Thr Ser Asn Asn Asn Tyr Cys His Asn
        435                 440                 445

Ser Tyr Thr Ala Pro Ile Thr Leu Val Asn Ala Arg His Leu Tyr Asn
        450                 455                 460

Ala Lys Gly Ser Leu Gln Asn Val Glu Ser Leu Val Val Ser Thr Val
465                 470                 475                 480
```

-continued

```
Asn Gly Gly Ser Gly Ser Cys Ile Cys Asp Ala Trp Ile Asn Tyr Leu
                485                 490                 495

Arg Pro Pro Gln Thr Ala Lys Asn Glu Ser Phe Pro Asp Gln Lys Asp
            500                 505                 510

Asn Val Leu Tyr Pro Ile Thr Glu Thr Val Asn Lys Gly Thr Gly Gly
        515                 520                 525

Asn Leu Gly Val Ile Ser Ala Tyr Val Pro Met Glu Leu Val Pro Glu
    530                 535                 540

Asn Val Ile Gly Asp Val Asn Ala Asp Thr Lys Leu Pro Leu Thr Gln
545                 550                 555                 560

Leu Lys Gly Phe Pro Phe Glu Lys Tyr Gly Ser Glu Tyr Asn Asn Arg
                565                 570                 575

Gly Ile Ser Leu Val Arg Glu Trp Ile Asn Gly Asn Asn Ala Val Lys
            580                 585                 590

Leu Ser Asn Ser Gln Ser Val Gly Ile Gln Ile Thr Asn Gln Thr Glu
        595                 600                 605

Gln Lys Tyr Glu Ile Arg Cys Arg Tyr Ala Ser Lys Gly Asp Asn Asn
    610                 615                 620

Val Tyr Phe Asn Val Asp Leu Ser Glu Asn Pro Phe Arg Asn Ser Ile
625                 630                 635                 640

Ser Phe Gly Ser Thr Glu Ser Ser Val Gly Val Gln Gly Glu Asn
                645                 650                 655

Gly Lys Tyr Ile Leu Lys Ser Ile Thr Val Glu Ile Pro Ala Gly
            660                 665                 670

Ser Phe Tyr Val His Ile Thr Asn Gln Gly Ser Ser Asp Leu Phe Leu
        675                 680                 685

Asp Arg Ile Glu Phe Val Pro Lys Ile Gln Phe Gln Phe Cys Asp Asn
    690                 695                 700

Asn Asn Leu His Cys Asp Cys Asn Asn Pro Val Asp Thr Asp Cys Thr
705                 710                 715                 720

Phe Cys Cys Val Cys Thr Ser Leu Thr Asp Cys Asp Cys Asn Asn Pro
                725                 730                 735

Arg Gly Leu Asp Cys Thr Leu Cys Cys Gln Val Glu Asn Gln Leu Pro
            740                 745                 750

Ser Phe Val Thr Leu Thr Asp Leu Gln Asn Ile Thr Thr Gln Val Asn
        755                 760                 765

Ala Leu Val Ala Ser Ser Glu His Asp Thr Leu Ala Thr Asp Val Ser
    770                 775                 780

Asp Tyr Glu Ile Glu Glu Val Leu Lys Val Asp Ala Leu Ser Gly
785                 790                 795                 800

Glu Val Phe Gly Lys Glu Lys Lys Ala Leu Arg Lys Leu Val Asn His
                805                 810                 815

Thr Lys Arg Leu Ser Lys Ala Arg Asn Leu Leu Ile Gly Gly Asn Phe
            820                 825                 830

Asp Asn Leu Asp Ala Trp Tyr Arg Gly Arg Asn Val Val Asn Val Ser
        835                 840                 845

Asp His Glu Leu Phe Lys Ser Asp His Tyr Leu Leu Pro Pro Pro Thr
    850                 855                 860

Leu Tyr Ser Ser Tyr Met Phe Gln Lys Val Glu Ser Lys Leu Lys
865                 870                 875                 880

Ala Asn Thr Arg Tyr Ser Val Ser Gly Phe Ile Ala His Ala Glu Asp
                885                 890                 895

Leu Glu Ile Val Val Ser Glu Tyr Gly Gln Glu Val Lys Lys Val Val
```

```
                       900                 905                 910
Gln Val Pro Tyr Gly Glu Ala Phe Pro Leu Thr Ser Arg Gly Ala Ile
            915                 920                 925

Cys Cys Pro Arg Ser Thr Ser Asn Gly Lys Pro Ala Asp Pro His
            930                 935                 940

Glu Phe Ser Tyr Ser Ile Asp Val Gly Thr Leu Asp Val Glu Ala Asn
945                 950                 955                 960

Pro Gly Ile Glu Leu Gly Leu Arg Ile Val Glu Arg Thr Gly Met Ala
            965                 970                 975

Arg Tyr Ser Asn Leu Glu Ile Arg Glu Asp Pro Pro Leu Lys Lys Asn
            980                 985                 990

Glu Leu Arg Asn Val Gln Arg Ala  Ala Arg Asn Trp Arg  Ser Ala Tyr
            995                 1000                1005

Asp Gln  Glu Arg Ala Glu Val  Thr Ala Leu Ile Gln  Pro Val Leu
        1010                 1015                 1020

Asn Gln  Ile Asn Ala Leu Tyr  Glu Asn Glu Asp Trp  Asn Gly Ala
        1025                 1030                 1035

Ile Arg  Ser Gly Val Ser Tyr  His Asp Leu Glu Ala  Ile Val Leu
        1040                 1045                 1050

Pro Thr  Leu Pro Lys Leu Asn  His Trp Phe Met Ser  Asp Met Leu
        1055                 1060                 1065

Gly Glu  Gln Gly Ser Ile Leu  Ala Gln Phe Gln Glu  Ala Leu Asp
        1070                 1075                 1080

Arg Ala  Tyr Thr Gln Leu Glu  Glu Ser Thr Ile Leu  His Asn Gly
        1085                 1090                 1095

His Phe  Thr Thr Asp Ala Ala  Asn Trp Thr Ile Glu  Gly Asp Ala
        1100                 1105                 1110

His His  Ala Ile Leu Glu Asp  Gly Arg Arg Val Leu  Arg Leu Pro
        1115                 1120                 1125

Asp Trp  Ser Ser Ser Val Ser  Gln Thr Ile Glu Ile  Glu Asn Phe
        1130                 1135                 1140

Asp Pro  Asp Lys Glu Tyr Gln  Leu Val Phe His Ala  Gln Gly Glu
        1145                 1150                 1155

Gly Thr  Val Ser Leu Gln His  Gly Glu Glu Gly Glu  Tyr Val Glu
        1160                 1165                 1170

Thr His  Pro His Lys Ser Ala  Asn Phe Thr Thr Ser  His Arg Gln
        1175                 1180                 1185

Gly Leu  Thr Phe Glu Thr Asn  Lys Val Thr Val Glu  Ile Thr Ser
        1190                 1195                 1200

Glu Asp  Gly Glu Phe Leu Val  Asp His Ile Ala Leu  Val Glu Ala
        1205                 1210                 1215

Pro Leu  Pro Thr Asp Asp Gln  Ser Ser Asp Gly Asn  Thr Phe Ser
        1220                 1225                 1230

Asn Thr  Asn Ser Asn Thr Ser  Met Asn Asn Asn Gln
        1235                 1240                 1245

<210> SEQ ID NO 2
<211> LENGTH: 803
<212> TYPE: PRT
<213> ORGANISM: Bacillus thuringiensis

<400> SEQUENCE: 2

Met Thr Cys Gln Leu Gln Ala Gln Pro Leu Ile Pro Tyr Asn Val Leu
1               5                   10                  15
```

-continued

```
Ala Gly Tyr Pro Thr Ser Asn Thr Gly Ser Pro Ile Gly Asn Ala Gly
            20                  25                  30

Asn Gln Phe Asp Gln Phe Glu Gln Thr Val Lys Glu Leu Lys Glu Ala
        35                  40                  45

Trp Glu Ala Phe Gln Lys Asn Gly Ser Phe Ser Leu Ala Ala Leu Glu
    50                  55                  60

Lys Gly Phe Asp Ala Ala Ile Gly Gly Ser Phe Asp Tyr Leu Gly
65                  70                  75                  80

Leu Val Gln Ala Gly Leu Gly Leu Val Gly Thr Leu Gly Ala Ala Ile
                85                  90                  95

Pro Gly Val Ser Val Ala Val Pro Leu Ile Ser Met Leu Val Gly Val
            100                 105                 110

Phe Trp Pro Lys Gly Thr Asn Asn Gln Glu Asn Leu Ile Thr Val Ile
        115                 120                 125

Asp Lys Glu Val Gln Arg Ile Leu Asp Glu Lys Leu Ser Asp Gln Leu
    130                 135                 140

Ile Lys Lys Ile Asn Ala Asp Leu Asn Ala Phe Thr Asp Leu Val Thr
145                 150                 155                 160

Arg Leu Glu Glu Val Ile Ile Asp Ala Thr Phe Glu Asn His Lys Pro
                165                 170                 175

Val Leu Gln Val Ser Lys Ser Asn Tyr Met Lys Val Asp Ser Ala Tyr
            180                 185                 190

Phe Ser Thr Gly Gly Ile Leu Thr Leu Gly Met Ser Asp Phe Leu Thr
        195                 200                 205

Asp Thr Tyr Ser Lys Leu Thr Phe Pro Leu Tyr Val Leu Gly Ala Thr
    210                 215                 220

Met Lys Leu Ser Ala Tyr His Ser Tyr Ile Gln Phe Gly Asn Thr Trp
225                 230                 235                 240

Leu Asn Lys Val Tyr Asp Leu Ser Ser Asp Glu Gly Lys Thr Met Ser
                245                 250                 255

Gln Ala Leu Ala Arg Ala Lys Gln His Met Arg Gln Asp Ile Ala Phe
            260                 265                 270

Tyr Thr Ser Gln Ala Leu Asn Met Phe Thr Gly Asn Leu Pro Ser Leu
        275                 280                 285

Ser Ser Asn Lys Tyr Ala Ile Asn Asp Tyr Asn Val Tyr Thr Arg Ala
    290                 295                 300

Met Val Leu Asn Gly Leu Asp Ile Val Ala Thr Trp Pro Thr Leu Tyr
305                 310                 315                 320

Pro Asp Asp Tyr Ser Ser Gln Ile Lys Leu Glu Lys Thr Arg Val Ile
                325                 330                 335

Phe Ser Asp Met Val Gly Gln Ser Glu Ser Arg Asp Gly Ser Val Thr
            340                 345                 350

Ile Lys Asn Ile Phe Asp Asn Thr Asp Ser His Gln His Gly Ser Ile
        355                 360                 365

Gly Leu Asn Ser Ile Ser Tyr Phe Pro Asp Glu Leu Gln Lys Ala Gln
    370                 375                 380

Leu Arg Met Tyr Asp Tyr Asn His Lys Pro Tyr Cys Thr Asp Cys Phe
385                 390                 395                 400

Cys Trp Pro Tyr Gly Val Ile Leu Asn Tyr Asn Lys Asn Thr Phe Arg
                405                 410                 415

Tyr Gly Asp Asn Asp Pro Gly Leu Ser Gly Asp Val Gln Leu Pro Ala
            420                 425                 430

Pro Met Ser Val Val Asn Ala Gln Thr Gln Thr Ala Gln Tyr Thr Asp
```

-continued

```
        435                 440                 445

Gly Glu Asn Ile Asn Thr Asp Thr Gly Arg Ser Trp Leu Cys Thr Leu
    450                 455                 460

Arg Gly Tyr Cys Thr Thr Asn Cys Phe Pro Gly Arg Gly Cys Tyr Asn
465                 470                 475                 480

Asn Ser Thr Gly Tyr Gly Glu Ser Cys Asn Gln Ser Leu Pro Gly Gln
                485                 490                 495

Lys Ile His Ala Leu Tyr Pro Phe Thr Gln Thr Asn Val Leu Gly Gln
            500                 505                 510

Ser Gly Lys Leu Gly Leu Leu Ala Ser His Ile Pro Tyr Asp Leu Ser
        515                 520                 525

Pro Asn Asn Thr Ile Gly Asp Lys Asp Thr Asp Ser Thr Asn Ile Val
    530                 535                 540

Ala Lys Gly Ile Pro Val Glu Lys Gly Tyr Ala Ser Ser Gly Gln Lys
545                 550                 555                 560

Val Glu Ile Ile Arg Glu Trp Ile Asn Gly Ala Asn Val Val Gln Leu
                565                 570                 575

Ser Pro Gly Gln Ser Trp Gly Met Asp Phe Thr Asn Ser Thr Gly Gly
            580                 585                 590

Gln Tyr Met Val Arg Cys Arg Tyr Ala Ser Thr Asn Asp Thr Pro Ile
        595                 600                 605

Phe Phe Asn Leu Val Tyr Asp Gly Gly Ser Asn Pro Ile Tyr Asn Gln
    610                 615                 620

Met Thr Phe Pro Ala Thr Lys Glu Thr Pro Ala His Asp Ser Val Asp
625                 630                 635                 640

Asn Glu Ile Leu Gly Ile Lys Gly Ile Asn Gly Asn Tyr Ser Leu Met
                645                 650                 655

Asn Val Lys Asp Ser Val Glu Leu Pro Ser Gly Lys Phe His Val Phe
            660                 665                 670

Phe Thr Asn Asn Gly Ser Ser Ala Ile Tyr Leu Asp Arg Leu Glu Phe
        675                 680                 685

Val Pro Leu Asp Gln Pro Ala Ala Pro Thr Gln Ser Thr Gln Pro Ile
    690                 695                 700

Asn Tyr Pro Ile Thr Ser Arg Leu Pro His Arg Ser Gly Glu Pro Pro
705                 710                 715                 720

Ala Ile Ile Trp Glu Lys Ser Gly Asn Val Arg Gly Asn Gln Leu Thr
                725                 730                 735

Ile Ser Ala Gln Gly Val Pro Glu Asn Ser Gln Ile Tyr Leu Ser Val
            740                 745                 750

Gly Gly Asp Arg Gln Ile Leu Asp Arg Ser Asn Gly Phe Lys Leu Val
        755                 760                 765

Asn Tyr Ser Pro Thr Tyr Ser Phe Thr Asn Ile Gln Ala Ser Ser Ser
    770                 775                 780

Asn Leu Val Asp Ile Thr Ser Gly Thr Ile Thr Gly Gln Val Gln Val
785                 790                 795                 800

Ser Asn Leu
```

<210> SEQ ID NO 3
<211> LENGTH: 1186
<212> TYPE: PRT
<213> ORGANISM: Bacillus thuringiensis

<400> SEQUENCE: 3

Met Asp Cys Asn Leu Gln Ser Gln Gln Asn Ile Pro Tyr Asn Val Leu

-continued

```
1               5                   10                  15
Ala Ile Pro Val Ser Asn Val Asn Ala Leu Val Asp Thr Ala Gly Asp
                20                  25                  30

Leu Lys Lys Ala Trp Glu Glu Phe Gln Lys Thr Gly Ser Phe Ser Leu
                35                  40                  45

Thr Ala Leu Gln Gln Gly Phe Ser Ala Ser Gln Gly Gly Ala Phe Asn
                50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Val Asn Met Val Ile Gly Trp
                85                  90                  95

Leu Trp Pro His Glu Asn Lys Thr Ala Asp Thr Glu Asn Leu Ile Lys
                100                 105                 110

Leu Ile Asp Glu Glu Ile Gln Lys Gln Leu Asn Lys Ala Leu Leu Asp
                115                 120                 125

Gln Asp Arg Asn Asn Trp Thr Ser Phe Leu Glu Ser Ile Phe Asp Thr
                130                 135                 140

Ser Ala Thr Val Ser Asn Ala Asp Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
                180                 185                 190

Asn Glu Asn Gln Ile Met Asn Gly Asn Phe Asp Val Ala Ala Ala Pro
                195                 200                 205

Tyr Phe Val Asp Gly Ala Thr Leu Arg Leu Ser Leu Tyr Gln Ser Tyr
                210                 215                 220

Ile Lys Phe Cys Asn Ser Trp Ile Asp Ala Val Gly Phe Ser Thr Asn
225                 230                 235                 240

Asp Ala Asn Thr Gln Lys Ala Asn Leu Ala Arg Thr Lys Leu Thr Met
                245                 250                 255

Arg Ser Thr Ile Asn Glu Tyr Thr Gln Arg Val Met Lys Val Phe Lys
                260                 265                 270

Asp Ser Lys Asn Met Pro Thr Ile Gly Thr Asn Lys Phe Ser Val Asp
                275                 280                 285

Ala Tyr Asn Val Tyr Val Lys Gly Met Thr Leu Asn Val Leu Asp Met
                290                 295                 300

Val Ala Ile Trp Ser Ser Leu Tyr Pro Asn Asp Tyr Thr Ser Gln Thr
305                 310                 315                 320

Ala Ile Glu Gln Thr Arg Val Thr Phe Ser Asn Met Val Gly Gln Glu
                325                 330                 335

Glu Gly Thr Asp Gly Thr Leu Lys Ile Tyr Asn Thr Phe Asp Ser Leu
                340                 345                 350

Ser Tyr Gln His Ser Leu Ile Pro Asn Asn Val Asn Leu Ile Ser
                355                 360                 365

Tyr Tyr Thr Asp Glu Leu Gln Asn Leu Glu Leu Ala Val Tyr Thr Pro
                370                 375                 380

Lys Gly Gly Ser Gly Tyr Ala Tyr Pro Tyr Gly Phe Ile Leu Asn Tyr
385                 390                 395                 400

Ala Asn Ser Asn Tyr Lys Tyr Gly Asp Asn Asp Pro Thr Gly Lys Pro
                405                 410                 415

Leu Asn Lys Gln Asp Gly Pro Ile Gln Gln Ile Asn Ala Ala Thr Gln
                420                 425                 430
```

```
Asn Ser Lys Tyr Leu Asp Gly Glu Thr Ile Asn Gly Ile Gly Ala Ser
        435                 440                 445

Leu Pro Gly Tyr Cys Thr Thr Gly Ser Ser Ala Thr Glu Gln Pro Phe
        450                 455                 460

Ser Cys Thr Gly Thr Ala Asn Ser Tyr Lys Ala Ser Cys Asn Pro Ser
465                 470                 475                 480

Asp Thr Asn Gln Lys Ile Asn Ala Leu Tyr Ala Phe Thr Gln Thr Asn
                    485                 490                 495

Val Lys Gly Ser Thr Gly Lys Leu Gly Val Leu Ala Ser Leu Val Pro
                500                 505                 510

Tyr Asp Leu Asn Pro Lys Asn Val Phe Gly Glu Leu Asp Ser Asp Thr
            515                 520                 525

Asn Asn Val Ile Leu Lys Gly Ile Pro Ala Glu Lys Gly Tyr Phe Pro
        530                 535                 540

Asn Asn Ala Arg Pro Thr Val Val Lys Glu Trp Ile Asn Gly Ala Ser
545                 550                 555                 560

Ala Val Pro Phe Tyr Ser Gly Asn Thr Leu Phe Met Thr Ala Thr Asn
                    565                 570                 575

Leu Thr Ala Thr Gln Tyr Lys Ile Arg Ile Arg Tyr Ala Asn Pro Asn
                580                 585                 590

Ser Asp Thr Gln Ile Ser Val Leu Ile Thr Gln Asn Gly Ser Gln Ile
            595                 600                 605

Ser Asn Ser Asn Leu Thr Leu Tyr Ser Thr Asp Ser Ser Met Ser
        610                 615                 620

Ser Asn Leu Pro Gln Asn Val Tyr Val Thr Gly Glu Asn Gly Asn Tyr
625                 630                 635                 640

Thr Leu Leu Asp Leu Tyr Ser Thr Thr Asn Val Leu Ser Thr Gly Asp
                    645                 650                 655

Ile Thr Leu Lys Leu Thr Gly Gly Asn Gln Lys Ile Phe Ile Asp Arg
                660                 665                 670

Ile Glu Phe Ile Pro Thr Met Pro Val Pro Ala Pro Thr Asn Asn Thr
            675                 680                 685

Asn Asn Asn Asn Gly Asp Asn Gly Asn Asn Pro Pro His His Gly
        690                 695                 700

Cys Ala Ile Ala Gly Thr Gln Gln Leu Cys Ser Gly Pro Pro Lys Phe
705                 710                 715                 720

Glu Gln Val Ser Asp Leu Glu Lys Ile Thr Thr Gln Val Tyr Met Leu
                    725                 730                 735

Phe Lys Ser Ser Ser Tyr Glu Glu Leu Ala Ile Lys Val Ser Ser Tyr
                740                 745                 750

Gln Ile Asn Gln Val Ala Leu Lys Val Met Ala Leu Ser Asp Glu Lys
            755                 760                 765

Phe Cys Glu Glu Lys Arg Leu Leu Arg Lys Leu Val Asn Lys Ala Asn
        770                 775                 780

Gln Leu Leu Glu Ala Arg Asn Leu Leu Val Gly Gly Asn Phe Glu Thr
785                 790                 795                 800

Thr Gln Asn Trp Val Leu Gly Thr Asn Ala Tyr Asp Asn Tyr Asp Ser
                    805                 810                 815

Phe Leu Phe Asn Gly Asn Tyr Leu Ser Leu Gln Pro Ala Ser Gly Phe
                820                 825                 830

Phe Thr Ser Tyr Ala Tyr Gln Lys Ile Asp Glu Ser Thr Leu Lys Pro
            835                 840                 845
```

Tyr Thr Arg Tyr Lys Val Ser Gly Phe Ile Gly Gln Ser Asn Gln Val
              850                 855                 860

Glu Leu Ile Ile Ser Arg Tyr Gly Lys Glu Ile Asp Lys Ile Leu Asn
865                 870                 875                 880

Val Pro Tyr Ala Gly Pro Leu Pro Ile Thr Ala Asp Ala Ser Ile Thr
                    885                 890                 895

Cys Cys Ala Pro Glu Ile Asp Gln Cys Asp Gly Gly Gln Ser Asp Ser
                900                 905                 910

His Phe Phe Asn Tyr Ser Ile Asp Val Gly Ala Leu His Pro Glu Leu
            915                 920                 925

Asn Pro Gly Asp Glu Ile Gly Leu Lys Ile Val Gln Ser Asn Gly Tyr
930                 935                 940

Ile Ser Ile Ser Asn Leu Glu Ile Ile Glu Glu Arg Pro Leu Thr Glu
945                 950                 955                 960

Met Glu Ile Gln Ala Val Asn Arg Lys Asp Gln Lys Trp Lys Arg Glu
                965                 970                 975

Leu Leu Leu Glu Cys Ala Ser Val Ser Glu Leu Leu Pro Ile Asp
                980                 985                 990

Asn Gln Ile Asp Ser Leu Phe Lys Asp Ala Asn Trp Tyr Asn Asp Ile
            995                 1000                1005

Leu Pro His Val Thr Tyr Gln Thr Leu Lys Asn Ile Ile Val Pro
    1010                1015                1020

Asp Leu Pro Lys Leu Lys His Trp Phe Ile Asp His Leu Pro Gly
    1025                1030                1035

Glu Tyr His Glu Ile Glu Gln Lys Met Lys Glu Ala Leu Lys His
    1040                1045                1050

Ala Phe Thr Gln Leu Asp Glu Lys Asn Leu Ile His Asn Gly His
    1055                1060                1065

Phe Ala Thr Asn Leu Ile Asp Trp Gln Val Glu Gly Asp Ala Phe
    1070                1075                1080

Met Lys Val Leu Glu Asn Asn Ala Leu Ala Leu Gln Leu Ser Asn
    1085                1090                1095

Trp Asp Ser Ser Val Ser Gln Ser Ile Asp Ile Leu Glu Phe Asp
    1100                1105                1110

Glu Asp Lys Ala Tyr Lys Leu Arg Val Tyr Ala Gln Gly Ser Gly
    1115                1120                1125

Thr Ile Gln Phe Gly Asn Cys Glu Asp Glu Ala Ile Gln Phe Asn
    1130                1135                1140

Thr Asn Ser Phe Val Tyr Lys Glu Lys Ile Ile Tyr Phe Asp Ser
    1145                1150                1155

Pro Ser Ile Asn Leu His Ile Gln Ser Glu Gly Ser Glu Phe Val
    1160                1165                1170

Val Ser Ser Ile Asp Leu Val Glu Leu Ser Asp Asp Glu
    1175                1180                1185

<210> SEQ ID NO 4
<211> LENGTH: 1167
<212> TYPE: PRT
<213> ORGANISM: Bacillus thuringiensis

<400> SEQUENCE: 4

Met Thr Asn Pro Thr Ile Leu Tyr Pro Ser Tyr His Asn Val Leu Ala
1               5                   10                  15

His Pro Ile Arg Leu Asp Ser Phe Phe Asp Pro Phe Val Glu Thr Phe
                20                  25                  30

```
Lys Asp Leu Lys Gly Ala Trp Glu Glu Phe Gly Lys Thr Gly Tyr Met
         35                  40                  45

Asp Pro Leu Lys Gln His Leu Gln Ile Ala Trp Asp Thr Ser Gln Asn
 50                  55                  60

Gly Thr Val Asp Tyr Leu Ala Leu Thr Lys Ala Ser Ile Ser Leu Ile
 65                  70                  75                  80

Gly Leu Ile Pro Gly Ala Asp Ala Val Val Pro Phe Ile Asn Met Phe
                 85                  90                  95

Val Asp Phe Ile Phe Pro Lys Leu Phe Gly Arg Gly Ser Gln Gln Asn
                100                 105                 110

Ala Gln Ala Gln Phe Phe Glu Leu Ile Ile Glu Lys Val Lys Glu Leu
             115                 120                 125

Val Asp Glu Asp Phe Arg Asn Phe Thr Leu Asn Asn Leu Leu Asn Tyr
         130                 135                 140

Leu Asp Gly Met Gln Thr Ala Leu Ser His Phe Gln Asn Asp Val Gln
145                 150                 155                 160

Ile Ala Ile Cys Gln Gly Glu Gln Pro Gly Leu Met Leu Asp Gln Thr
                165                 170                 175

Pro Thr Ala Cys Thr Pro Thr Asp His Leu Ile Ser Val Arg Glu
             180                 185                 190

Ser Phe Lys Asp Ala Arg Thr Thr Ile Glu Thr Ala Leu Pro His Phe
         195                 200                 205

Lys Asn Pro Asn Leu Ser Thr Asn Asp Asn Thr Pro Asp Phe Asn Ser
         210                 215                 220

Asp Thr Val Leu Leu Thr Leu Pro Met Tyr Thr Thr Gly Ala Thr Leu
225                 230                 235                 240

Asn Leu Ile Leu His Gln Gly Tyr Ile Gln Phe Ala Glu Arg Trp Lys
                245                 250                 255

Ser Val Asn Tyr Asp Glu Ser Phe Ile Asn Gln Thr Lys Val Asp Leu
                260                 265                 270

Gln Arg Arg Ile Gln Asp Tyr Ser Thr Thr Val Ser Thr Thr Phe Glu
         275                 280                 285

Lys Phe Lys Pro Thr Leu Asn Pro Ser Asn Lys Glu Ser Val Asn Lys
         290                 295                 300

Tyr Asn Arg Tyr Val Arg Ser Met Thr Leu Gln Ser Leu Asp Ile Ala
305                 310                 315                 320

Ala Thr Trp Pro Thr Leu Asp Asn Val Asn Tyr Pro Ser Asn Val Asp
                325                 330                 335

Ile Gln Leu Asp Gln Thr Arg Leu Val Phe Ser Asp Val Ala Gly Pro
             340                 345                 350

Trp Glu Gly Asn Asp Asn Ile Thr Ser Asn Ile Ile Asp Val Leu Thr
         355                 360                 365

Pro Ile Asn Thr Gly Ile Gly Phe Gln Glu Ser Ser Asp Leu Arg Lys
         370                 375                 380

Phe Thr Tyr Pro Arg Ile Glu Leu Gln Ser Met Gln Phe His Gly Gln
385                 390                 395                 400

Tyr Val Asn Ser Lys Ser Val Glu His Cys Tyr Ser Asp Gly Leu Lys
                405                 410                 415

Leu Asn Tyr Lys Asn Lys Thr Ile Thr Ala Gly Val Ser Asn Ile Asp
             420                 425                 430

Glu Ser Asn Gln Asn Asn Lys His Asn Tyr Gly Pro Val Ile Asn Ser
         435                 440                 445
```

```
Pro Ile Thr Asp Ile Asn Val Asn Ser Gln Asn Ser Gln Tyr Leu Asp
            450                 455                 460

Leu Asn Ser Val Met Val Asn Gly Gly Gln Lys Val Thr Gly Cys Ser
465                 470                 475                 480

Pro Leu Ser Ser Asn Gly Asn Ser Asn Asn Ala Ala Leu Pro Asn Gln
                485                 490                 495

Lys Ile Asn Val Ile Tyr Ser Val Gln Ser Asn Asp Lys Pro Glu Lys
            500                 505                 510

His Ala Asp Thr Tyr Arg Lys Trp Gly Tyr Met Ser Ser His Ile Pro
            515                 520                 525

Tyr Asp Leu Val Pro Glu Asn Val Ile Gly Asp Ile Asp Pro Asp Thr
530                 535                 540

Lys Gln Pro Ser Leu Leu Leu Lys Gly Phe Pro Ala Glu Lys Gly Tyr
545                 550                 555                 560

Gly Asp Ser Ile Ala Tyr Val Ser Glu Pro Leu Asn Gly Ala Asn Ala
                565                 570                 575

Val Lys Leu Thr Ser Tyr Gln Val Leu Gln Met Glu Val Thr Asn Gln
            580                 585                 590

Thr Thr Gln Lys Tyr Arg Ile Arg Ile Arg Tyr Ala Thr Gly Gly Asp
            595                 600                 605

Thr Ala Ala Ser Ile Trp Phe His Ile Ile Gly Pro Ser Gly Asn Asp
610                 615                 620

Leu Thr Asn Glu Gly His Asn Phe Ser Ser Val Ser Ser Arg Asn Lys
625                 630                 635                 640

Met Phe Val Gln Gly Asn Asn Gly Lys Tyr Val Leu Asn Ile Leu Thr
                645                 650                 655

Asp Ser Ile Glu Leu Pro Ser Gly Gln Gln Thr Ile Leu Ile Gln Asn
            660                 665                 670

Thr Asn Ser Gln Asp Leu Phe Leu Asp Arg Ile Glu Phe Ile Ser Leu
            675                 680                 685

Pro Ser Thr Ser Thr Pro Thr Ser Thr Asn Phe Val Glu Pro Glu Ser
690                 695                 700

Leu Glu Lys Ile Ile Asn Gln Val Asn Gln Leu Phe Ser Ser Ser Ser
705                 710                 715                 720

Gln Thr Glu Leu Ala His Thr Val Ser Asp Tyr Lys Ile Asp Gln Val
                725                 730                 735

Val Leu Lys Val Asn Ala Leu Ser Asp Asp Val Phe Gly Val Glu Lys
            740                 745                 750

Lys Ala Leu Arg Lys Leu Val Asn Gln Ala Lys Gln Leu Ser Lys Ala
            755                 760                 765

Arg Asn Val Leu Val Gly Gly Asn Phe Glu Lys Gly His Glu Trp Ala
770                 775                 780

Leu Ser Arg Glu Ala Thr Met Val Ala Asn His Glu Leu Phe Lys Gly
785                 790                 795                 800

Asp His Leu Leu Leu Pro Pro Thr Leu Tyr Pro Ser Tyr Ala Tyr
                805                 810                 815

Gln Lys Ile Asp Glu Ser Lys Leu Lys Ser Asn Thr Arg Tyr Thr Val
            820                 825                 830

Ser Gly Phe Ile Ala Gln Ser Glu His Leu Glu Val Val Val Ser Arg
            835                 840                 845

Tyr Gly Lys Glu Val His Asp Met Leu Asp Ile Pro Tyr Glu Glu Ala
850                 855                 860

Leu Pro Ile Ser Ser Asp Glu Ser Pro Asn Cys Cys Lys Pro Ala Ala
```

```
            865                 870                 875                 880
        Cys Gln Cys Ser Ser Cys Asp Gly Ser Gln Ser Asp Ser His Phe Phe
                        885                 890                 895

Ser Tyr Ser Ile Asp Val Gly Ser Leu Gln Ser Asp Val Asn Leu Gly
                    900                 905                 910

Ile Glu Phe Gly Leu Arg Ile Ala Lys Pro Asn Gly Phe Ala Lys Ile
                    915                 920                 925

Ser Asn Leu Glu Ile Lys Glu Asp Arg Pro Leu Thr Glu Lys Glu Ile
                    930                 935                 940

Lys Lys Val Gln Arg Lys Glu Gln Lys Trp Lys Lys Ala Phe Asn Gln
        945                 950                 955                 960

Glu Gln Ala Glu Val Ala Thr Thr Leu Gln Pro Thr Leu Asp Gln Ile
                        965                 970                 975

Asn Ala Leu Tyr Gln Asn Glu Asp Trp Asn Gly Ser Val His Pro Ala
                    980                 985                 990

Ser Asp Tyr Gln His Leu Ser Ala Val Val Val Pro Thr Leu Pro Lys
                    995                1000                1005

Gln Arg His Trp Phe Met Glu Gly Arg Glu Gly Glu His Val Val
                   1010                1015                1020

Leu Thr Gln Gln Phe Gln Gln Ala Leu Asp Arg Ala Phe Gln Gln
                   1025                1030                1035

Ile Glu Glu Gln Asn Leu Thr His Asn Gly Asn Leu Ala Asn Gly
                   1040                1045                1050

Leu Thr Asp Trp Thr Val Gly Asp Ala Gln Leu Thr Ile Phe
                   1055                1060                1065

Asp Glu Asp Pro Val Leu Glu Leu Ala His Trp Asp Ala Ser Ile
                   1070                1075                1080

Ser Gln Thr Ile Glu Ile Met Asp Phe Glu Gly Arg His Arg Ile
                   1085                1090                1095

Gln Thr Ala Cys Thr Trp Lys Arg Gln Arg Asn Ser Tyr Arg Ser
                   1100                1105                1110

Thr Trp Arg Lys Arg Leu Glu Thr Met Thr Phe Asn Thr Thr Ser
                   1115                1120                1125

Phe Thr Thr Gln Glu Gln Thr Phe Tyr Phe Glu Gly Asp Thr Val
                   1130                1135                1140

Asp Val His Val Gln Ser Glu Asn Asn Thr Phe Leu Ile Asp Ser
                   1145                1150                1155

Val Glu Leu Ile Glu Ile Ile Glu Glu
                   1160                1165

<210> SEQ ID NO 5
<211> LENGTH: 1167
<212> TYPE: PRT
<213> ORGANISM: Bacillus thuringiensis

<400> SEQUENCE: 5

Met Thr Asn Pro Thr Ile Leu Tyr Pro Ser Tyr His Asn Val Leu Ala
1                   5                  10                  15

His Pro Ile Arg Leu Asp Ser Phe Phe Asp Pro Phe Val Glu Thr Phe
                20                  25                  30

Lys Asp Leu Lys Ser Ala Trp Glu Glu Phe Gly Lys Thr Gly Tyr Met
            35                  40                  45

Asp Pro Leu Lys Gln His Leu Gln Ile Ala Trp Asp Thr Ser Gln Asn
        50                  55                  60
```

```
Gly Thr Val Asp Tyr Leu Ala Leu Thr Lys Ala Ser Ile Ser Leu Ile
 65                  70                  75                  80

Gly Leu Ile Pro Gly Ala Asp Ala Val Val Pro Phe Ile Asn Met Phe
                 85                  90                  95

Val Asp Phe Ile Phe Pro Lys Leu Phe Gly Arg Gly Ser Gln Gln Asn
            100                 105                 110

Ala Gln Ala Gln Phe Phe Glu Leu Ile Ile Glu Lys Val Lys Glu Leu
        115                 120                 125

Val Asp Glu Asp Phe Arg Asn Phe Thr Leu Asn Asn Leu Leu Asn Tyr
    130                 135                 140

Leu Asp Gly Met Gln Thr Ala Leu Ser His Phe Gln Asn Asp Val Gln
145                 150                 155                 160

Ile Ala Ile Cys Gln Gly Glu Gln Pro Gly Leu Met Leu Asp Gln Thr
                165                 170                 175

Pro Thr Ala Cys Thr Pro Thr Thr Asp His Leu Ile Ser Val Arg Glu
            180                 185                 190

Ser Phe Lys Asp Ala Arg Thr Thr Ile Glu Thr Ala Leu Pro His Phe
        195                 200                 205

Lys Asn Pro Asn Leu Ser Thr Asn Asp Asn Thr Pro Asp Phe Asn Ser
210                 215                 220

Asp Thr Val Leu Leu Thr Leu Pro Met Tyr Thr Thr Ala Ala Thr Leu
225                 230                 235                 240

Asn Leu Ile Leu His Gln Gly Tyr Ile Gln Phe Ala Glu Arg Trp Lys
                245                 250                 255

Ser Val Asn Tyr Asp Glu Ser Phe Ile Asn Gln Thr Lys Val Asp Leu
            260                 265                 270

Gln Arg Arg Ile Gln Asp Tyr Ser Thr Thr Val Ser Thr Thr Phe Glu
        275                 280                 285

Lys Phe Lys Pro Thr Leu Asn Pro Ser Asn Lys Glu Ser Val Asn Lys
290                 295                 300

Tyr Asn Arg Tyr Val Arg Ser Met Thr Leu Gln Ser Leu Asp Ile Ala
305                 310                 315                 320

Ala Thr Trp Pro Thr Leu Asp Asn Val Asn Tyr Pro Ser Asn Val Asp
                325                 330                 335

Ile Gln Leu Asp Gln Thr Arg Leu Val Phe Ser Asp Val Ala Gly Pro
            340                 345                 350

Trp Glu Gly Asn Asp Asn Ile Thr Ser Asn Ile Ile Asp Val Leu Thr
        355                 360                 365

Pro Ile Asn Thr Gly Ile Gly Phe Gln Glu Ser Ser Asp Leu Arg Lys
370                 375                 380

Phe Thr Tyr Pro Arg Ile Glu Leu Gln Ser Met Gln Phe His Gly Gln
385                 390                 395                 400

Tyr Val Asn Ser Lys Ser Val Glu His Cys Tyr Ser Asp Gly Leu Lys
                405                 410                 415

Leu Asn Tyr Lys Asn Lys Thr Ile Thr Ala Gly Val Ser Asn Ile Asp
            420                 425                 430

Glu Ser Asn Gln Asn Lys His Asn Tyr Gly Pro Val Ile Asn Ser
        435                 440                 445

Pro Ile Thr Asp Ile Asn Val Asn Ser Gln Asn Ser Gln Tyr Leu Asp
            450                 455                 460

Leu Asn Ser Val Met Val Asn Gly Gly Gln Lys Val Ala Gly Cys Ser
465                 470                 475                 480

Pro Leu Ser Ser Asn Gly Asn Ser Asn Asn Ala Ala Leu Pro Asn Gln
```

-continued

```
                485                 490                 495
Lys Ile Asn Val Ile Tyr Ser Val Gln Ser Asn Asp Lys Pro Glu Lys
            500                 505                 510

His Ala Asp Thr Tyr Arg Lys Trp Gly Tyr Met Ser Ser His Ile Pro
        515                 520                 525

Tyr Asp Leu Val Pro Glu Asn Val Ile Gly Asp Ile Asp Pro Asp Thr
    530                 535                 540

Lys Gln Pro Ser Leu Leu Leu Lys Gly Phe Pro Ala Glu Lys Gly Tyr
545                 550                 555                 560

Gly Asp Ser Ile Ala Tyr Val Ser Glu Pro Leu Asn Gly Ala Asn Ala
            565                 570                 575

Val Lys Leu Thr Ser Tyr Gln Val Leu Lys Met Glu Val Thr Asn Gln
        580                 585                 590

Thr Thr Gln Lys Tyr Arg Ile Arg Ile Arg Tyr Ala Thr Gly Gly Asp
    595                 600                 605

Thr Ala Ala Ser Ile Trp Phe His Ile Ile Gly Pro Ser Gly Asn Asp
610                 615                 620

Leu Thr Asn Glu Gly His Asn Phe Ser Ser Val Ser Ser Arg Asn Lys
625                 630                 635                 640

Met Phe Val Gln Gly Asn Asn Gly Lys Tyr Val Leu Asn Ile Leu Thr
            645                 650                 655

Asp Ser Ile Glu Leu Pro Ser Gly Gln Gln Thr Ile Leu Ile Gln Asn
        660                 665                 670

Thr Asn Ser Gln Asp Leu Phe Leu Asp Arg Ile Glu Phe Ile Ser Leu
    675                 680                 685

Pro Ser Thr Ser Thr Pro Thr Ser Thr Asn Phe Val Glu Pro Glu Ser
690                 695                 700

Leu Glu Lys Ile Ile Asn Gln Val Asn Gln Leu Phe Ser Ser Ser Ser
705                 710                 715                 720

Gln Thr Glu Leu Ala His Thr Val Ser Asp Tyr Lys Ile Asp Gln Val
            725                 730                 735

Val Leu Lys Val Asn Ala Leu Ser Asp Asp Val Phe Gly Val Glu Lys
        740                 745                 750

Lys Ala Leu Arg Lys Leu Val Asn Gln Ala Lys Gln Leu Ser Lys Ala
    755                 760                 765

Arg Asn Val Leu Val Gly Gly Asn Phe Glu Lys Gly His Glu Trp Ala
770                 775                 780

Leu Ser Arg Glu Ala Thr Met Val Ala Asn His Glu Leu Phe Lys Gly
785                 790                 795                 800

Asp His Leu Leu Leu Pro Pro Pro Thr Leu Tyr Pro Ser Tyr Ala Tyr
            805                 810                 815

Gln Lys Ile Asp Glu Ser Lys Leu Lys Ser Asn Thr Arg Tyr Thr Val
        820                 825                 830

Ser Gly Phe Ile Ala Gln Ser Glu His Leu Glu Val Val Val Ser Arg
    835                 840                 845

Tyr Gly Lys Glu Val His Asp Met Leu Asp Ile Pro Tyr Glu Glu Ala
850                 855                 860

Leu Pro Ile Ser Ser Asp Glu Ser Pro Asn Cys Cys Lys Pro Ala Ala
865                 870                 875                 880

Cys Gln Cys Ser Ser Cys Asp Gly Ser Gln Ser Asp Ser His Phe Phe
            885                 890                 895

Ser Tyr Ser Ile Asp Val Gly Ser Leu Gln Ser Asp Val Asn Leu Gly
        900                 905                 910
```

Ile Glu Phe Gly Leu Arg Ile Ala Lys Pro Asn Gly Phe Ala Lys Ile
       915                 920                 925

Ser Asn Leu Glu Ile Lys Glu Asp Arg Pro Leu Thr Glu Lys Glu Ile
       930                 935                 940

Lys Lys Val Gln Arg Lys Glu Gln Lys Trp Lys Lys Ala Phe Asn Gln
945                 950                 955                 960

Glu Gln Ala Glu Val Ala Thr Thr Leu Gln Pro Thr Leu Asp Gln Ile
               965                 970                 975

Asn Ala Leu Tyr Gln Asn Glu Asp Trp Asn Gly Ser Val His Pro His
           980                 985                 990

Val Thr Tyr Gln His Leu Ser Ala Val Val Val Pro Thr Leu Pro Lys
       995                 1000                1005

Gln Arg His Trp Phe Met Glu Asp Arg Glu Gly Glu His Val Val
   1010                1015                1020

Leu Thr Gln Gln Phe Gln Gln Ala Leu Asp Arg Ala Phe Gln Gln
   1025                1030                1035

Ile Glu Glu Gln Asn Leu Ile His Asn Gly Asn Phe Ala Asn Gly
   1040                1045                1050

Leu Thr Asp Trp Thr Val Thr Gly Asp Ala Gln Leu Ser Ile Phe
   1055                1060                1065

Asp Glu Asp Pro Val Leu Glu Leu Ala His Trp Asp Ala Ser Ile
   1070                1075                1080

Ser Gln Thr Ile Glu Ile Met Asp Phe Glu Asp Thr Glu Tyr
   1085                1090                1095

Lys Leu Arg Val Arg Gly Lys Gly Lys Gly Thr Val Thr Val Gln
   1100                1105                1110

His Gly Glu Glu Glu Leu Glu Thr Met Thr Phe Asn Ser Thr Ser
   1115                1120                1125

Phe Thr Thr Gln Glu Gln Thr Phe Tyr Phe Glu Gly Asp Thr Val
   1130                1135                1140

Asp Val His Val Gln Ser Glu Asn Asn Thr Phe Leu Ile Asp Ser
   1145                1150                1155

Val Glu Leu Ile Glu Ile Ile Glu Glu
   1160                1165

<210> SEQ ID NO 6
<211> LENGTH: 475
<212> TYPE: PRT
<213> ORGANISM: Bacillus thuringiensis

<400> SEQUENCE: 6

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
           20                  25                  30

Asn Gly Asn Gln Phe Ile Ile Ser Lys Gln Glu Trp Ala Thr Ile Gly
       35                  40                  45

Ala Tyr Ile Gln Thr Gly Leu Gly Leu Pro Val Asn Glu Gln Gln Leu
   50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
               85                  90                  95

Trp Asn Lys Asn Leu Tyr Pro Leu Ile Ile Lys Ser Ala Asn Asp Ile

```
            100                 105                 110
Ala Ser Tyr Gly Phe Lys Val Ala Gly Asp Pro Ser Ile Lys Lys Asp
            115                 120                 125

Gly Tyr Phe Lys Lys Leu Gln Asp Glu Leu Asp Asn Ile Val Asp Asn
        130                 135             140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
                180                 185                 190

Lys Leu Glu Gly Val Ile Asn Ile Gln Lys Arg Leu Lys Glu Val Gln
            195                 200                 205

Thr Ala Leu Asn Gln Ala His Gly Glu Ser Ser Pro Ala His Lys Glu
            210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
                260                 265                 270

Val Gln His Ile Lys Asn Gln Ile Asp Glu Ile Lys Glu Gln Leu Asp
            275                 280                 285

Ser Ala Gln His Asp Leu Asp Arg Asp Val Lys Ile Ile Gly Met Leu
            290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
            355                 360                 365

Ala Trp Leu Val Val Ala Gln Glu Ala Arg Asp Phe Thr Leu Asn Ala
            370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
            435                 440                 445

Tyr Lys Cys Pro Glu Asn Asn Phe Met Ile Tyr Trp Tyr Asn Asn Ser
            450                 455                 460

Asp Trp Tyr Asn Asn Ser Asp Trp Tyr Asn Asn
465                 470                 475
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 7

Val Tyr Ile Asp Arg Ile Glu Phe Val Pro
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Tyr Ile Asp Lys Ile Glu Phe Ile Pro
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Ile Asp Lys Ile Glu Phe Leu Pro
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Phe Leu Asp Arg Ile Glu Phe Ile Pro
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Phe Leu Asp Arg Ile Glu Phe Val Pro
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Tyr Val Asp Ser Ile Glu Phe Ile Pro
1               5                   10

<210> SEQ ID NO 13
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Tyr Ile Asp Arg Ile Glu Phe Ile Pro
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Tyr Val Asp Arg Ile Glu Phe Ile Pro
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Tyr Ile Asp Lys Ile Glu Phe Ile Pro
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Val Leu Asp Arg Ile Glu Phe Val Pro
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Tyr Leu Asp Arg Leu Glu Phe Val Pro
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Phe Ile Asp Arg Ile Glu Phe Ile Pro
```

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ile Leu Asp Lys Ile Glu Phe Leu Pro
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Val Leu Asp Lys Ile Glu Leu Ile Pro
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Phe Leu Asp Arg Ile Glu Phe Ile Ser
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Ile Asp Lys Ile Glu Phe Ile Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Arg Ile Glu Phe
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic

```
                peptide

<400> SEQUENCE: 24

Asp Arg Leu Glu Phe
1               5
```

What is claimed is:

1. A method for producing a pharmaceutical composition, the method comprising:
    (a) growing a non-sporulating form of a host bacterium that is genetically engineered to express a single type of nematicidal crystal protein, wherein the non-sporulating host bacterium produces native, bioactive nematicidal crystals formed from the single type of nematicidal crystal protein, wherein the host bacterium is grown in a growth medium, and optionally wherein the non-sporulating host bacterium releases the native, bioactive nematicidal crystals into the growth medium; and
    (b) isolating and concentrating the native, bioactive nematicidal crystals to form isolated, native, bioactive nematicidal crystals.

2. The method of claim 1, wherein the host bacterium is a Bacillus species, Bacillus thuringiensis (Bt), an E. coli species or P. fluorescens species.

3. The method of claim 1, wherein the non-sporulating host bacterium is genetically engineered to have a genetic mutation that results in a defect in sporulation such that the native, bioactive nematicidal crystal is trapped in the cytosol of the bacterium,
    wherein the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK.

4. The method of claim 1, wherein the host bacterium is genetically engineered to express the single type of nematicidal crystal protein under the control of a non-sporulation specific promoter,
    wherein the single type of nematicidal crystal protein is selected from the group consisting of Cry5B, Cry5C, Cry5D, Cry6A, Cry13A, Cry14A, Cry21A, Cry 21B, Cry 55B, and variants and truncations thereof,
    wherein the non-sporulation specific promoter is a Cry3A, GerA, GNAT, or TadA promoter.

5. The method of claim 1, further comprising a step of exposing the non-sporulating host bacterium to an antimicrobial compound to inactivate the host bacterium, wherein the antimicrobial compound is iodine, a pharmaceutical antibiotic, a beta lactam antibiotic, or an organic solvent.

6. The method of claim 5, further comprising a step of adding a food-grade oil to the inactivated host bacterium to extract the antimicrobial compound, soluble cell components, lipids, and cell wall debris from the nematicidal crystal protein.

7. The method of claim 5, further comprising a step of adding an organic solvent to the inactivated host bacterium to extract the antimicrobial compound from the nematicidal crystal protein.

8. The method of claim 5, further comprising a step of homogenizing the inactivated host bacterium to form a bacterial lysate that includes the native, bioactive nematicidal crystals.

9. The method of claim 1, further comprising a step of formulating the isolated native, bioactive nematicidal crystals in an orally-available dosage form.

10. A method for producing a pharmaceutical composition, the method comprising:
    (a) growing a non-sporulating form of a host bacterium that is engineered to express a single type of nematicidal crystal protein, wherein the non-sporulating host bacterium produces native bioactive nematicidal crystals formed from the single type of nematicidal crystal protein;
    (b) inactivating the grown non-sporulating host bacterium by exposing the grown non-sporulating host bacterium to an antimicrobial compound;
    (c) homogenizing the inactivated non-sporulating host bacterium to form a bacterial lysate; and
    (d) concentrating the native bioactive nematicidal crystals in the bacterial lysate to form isolated native, bioactive nematicidal crystals.

11. The method of claim 10, further comprising a step of concentrating the grown nonsporulating host bacterium before inactivating the grown non-sporulating host bacterium.

12. The method of claim 10, wherein the host bacterium is a Bacillus species, Bacillus thuringiensis (Bt), an E. coli or P. fluorescens species.

13. The method of claim 10, wherein the non-sporulating host bacterium is genetically engineered to have a genetic mutation that results in a defect in sporulation such that the native, bioactive nematicidal crystal is trapped in the cytosol of the bacterium,
    wherein the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK.

14. The method of claim 10, wherein the host bacterium is genetically engineered to express the single type of nematicidal crystal protein under the control of a non-sporulation specific promoter,
    wherein the single-type of cytoplasmic crystal protein is selected from the group consisting of Cry5B, Cry6A, Cry5C, Cry5D, Cry13A, Cry14A, Cry21A, Cry 21B, and Cry55A,
    wherein the non-sporulation specific promoter is a Cry3A, GerA, GNAT, or TadA promoter.

15. The method of claim 10, wherein the antimicrobial compound is iodine, a pharmaceutical antibiotic, a beta-lactam antibiotic or an organic solvent.

16. The method of claim 10, wherein the antimicrobial compound is an organic solvent selected from the group consisting of a terpene, hexane, and formaldehyde.

17. The method of claim 10, further comprising a step of extracting the antimicrobial compound and cell wall debris from the inactivated host bacterium.

18. The method of claim 10, further comprising a step of adding a food-grade oil to the inactivated host bacterium to extract the inactivating agent from the nematicidal crystal protein.

19. The method of claim 10, further comprising a step of adding an organic solvent to the inactivated host bacterium to extract the antimicrobial compound, soluble cell components, lipids, and cell wall debris from the nematicidal crystal protein.

20. The method of claim 19, further comprising a step of centrifuging the mixture of organic solvent and inactivated host bacterium to pellet the nematicidal crystal protein.

\* \* \* \* \*